(12) United States Patent
Zheng et al.

(10) Patent No.: US 11,820,760 B2
(45) Date of Patent: Nov. 21, 2023

(54) CRYSTALLINE POLYMORPHS OF BRUTON'S TYROSINE KINASE INHIBITORS

(71) Applicant: BIOGEN MA INC., Cambridge, MA (US)

(72) Inventors: Fengmei Zheng, Quincy, MA (US); Anton Peterson, Holliston, MA (US); Kalyan Vasudevan, Cambridge, MA (US); Chaomin Li, Cambridge, MA (US); Daniel B. Patience, Arlington, MA (US); Yiqing Lin, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 291 days.

(21) Appl. No.: 17/283,301

(22) PCT Filed: Oct. 15, 2019

(86) PCT No.: PCT/US2019/056242
§ 371 (c)(1),
(2) Date: Apr. 7, 2021

(87) PCT Pub. No.: WO2020/081514
PCT Pub. Date: Apr. 23, 2020

(65) Prior Publication Data
US 2021/0387972 A1    Dec. 16, 2021

Related U.S. Application Data

(60) Provisional application No. 62/745,741, filed on Oct. 15, 2018.

(51) Int. Cl.
*C07D 405/14* (2006.01)

(52) U.S. Cl.
CPC ........ *C07D 405/14* (2013.01); *C07B 2200/13* (2013.01)

(58) Field of Classification Search
CPC .... A61P 25/00; C07B 2200/13; C07D 405/14
See application file for complete search history.

(56) References Cited

U.S. PATENT DOCUMENTS

2016/0311802 A1    10/2016    Hopkins et al.

FOREIGN PATENT DOCUMENTS

| WO | 2014/064131 A2 | 5/2014 |
| WO | 2015/061247 A2 | 4/2015 |
| WO | 2018/191577 A1 | 10/2018 |

OTHER PUBLICATIONS

International Search Report and Written Opinion for Application No. PCT/US2019/056242, dated Dec. 13, 2019, 15 pages.

*Primary Examiner* — Kortney L. Klinkel
*Assistant Examiner* — Padmaja S Rao
(74) *Attorney, Agent, or Firm* — McCarter & English, LLP; Steven G. Davis; Xin Zhang

(57) ABSTRACT

Provided are crystalline forms of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, pharmaceutical compositions, methods of use and methods of making thereof.

31 Claims, 31 Drawing Sheets

CRYSTALLINE POLYMORPHS OF BRUTON'S TYROSINE KINASE INHIBITORS

RELATED APPLICATION

This application is a 35 U.S.C. § 371 national stage filing of International Application No. PCT/US2019/056242, filed on Oct. 15, 2019, which in turn claims the benefit of the filing date, under 35 U.S.C. § 119(e), of U.S. Provisional Application No. 62/745,741, filed on Oct. 15, 2018. The entire contents of the aforementioned applications of which are incorporated herein by reference.

TECHNICAL FIELD

The present invention relates to novel crystalline polymorphs of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. These polymorphs can be used for treating a disorder responsive to inhibition of Bruton's tyrosine kinase. In another aspect the invention relates to a process for preparation of the novel polymorphs.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCy), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

The present invention relates to crystalline forms (or polymorphs) B, C, D, E, F, H, J, K, L, M, N, P and Q of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In certain embodiments, the crystalline forms of the present application have improved stability and suitability for pharmaceutical uses. Other advantages may include favorable pharmacokinetic properties, ease of isolation, process reproducibility, suitability for large scale manufacturing process, etc.

The present invention also provides a pharmaceutical composition comprising at least one polymorph described herein and at least one pharmaceutically acceptable excipient.

One aspect of the present invention discloses a method of treating a disorder responsive to inhibition of Btk in a subject comprising administering to said subject an effective amount of a composition comprising a polymorph described herein.

The present invention also includes the use of a composition comprising a polymorph described herein for the manufacture of a medicament for the treatment of a disorder responsive to inhibition of Btk. Also provided is a polymorph described herein for use in treating a disorder responsive to inhibition of Btk.

DETAILED DESCRIPTION

Figure 1:
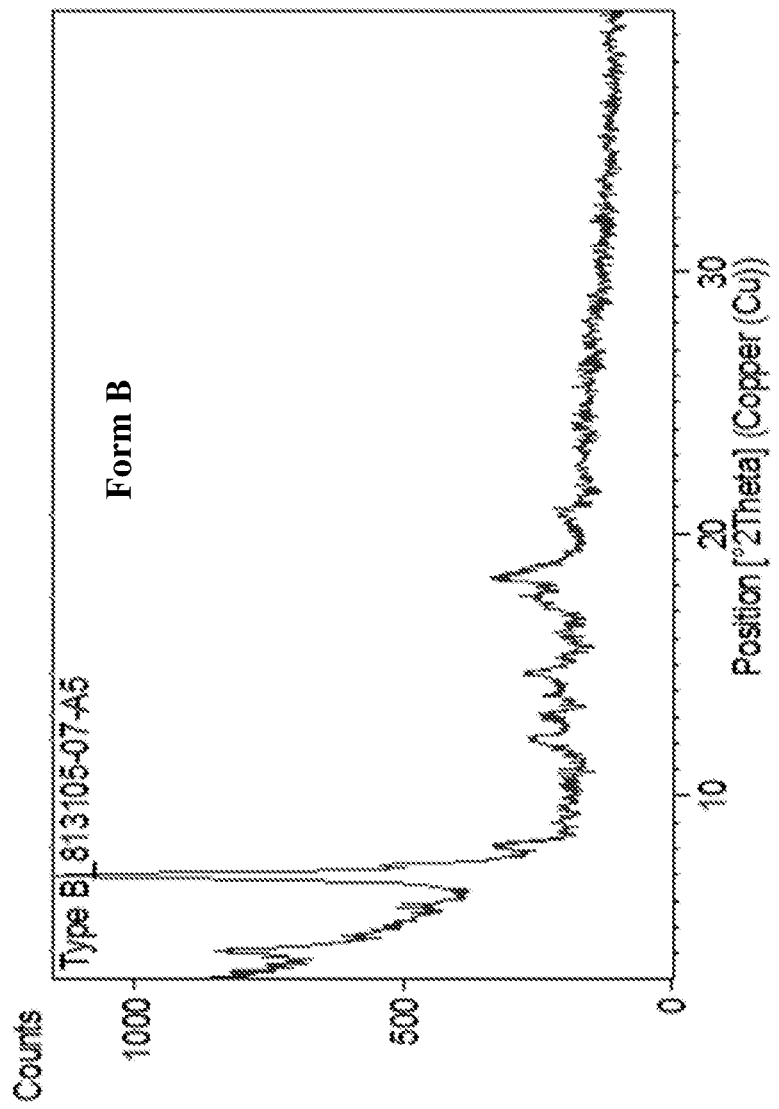
FIG. 1 depicts a powder X-ray diffraction (PXRD) pattern of crystalline Form B of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

As used herein, the term "compound" refers to (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide or any solid form thereof. The structure for the compound is shown below:

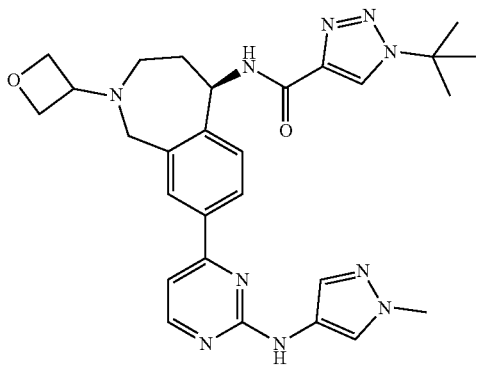 [SMILES: Cn1cc(Nc2nccc(-c3ccc4c(c3)CN(C3COC3)CC[C@H]4NC(=O)c3cn(C(C)(C)C)nn3)n2)cn1]

As used herein, the term "crystalline", "crystalline form" or "polymorph" refers to a solid form having a crystal form herein the individual molecules have a highly homogeneous regular locked-in chemical configuration. The crystalline form can be characterized by analytical methods, such as powder X-ray diffraction (PXRD), differential scanning calorimetry (DSC), thermogravimetric analysis (TGA), NMR, etc.

As used herein, an "anti-solvent crystallization" method involves the addition of an anti-solvent to a solution comprising the compound, which drastically reduces the solubility of the compound and results in the precipitation or crystallization of the compound. The precipitation of the compound can occur immediately or slowly over time. In some embodiments, after the addition of the anti-solvent, the resulting mixture can be cooled to a low temperature (e.g., below room temperature, between 0° C. and 10° C., or between 0° C. and 5° C.) to facilitate the precipitation of the crystalline form. Thereafter, the precipitate (crystals) may easily be separated by filtration, decanting, or centrifugation.

The term "anti-solvent", as used herein, refers to a solvent in which the compound is insoluble or has very low solubility. Suitable anti-solvents include, but are not limited to, water, hydrocarbons, including petroleum ether, pentane, hexane(s), heptane, octane, isooctane, cyclopentane, cyclohexane, methylcyclohexane, benzene, toluene, xylene, n-butanol.

As used herein, a "reverse anti-solvent crystallization" method involves the addition of a solution of the compound (obtained by dissolving the compound in a solvent to form a clear solution) to an anti-solvent until a precipitate appears. Alternatively, the solution is added to added to a fixed volume of the anti-solvent. The desired crystalline form can form or precipitate out slowly over time. In some embodiments, after the addition of the solvent, the resulting mixture can be cooled to a low temperature (e.g., below room temperature, between 0° C. and 10° C., or between 0° C. and 5° C.) to facilitate the precipitation or crystallization of the crystalline form. Thereafter, the precipitate (crystals) may easily be separated by filtration, decanting, or centrifugation.

As used herein "slurry cycling crystallization" method comprises suspending the compound in a solvent followed by heating and slow cooling, wherein the heating and cooling steps can be optionally repeated for 1-10 times to yield the desired crystalline form. The mixture of the compound and the solvent can be heated to a temperature between 30° C. and 150° C., between 30° C. and 100° C., between 30° C. and 70° C., or between 40° C. and 60° C. In one embodiment, the mixture can be heated to 50° C. The mixture can be heated at the desired temperature for a period of time, e.g., between 10 minutes and 10 hours, between 10 minutes and 5 hours, between 10 minutes and 2 hours, between 10 minutes and 1 hour, between 20 minutes and 40 minutes, or between 1 hours and 5 hours. In one embodiment, the mixture is heated for 30 minutes. The heated mixture can then be cooled down slowly to room temperature or a low temperature between 0° C. and 15° C., or between 0° C. and 10° C. or between 0° C. and 5° C. In one embodiment, the mixture can be cooled to 5° C. The cooling is carried out slowly, for example, at a rate of 0.1-0.5° C./minutes (e.g., 0.1° C./minute).

As used herein "slurry conversion crystallization" method involves stirring of the suspension of the compound in a solvent for a period time sufficient for the conversion of the compound from one solid form to another solid form. In some embodiments, the mixture of the compound and the solvent can be stirred for 1-5 hours, for 1-10 hours, for 1 hour to 1 day, for 1 day to 10 days, or for 1 day to 5 days. In some embodiments, the mixture is stirred for 1 day, 2 days, 3 days, 4 days or 5 days.

As used herein "liquid vapor diffusion crystallization" method involves the diffusion of the vapor of a volatile solvent, in which the compound is not soluble or has low solubility, into a solution containing the compound. The vapor of the volatile solvent diffuses into the solution, decreasing the overall solubility of the compound and resulting in the compound to precipitate out of the solution. In some embodiments, the method is carried out by adding the volatile solvent to the solution and keeping the resulting mixture in a sealed container. In some embodiments, the solution can be evaporated to dryness at room temperature.

As used herein "ionic liquid induced crystallization" method involves dissolving the compound in a solvent in the presence of an ionic liquid, and allowing the slow evaporation of the solvent to yield the desired solid form of the compound. Exemplary ionic liquid include, but are not limited to, 1,3-dimethylimidazolium trifluoroacetic acid ([dmin]$CF_3COOH$), 1,3-dimethylimidazolium perchlorate ([dmin]$ClO_4$), 1-butyl-3-methylimidazolium hexafluorophosphate ([bmim]$PF_6$) and 1-ethyl-3-methylimidazolium hexafluroantimonate ([emim]$SbF_6$).

As used herein, "polymer induced crystallization" method involves stirring a solution of compound in a solvent in the presence of a polymer mixture to yield the desired solid form. Exemplary polymer mixture include, but are not limited to, a mixture of polymers selected from polyvinyl pyrrolidone (PVP), polyvinyl alcohol (PVA), polyvinylchloride (PVC), polyvinyl acetate (PVAC), hypromellose (HPMC), and methyl cellulose (MC). In some embodiments, the polymer mixture is a mixture of polyvinyl pyrrolidone (PVP), polyvinyl alcohol (PVA), polyvinylchloride (PVC), polyvinyl acetate (PVAC), hypromellose (HPMC), and methyl cellulose (MC) with mass ratio of 1:1:1:1:1:1).

As used herein, "fast evaporation crystallization" method involves dissolving a solid form of the compound in a solvent followed by fast evaporation of the solvent to yield the desired crystalline form. Fast solvent evaporation can be achieved, for example, by exposing the solution of the compound to air at room temperature to allow the volatile solvent to evaporate. Alternatively, the solvent can be evaporated under vacuum and/or at an elevated temperature (e.g., higher than room temperature).

The term "crystalline Form B", "crystalline Form C", "crystalline Form D", "crystalline Form E", "crystalline Form F", "crystalline Form H", "crystalline Form J", "crystalline Form K", "crystalline Form L", "crystalline Form M", "crystalline Form N", "crystalline Form P" or "crystalline Form Q" relates to a specific crystalline form of (R)-1-(tert-butyl)-N-(8-(2-((1-methyl-1H-pyrazol-4-yl) amino)pyrimidin-4-yl)-2-(oxetan-3-yl)-2,3,4,5-tetrahydro-1H-benzo[c]azepin-5-yl)-1H-1,2,3-triazole-4-carboxamide as defined below.

The present invention relates to various crystalline polymorphs of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and a process for preparing the same. Any suitable crystallization method known in the art can be used to prepared the crystalline forms of the compound described herein. Exemplary crystallization methods include, but are not limited to, anti-solvent crystallization method, reverse anti-solvent crystallization method, slurry cycling crystallization method, slurry conversion crystallization method, liquid vapor diffusion crystallization method, polymer induced crystallization method, and fast evaporation crystallization method.

In one aspect, the present invention provides crystalline Form B of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form B is characterized by at least three or at least four powder X-ray diffraction (PXRD) peaks at 2θ angles selected from 4.1°, 7.0°, 8.1°, 12.1° and 18.3°. In another embodiment, crystalline Form B is characterized by PXRD peaks at 2θ angles selected from 4.1°, 7.0°, 8.1°, 12.1° and 18.3°. In another embodiment, crystalline Form B is characterized by at least three, at least four, at least five, at least six, at least seven, at least eight or nine PXRD peaks at 2θ angles selected from 4.1°, 7.0°, 8.1°, 12.1°, 13.0°, 14.7°, 17.6°, 18.3° and 20.7°. In some embodiments, the peaks described in the above embodiments for crystalline Form B have a relative intensity of at least 1%, at least 2%, at least 5%, at least 10%, or at least 15%. In some embodiments, crystalline Form B has a PXRD pattern that is substantially the same as PXRD pattern shown in FIG. 1.

As used herein, the term "relative intensity" refers to a ratio of the peak intensity for the peak of interest versus the peak intensity for the largest peak.

Figure 2A:
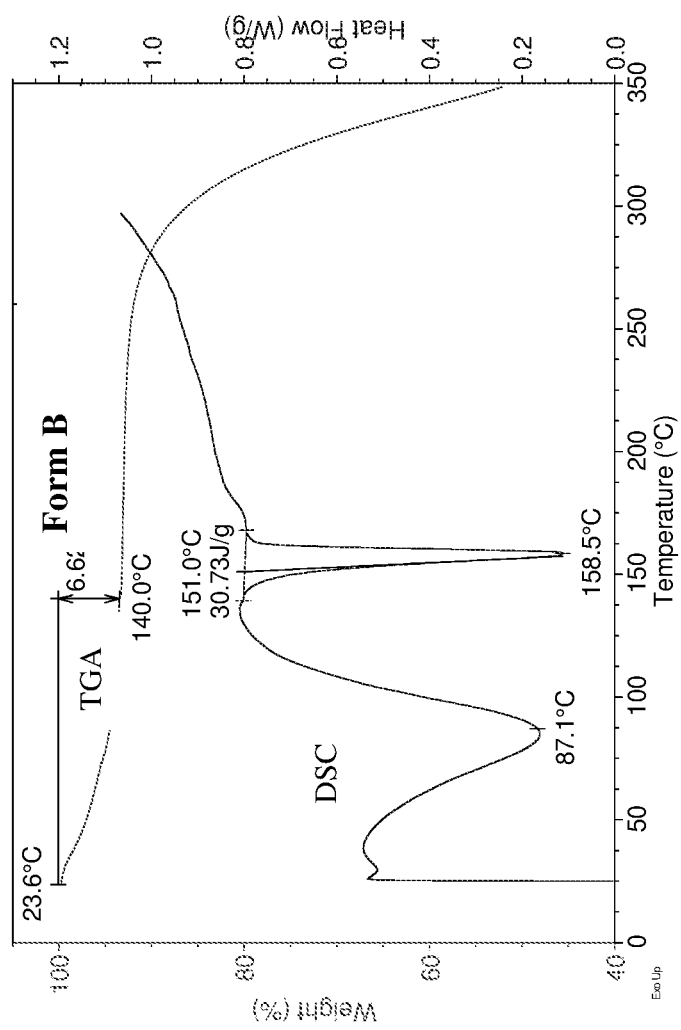
FIG. 2A depicts differential scanning calorimetry (DSC) and thermal gravimetric analysis (TGA) profiles of crystalline Form B of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In some embodiments, crystalline Form B has a DSC profile that is substantially the same as DSC profile shown in FIG. 2A. In particular, crystalline Form B is characterized by an onset temperature at 151.0° C.±2° C. in the DSC profile. In another embodiment, crystalline Form B has a melting temperature of 158.5° C.±2° C.

Figure 2B:
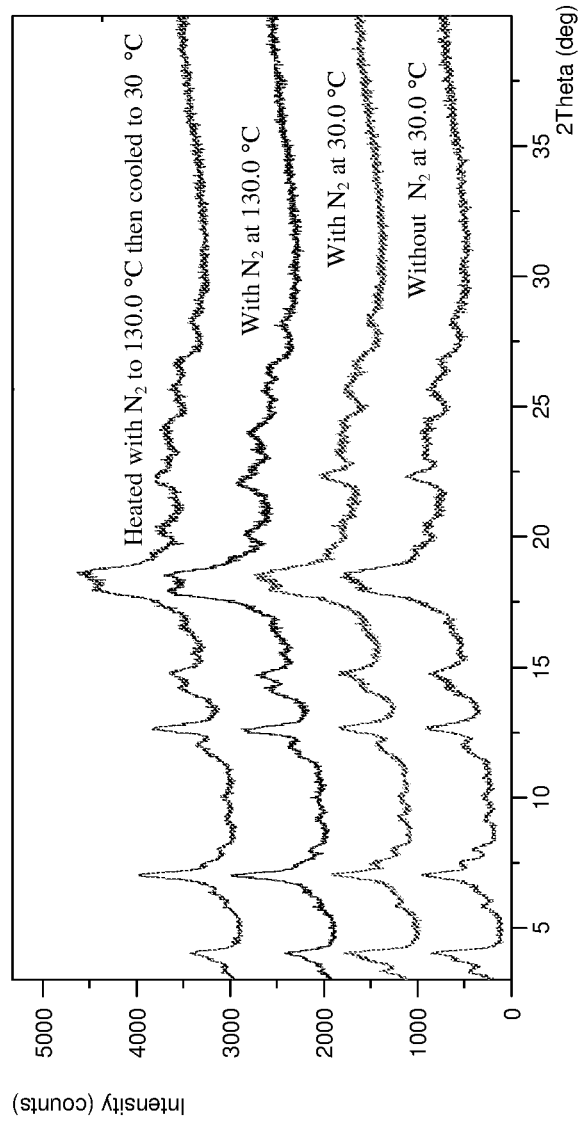
FIG. 2B depicts various temperature powder X-ray diffraction (VT-PXRD) patterns of crystalline Form B.

In some embodiments, crystalline Form B has a TGA profile that is substantially the same as the TGA profile shown in FIG. 2A. In particular, the TGA profile indicates that crystalline Form B is a hygroscopic anhydrate. As shown in FIG. 2B, VT-PXRD patterns of Form B shows no form conversion after the sample was heated to 130° C. under $N_2$, indicating that Form B is a hygroscopic anhydrate.

In some embodiments, crystalline Form B is characterized by, for example, DSC, TGA and PXRD. In one embodiment, crystalline Form B is characterized by PXRD alone or PXRD in combination with one or more of DSC and TGA described above.

"Hygroscopic" as used herein, means that the crystalline form can readily absorb or adsorb water from its surroundings.

"Anhydrate" or "anhydrous" as used herein, means that the crystalline form comprises substantially no water in the crystal lattice e.g., less than 1% by weight as determined by, for example, TGA analysis or other quantitative analysis.

In some embodiments, crystalline Form B is at least 70%, 80%, 85%, 90%, 95%, 97%, 99%, 99.5% or 99.9% pure. The purity of Form B is determined by dividing the weight of crystalline Form B in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form B of the compound.

In one aspect, the present invention provides a method for preparing crystalline Form B of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is an anti-solvent or reverse anti-solvent crystallization method described herein. In a particular embodiment of the above disclosed method, crystalline Form B can be obtained using crystalline form A as starting material, dichloromethane (DCM) as the solvent and toluene as the anti-solvent. In one embodiment, crystalline Form B can be obtained by dissolving Form A in dichloromethane followed by the addition of anti-solvent, such as toluene.

In another aspect, the present invention provides crystalline Form C of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form C is characterized by at least three, at least four or at least five PXRD peaks at 2θ angles selected from 3.4°, 5.5°, 6.9°, 7.7°, 8.8° and 12.5°. In another embodiment, crystalline Form C is characterized by PXRD peaks at 2θ angles selected from 3.4°, 5.5°, 6.9°, 7.7°, 8.8° and 12.5°. In some embodiments, crystalline Form C is characterized by at least three, at least four, at least five, at least six, at least seven, at least eight, at least nine, at least ten, at least eleven, at least twelve or at least thirteen PXRD peaks at 2θ angles selected from 3.4°, 5.5°, 6.9°, 7.7°, 8.8°, 9.8°, 12.5°, 14.2°, 15.6°, 17.6°, 18.6°, 20.2° and 25.3°. In some embodiment, the peaks described in the above embodiments for crystalline Form C have a relative intensity of at least 1%, at least 2%, at least 5%, at least 10%, or at least 15%. In some embodiments, crystalline Form C has a PXRD pattern that is substantially the same as PXRD pattern shown in FIG. 3.

Figure 4A:
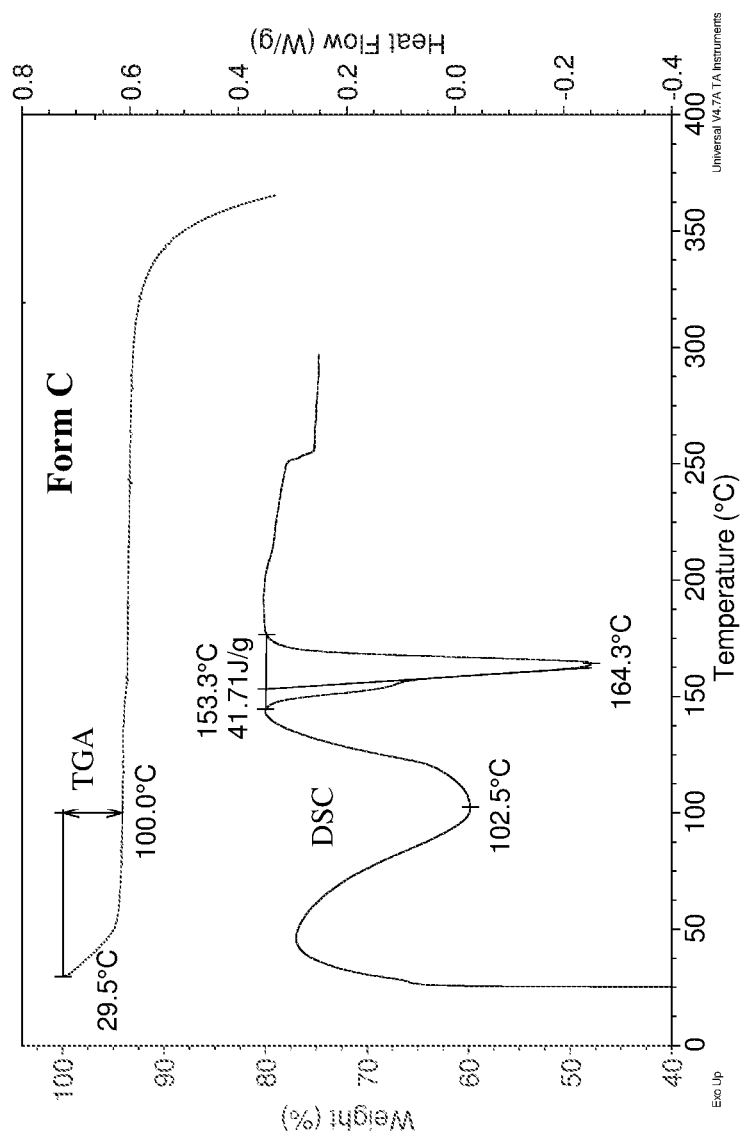
FIG. 4A depicts differential scanning calorimetry (DSC) and thermal gravimetric analysis (TGA) profiles of crystalline Form C of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another embodiment, crystalline Form C has a DSC profile that is substantially the same as DSC profile shown in FIG. 4A. In particular, crystalline Form C is characterized by an onset temperature at 153.3° C.±2° C. in the DSC profile. In another embodiment, crystalline Form C has a melting temperature of 164.3° C.±2° C.

Figure 4B:
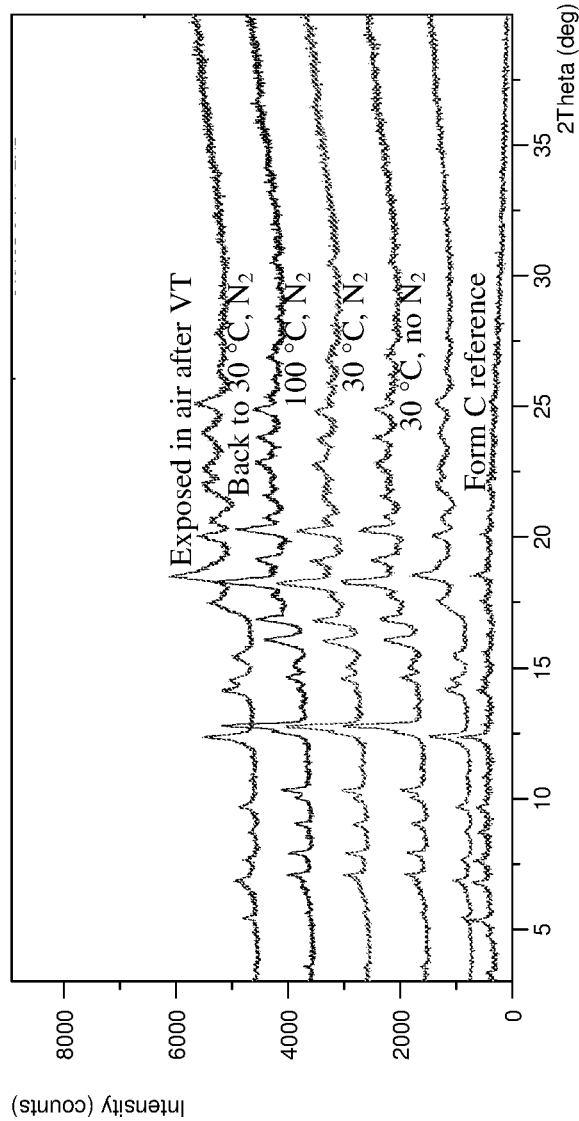
FIG. 4B depicts VT-PXRD patterns of crystalline Form C.

In yet another embodiment, crystalline Form C has a TGA profile that is substantially same as the TGA profile shown in FIG. 4A. In particular, the TGA profile indicates that crystalline Form C is a hydrate. In addition, as shown in FIG. 4B, Form C converts to a new crystalline form, Form L, after dehydration by $N_2$ purging at 30° C. for 20 minutes. Form L converts back to Form C after exposure to air for about 2.5 hours and re-absorbs water. VT-PXRD patterns suggests that Form C is a hydrate.

In some embodiments, crystalline Form C is characterized by, for example, DSC, TGA and PXRD. In one embodiment, crystalline Form C is characterized by PXRD alone or PXRD in combination with one or more of DSC and TGA described above.

As used herein, "hydrate" refers to a crystalline solid adduct containing (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide and either stoichiometric or nonstoichiometric amounts of a water incorporated within the crystal structure. Techniques known in the art to determine the amount of water present include, for example, TGA and Karl Fisher (KF) analysis. In certain embodiments, a hydrate is a monohydrate (i.e., one molecule of water for every molecule of the compound). In certain embodiments, a hydrate is a hemihydrate (i.e., one molecule of water for every two molecules of the compound).

In some embodiments, crystalline Form C is at least 70%, 80%, 85%, 90%, 95%, 97%, 99%, 99.5% or 99.9% pure. The purity of Form C is determined by dividing the weight of crystalline Form C in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form C of the compound.

In an aspect, the present invention provides a method for preparing crystalline Form C of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is an anti-solvent or a reverse anti-solvent crystallization method described herein. In a particular embodiment of the above disclosed method, crystalline Form C can be obtained using crystalline Form A as starting material, dimethylformamide (DMF) as the solvent and toluene as the anti-solvent. In one embodiment, crystalline Form C can be obtained by dissolving crystalline Form A of the compound in DMF followed by addition of toluene. In another embodiment, crystalline Form C can be obtained by mixing toluene and crystalline Form A followed by addition of DMF.

In another aspect, the present invention provides crystalline Form D of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form D is characterized by at least three, at least four or at least five PXRD peaks at 2θ angles selected from 5.4°, 6.3°, 8.3°, 10.9°, 12.5° and 19.1°. In another embodiment, crystalline Form D is characterized by PXRD peaks at 2θ angles selected from 5.4°, 6.3°, 8.3°, 10.9°, 12.5° and 19.1°. In some embodiments, crystalline Form D is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty or at least twenty-one PXRD peaks at 2θ angles selected from 5.4°, 6.3°, 8.3°, 10.9°, 12.5°, 13.7°, 14.4°, 15.7°, 16.3°, 17.5°, 18.9°, 19.1°, 19.6°, 22.7°, 23.8°, 24.6°, 25.0°, 25.9°, 28.4°, 29.0° and 30.4°. In some embodiments, the peaks described in the above embodiments for crystalline Form D have a relative intensity of at least 1%, at least 2%, at least 5%, at least 10%, or at least 15%. In some embodiments, crystalline Form D has a PXRD pattern that is substantially the same as PXRD pattern shown in FIG. 5.

Figure 6:
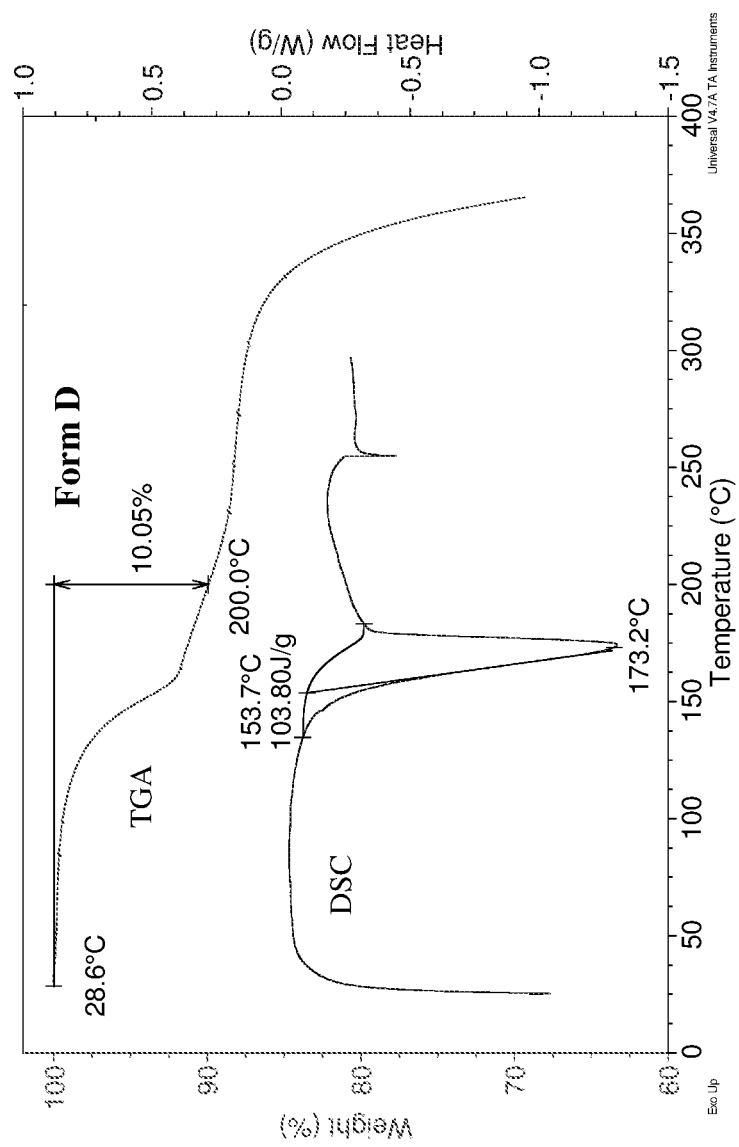
FIG. 6 depicts differential scanning calorimetry (DSC) and thermal gravimetric analysis (TGA) profiles of crystalline Form D of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In some embodiments, crystalline Form D has a DSC profile that is substantially the same as DSC profile shown in FIG. 6. In particular, crystalline Form D is characterized by an onset temperature at 153.7° C.±2° C. in the DSC profile. In another embodiment, crystalline Form D has a melting temperature of 173.2° C.±2° C.

In one embodiment, crystalline Form D has a TGA profile that is substantially same as the TGA profile shown in FIG. 6 In particular, the TGA profile indicates that crystalline Form D is an acetic acid solvate.

Figure 7:
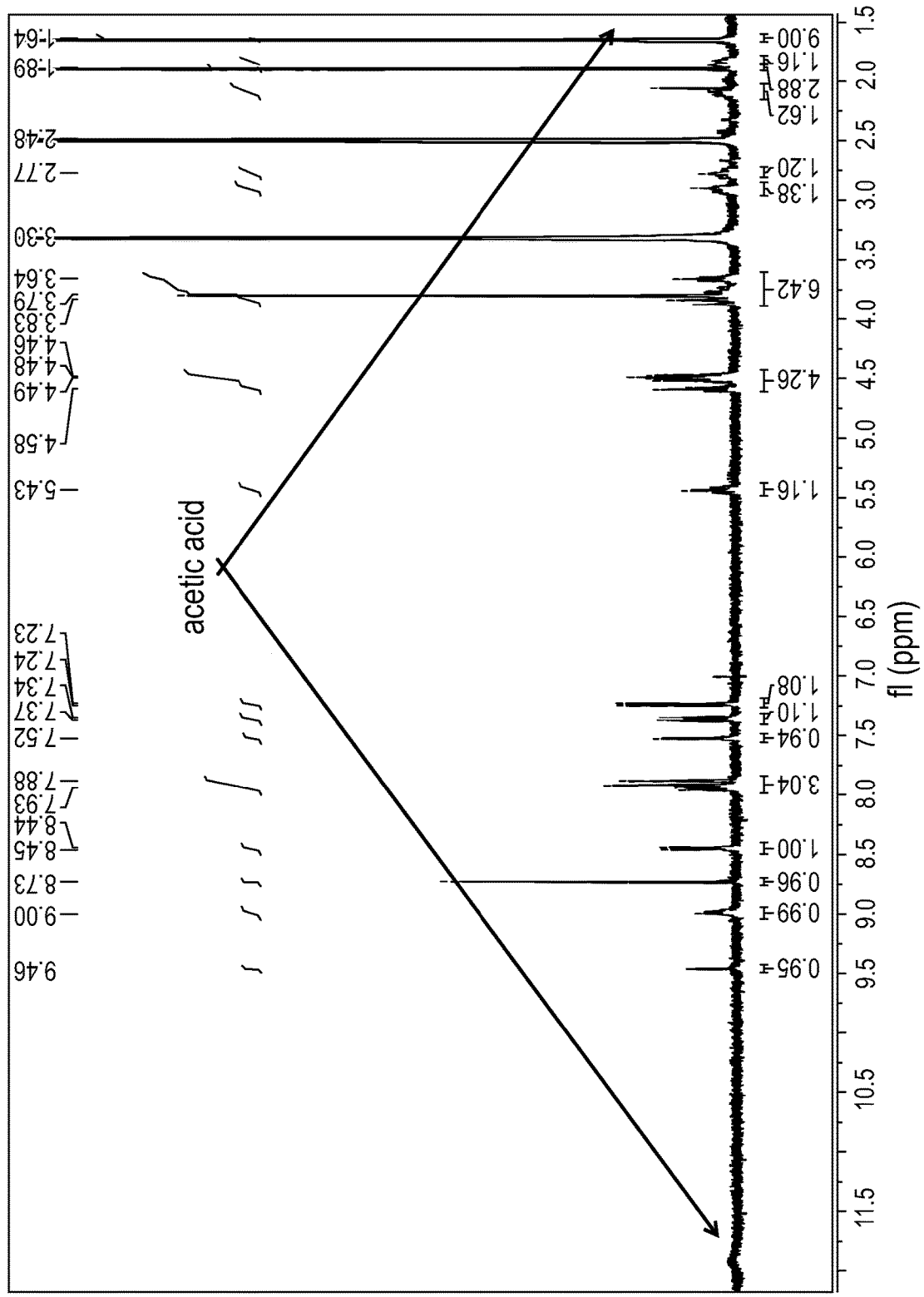
FIG. 7 shows $^1$H NMR spectrum of crystalline Form D of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another embodiment, crystalline Form D is characterized by the $^1$H NMR as shown in FIG. 7.

In some embodiments, crystalline Form D is characterized by, for example, $^1$H NMR, DSC, TGA and PXRD. In one embodiment, crystalline Form F is characterized by PXRD alone or PXRD in combination with one or more of DSC, TGA and $^1$H NMR described above.

In some embodiments, crystalline Form D is at least 70%, 80%, 85%, 90%, 95%, 97%, 99%, 99.5% or 99.9% pure. The purity of Form D is determined by dividing the weight of crystalline Form D in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form D of the compound.

In an aspect, the present invention provides a method for preparing crystalline Form D of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is the fast evaporation crystallization method. In a particular embodiment, crystalline Form D can be obtained using crystalline form A as the starting material and methyl ethyl ketone (MEK) as the solvent. In another embodiment, crystalline Form D can be obtained by dissolving crystalline Form A in MEK followed by evaporation of MEK at room temperature to yield crystalline Form D.

In yet another aspect, the present invention provides crystalline Form E of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form E is characterized by at least three, at least four or at least five PXRD peaks at 2θ angles selected from 4.2°, 5.1°, 5.9°, 7.0°, 12.0° and 16.9°. In another embodiment, crystalline Form E is characterized by PXRD peaks at 2θ angles selected from 4.2°, 5.1°, 5.9°, 7.0°, 12.0° and 16.9°. In another embodiment, crystalline Form E is characterized by at least three, at least four, at least five, at least six, at least seven, at least eight, at least nine, at least ten, at least eleven, at least twelve, at least thirteen, at least fourteen, at least fifteen or at least sixteen PXRD peaks at 2θ angles selected from 4.2°, 5.1°, 5.9°, 7.0°, 8.5°, 8.7°, 9.8°, 10.2°, 12.0°, 12.4°, 13.7°, 16.9°, 18.1°, 18.7°, 20.7° and 26.6°. In some embodiments, the peaks described in the above embodiments for crystalline Form E have a relative intensity of at least 1%, at least 2%, at least 5%, at least 10%, or at least 15%. In another embodiment, crystalline Form E has a PXRD pattern that is substantially the same as PXRD pattern shown in FIG. 8.

Figure 9:
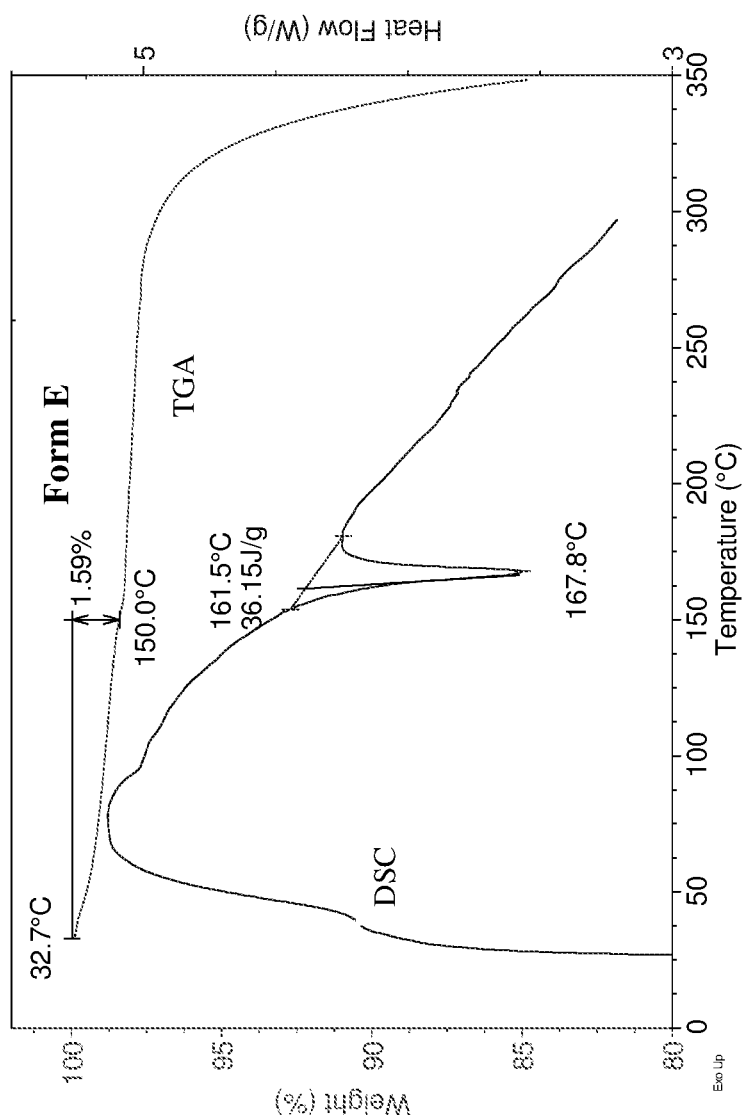
FIG. 9 depicts differential scanning calorimetry (DSC) and thermal gravimetric analysis (TGA) profiles of crystalline Form E of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In yet another embodiment, crystalline Form E has a DSC profile that is substantially the same as DSC profile shown in FIG. 9. In particular, crystalline Form E is characterized by an onset temperature at 161.5° C.±2° C. in the DSC profile. In another embodiment, crystalline Form E has a melting temperature of 167.8° C.±2° C.

In yet another embodiment, crystalline Form E has a TGA profile that is substantially same as the TGA profile shown in FIG. 9. In particular, the TGA profile indicates that crystalline Form E is an anhydrate.

In some embodiments, crystalline Form E is characterized by, for example, DSC, TGA and PXRD. In one embodiment, crystalline Form E is characterized by PXRD alone or PXRD in combination with one or more of DSC and TGA described above.

In some embodiments, crystalline Form E is at least 70%, 80%, 85%, 90%, 95%, 97%, 99%, 99.5% or 99.9% pure. The purity of Form E is determined by dividing the weight of crystalline Form E in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In an embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form E of the compound.

In an aspect, the present invention provides a method for preparing crystalline Form E of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is selected from slurry cycling, slurry conversion, liquid vapor diffusion and ionic liquid induced crystallization methods described herein. In a specific embodiment, crystalline Form E can be obtained by suspending crystalline Form A in a solvent (such as methyl ethyl ketone (MEK)), heating the slurry to an elevated temperature, slowly cooling and repeating the heating and cooling steps for at least one, two, three, four or more times to yield crystalline Form E. In a particular embodiment, crystalline Form A is suspended in a solvent (such as acetone/isopropyl acetate (IPAc)=1:9) and then heated to 50° C. for 30 minutes. The resulting mixture is then slowly cooled to 5° C. The heating and cooling step is repeated three or more times to yield crystalline Form E. In another embodiment, crystalline Form E can be obtained by suspending crystalline form A in a solvent and stirring the slurry for a period of time, such as 30 minutes to 1 hour, 1 hour to 5 hours, 1 hour to 1 day, 1 day to 5 days or longer, followed by isolating the solid. In yet another embodiment, crystalline Form E can be obtained by dissolving crystalline form A in a solvent (such as CHCl₃), adding a volatile anti-solvent (such as n-heptane) to the solution, and allowing sufficient time for anti-solvent to interact with the solution in a sealed container to yield crystalline Form E as a precipitate. In another embodiment, crystalline Form E can be obtained by slow evaporation of a solution containing crystalline form A and an ionic liquid (such as [bmim]PF₆ or [emim]SbF₆) in a solvent (such as methyl acetate (MeOAc) or THF).

In one aspect, the present invention provides crystalline Form F of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form F is characterized by at least three, at least four, at least five, or at least six PXRD peaks at 2θ angles selected from 3.6°, 4.7°, 5.7°, 7.3°, 8.9°, 12.4° and 16.8°. In another embodiment, crystalline Form F is characterized by PXRD peaks at 2θ angles selected from 3.6°, 4.7°, 5.7°, 7.3°, 8.9°, 12.4° and 16.8°. In another embodiment, crystalline Form F is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen or at least nineteen PXRD peaks at 2θ angles selected from 3.6°, 4.7°, 5.7°, 7.3°, 8.9°, 9.7°, 12.4°, 13.2°, 14.2°, 14.6°, 16.8°, 18.1°, 19.1°, 20.6°, 22.5°, 23.7°, 24.3°, 25.5° and 29.1°. In some embodiments, the peaks described in the above embodiments for crystalline Form F have a relative intensity of at least 1%, at least 2%, at least 5%, at least 10%, or at least 15%. In one embodiment, crystalline Form F has a PXRD pattern that is substantially the same as PXRD pattern shown in FIG. 10.

Figure 11:
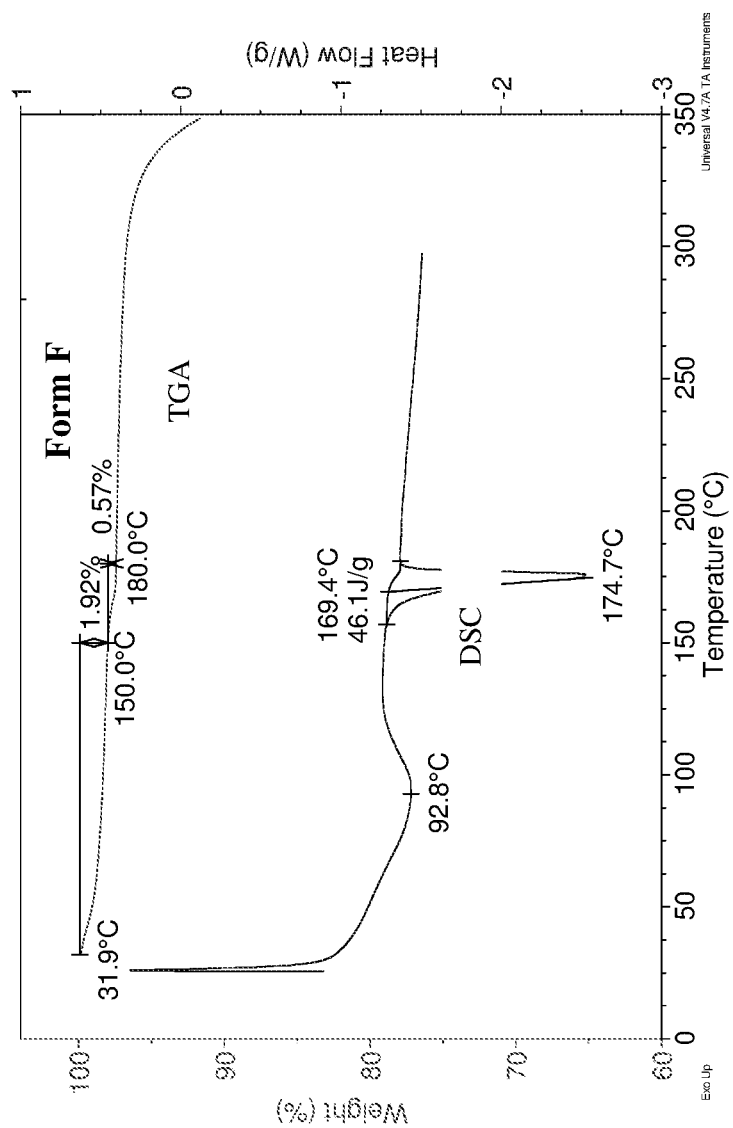
FIG. 11 depicts differential scanning calorimetry (DSC) and thermal gravimetric analysis (TGA) profiles of crystalline Form F of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form F has a DSC profile that is substantially the same as DSC profile shown in FIG. 11. In particular, crystalline Form F is characterized by an onset temperature at 169.4° C.±2° C. in the DSC profile. In another embodiment, crystalline Form F has a melting temperature of 174.7° C.±2° C.

In another embodiment, crystalline Form F has a TGA profile that is substantially same as the TGA profile shown in FIG. 11. In particular, the TGA profile indicates that crystalline Form F is an anhydrate.

In some embodiments, crystalline Form F is characterized by, for example, DSC, TGA and PXRD. In one embodiment, crystalline Form F is characterized by PXRD alone or PXRD in combination with one or more of DSC and TGA described above.

In some embodiments, crystalline Form F is at least 70%, 80%, 85%, 90%, 95%, 97%, 99%, 99.5% or 99.9% pure. The purity of Form F is determined by dividing the weight of crystalline Form E in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form F of the compound.

In an aspect, the present invention provides a method for preparing crystalline Form F of (R)-1-(tert-butyl)-N-(8-(2-

((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is selected from slurry cycling, slurry conversion and polymer induced crystallization methods described herein. In a particular embodiment, crystalline Form F can be obtained by suspending crystalline Form A in a solvent (such as methyl isobutyl ketone (MIBK)) followed by heating to an elevated temperature (e.g., 50° C.) for a period of time (e.g., 30 minutes, 1 hour, 2 hours etc.) and slowly cooling to a low temperature (e.g., 5° C.). The heating and cooling can be repeated for at least one, two, three, four or more times to yield crystalline Form F. In another embodiment, crystalline Form F can be obtained by suspending crystalline Form A in a solvent (such as MIBK) to form a slurry and stir the slurry for a period of time (e.g., 30 minutes to 1 hour, 1 hour to 5 hours, 1 hour to 1 day, 1 days to 5 days) to allow the conversion of crystalline Form A to Form F. In yet another embodiment, crystalline Form F can be obtained by stirring a mixture of Form A in a solvent (such as MeOH) and a polymer mixture (such as a polymer mixture of polyvinyl pyrrolidone (PVP), polyvinyl alcohol (PVA), polyvinylchloride (PVC), polyvinyl acetate (PVAC), hypromellose (HPMC), methyl cellulose (MC) with mass ratio of 1:1:1:1:1:1) for a period of time to allow the conversion of crystalline Form A to Form F. In one embodiment, the mixture can be stirred for 1 to 5 days.

In yet another aspect, the present invention provides crystalline Form H of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form H is characterized by at least east three or at least four PXRD peaks at 2θ angles selected from 4.6°, 6.3°, 8.4°, 13.4° and 18.7°. In another embodiment, crystalline Form H is characterized by PXRD peaks at 2θ angles selected from 4.6°, 6.3°, 8.4°, 13.4° and 18.7°. In yet another embodiment, crystalline Form H is characterized by at least three, at least four, at least five, at least six, at least seven, at least eight, at least nine, at least ten, at least eleven, at least twelve, at least thirteen, at least fourteen or at least fifteen PXRD peaks at 2θ angles selected from 4.6°, 6.3°, 8.4°, 8.8°, 11.0°, 13.4°, 14.9°, 15.6°, 16.9°, 18.7°, 19.3°, 22.6°, 24.1°, 25.3°, and 26.8°. In some embodiments, the peaks described in the above embodiments for crystalline Form H have a relative intensity of at least 1%, at least 2%, at least 5%, at least 10%, or at least 15%. In some embodiments, crystalline Form H has a PXRD pattern that is substantially the same as PXRD pattern shown in FIG. 12.

Figure 13A:
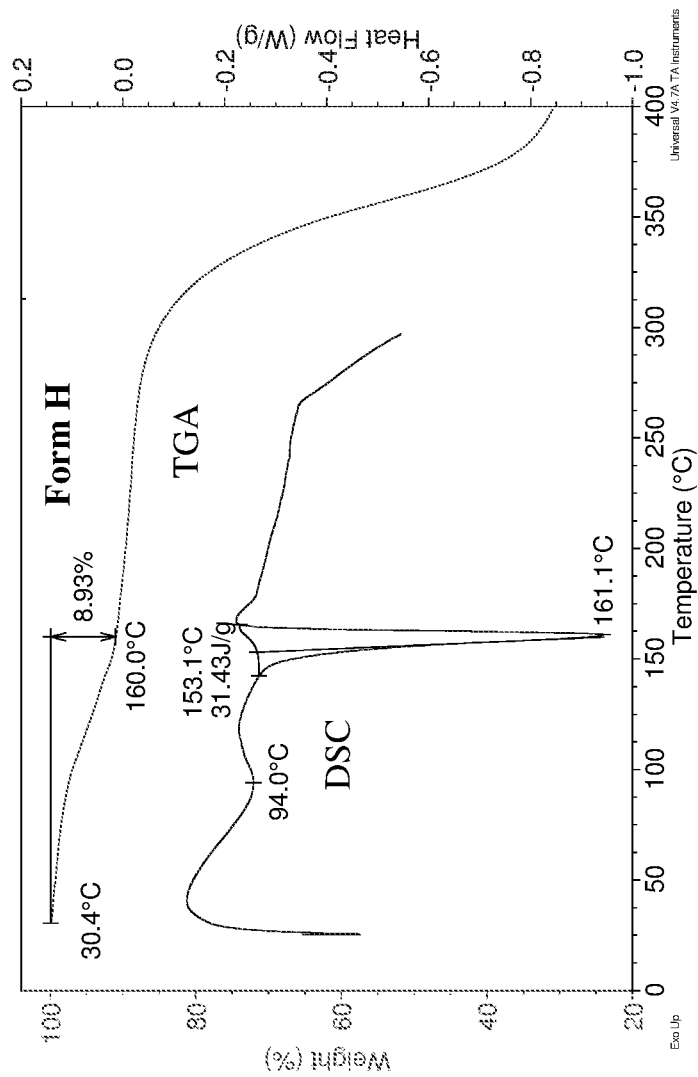
FIG. 13A depicts differential scanning calorimetry (DSC) and thermal gravimetric analysis (TGA) profiles of crystalline Form H of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another embodiment, crystalline Form H has a DSC profile that is substantially the same as DSC profile shown in FIG. 13A. In particular, crystalline Form H is characterized by an onset temperature at 153.1° C.±2° C. in the DSC profile. In another embodiment, crystalline Form H has a melting temperature of 161.1° C.±2° C.

Figure 13B:
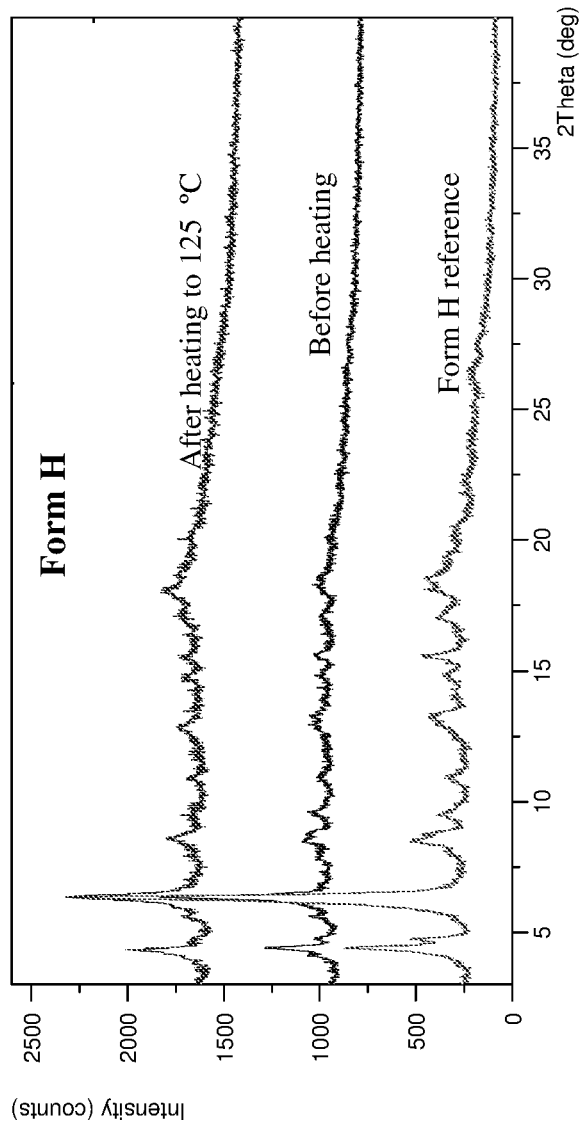
FIG. 13B depicts PXRD pattern comparison of Form H before after heating.

In yet another embodiment, crystalline Form H has a TGA profile that is substantially same as the TGA profile shown in FIG. 13A. In particular, the TGA profile showed small amount of weight loss (1.1% up to 140° C.) due to loss of the absorbed water, which suggests that crystalline Form H is an anhydrate. In addition, as shown in FIG. 13B, when a sample of Form H was heated to 125° C., no form conversion was observed, which is consistent with Form H being anhydrate.

In some embodiments, crystalline Form H is characterized by, for example, DSC, TGA and PXRD. In one embodiment, crystalline Form H is characterized by PXRD alone or PXRD in combination with one or more of DSC and TGA described above.

In some embodiments, crystalline Form H is at least 70%, 80%, 85%, 90%, 95%, 97%, 99%, 99.5% or 99.9% pure. The purity of Form H is determined by dividing the weight of crystalline Form H in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form H of the compound.

In an aspect, the present invention provides a method for preparing crystalline Form H of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is slurry cycling crystallization method described herein. In a particular embodiment, crystalline Form H can be obtained by suspending crystalline Form A in 2-methyl-tetrahydrofuran (2-MeTHF) followed by heating and slow cooling. The heating and cooling can be repeated for at least one, two, three, four, five or more times to yield crystalline Form H. In a specific embodiment, the suspension is heated to 50° C. for a period of time (e.g., 30 minutes to 1 hour or 30 minutes to 5 hours) followed by slow cooling to 5° C. In a more specific embodiment, the cooling is at a rate of 0.1-0.5° C./min (e.g., 0.1° C./min).

In another aspect, the present invention provides crystalline Form J of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form J is characterized by at least three or at least four PXRD peaks at 2θ angles selected from 4.0°, 7.1°, 7.3°, 12.0° and 12.5°. In another embodiment, crystalline Form J is characterized by PXRD peaks at 2θ angles selected from 4.0°, 7.1°, 7.3°, 12.0° and 12.5°. In yet another embodiment, crystalline Form J is characterized by at least three, at least four, at least five, at least six, at least seven, at least eight, or at least nine PXRD peaks at 2θ angles selected from 4.0°, 6.0°, 7.1°, 7.3°, 10.5°, 12.0°, 12.5°, 15.1°, and 18.1°. In some embodiments, the peaks described in the above embodiments for crystalline Form J have a relative intensity of at least 1%, at least 2%, at least 5%, at least 10%, or at least 15%. In one embodiment, crystalline Form J has a PXRD pattern that is substantially the same as PXRD pattern shown in FIG. 14.

Figure 15:
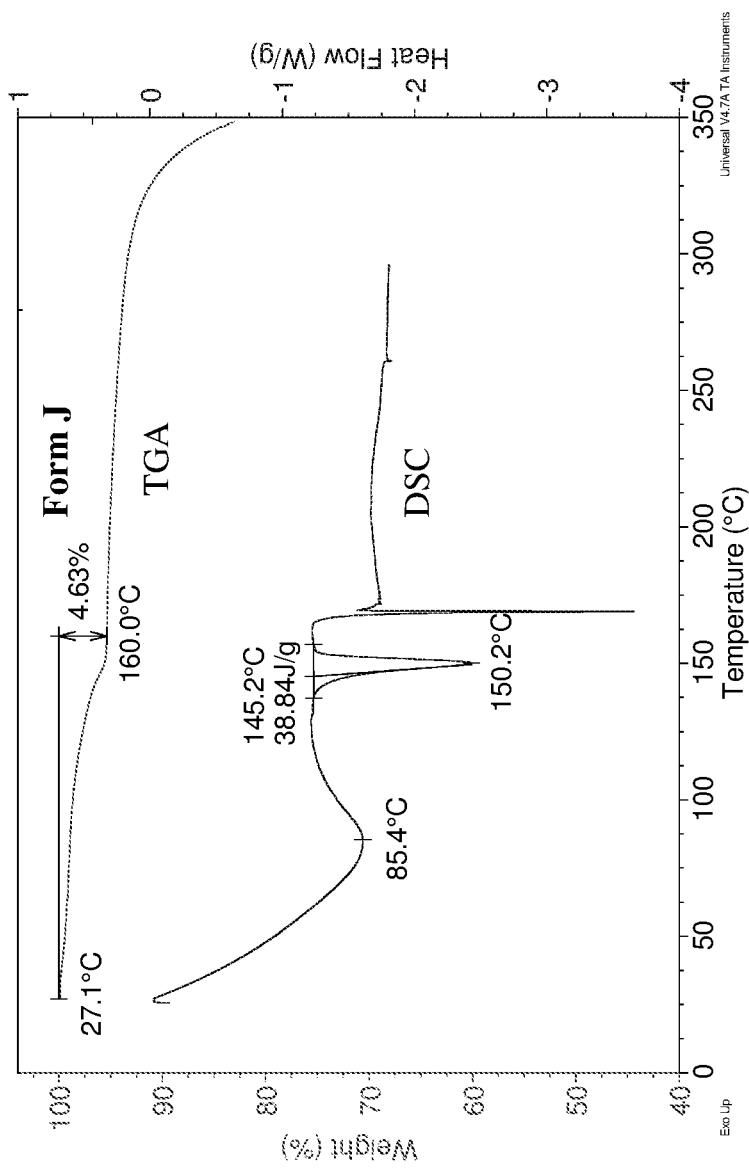
FIG. 15 depicts differential scanning calorimetry (DSC) and thermal gravimetric analysis (TGA) profiles of crystalline Form J of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another embodiment, crystalline Form J has a DSC profile that is substantially the same as DSC profile shown in FIG. 15. In particular, crystalline Form J is characterized by an onset temperature at 145.2° C.±2° C. in the DSC profile. In another embodiment, crystalline Form J has a melting temperature of 150.2° C.±2° C.

In another embodiment, crystalline Form J has a TGA profile that is substantially same as the TGA profile shown in FIG. 15. In particular, the TGA profile indicates that crystalline Form J is a hydrate or a hygroscopic anhydrate.

In some embodiments, crystalline Form J is characterized by, for example, DSC, TGA and PXRD. In one embodiment, crystalline Form J is characterized by PXRD alone or PXRD in combination with one or more of DSC and TGA described above In some embodiments, crystalline Form J is at least 70%, 80%, 85%, 90%, 95%, 97%, 99%, 99.5% or 99.9% pure. The purity of Form J is determined by dividing the weight of crystalline Form J in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form J of the compound.

In one aspect, the present invention provides a method for preparing crystalline Form J of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is fast evaporation crystallization method described herein. In a specific embodiment, crystalline Form J can be obtained by dissolving crystalline Form A in anisole followed by solvent evaporation at room temperature to yield crystalline Form J.

In yet another aspect, the present invention provides crystalline Form K of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form K is characterized by at least three, at least four or at least five PXRD peaks at 2θ angles selected from 5.7°, 8.0°, 8.7°, 9.7°, 12.0° and 18.0°. In another embodiment, crystalline Form K is characterized by PXRD peaks at 2θ angles selected from 5.7°, 8.0°, 8.7°, 9.7°, 12.0° and 18.0°. In yet another embodiment, crystalline Form K is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen or at least nineteen PXRD peaks at 2θ angles selected from 5.7°, 8.0°, 8.7°, 9.7°, 12.0°, 12.8°, 13.4°, 14.8°, 16.5°, 17.1°, 18.0°, 18.9°, 19.3°, 20.2°, 20.7°, 21.1°, 22.0°, 22.7° and 23.4°. In some embodiments, the peaks described in the above embodiments for crystalline Form K have a relative intensity of at least 1%, at least 2%, at least 5%, at least 10%, or at least 15%. In one embodiment, crystalline Form K has a PXRD pattern that is substantially the same as PXRD pattern shown in FIG. 16.

In some embodiments, crystalline Form K is at least 70%, 80%, 85%, 90%, 95%, 97%, 99%, 99.5% or 99.9% pure. The purity of Form K is determined by dividing the weight of crystalline Form K in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form K of the compound.

In one aspect, the present invention provides a method for preparing crystalline Form K of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method comprises heating crystalline Form A to 130° C. under an inert atmosphere (e.g., $N_2$).

In yet another aspect, the present invention provides crystalline Form L of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form L is characterized by at least three, at least four, at least five, at least six, at least seven or at least eight PXRD peaks at 2θ angles selected from 7.1°, 7.9°, 9.1°, 10.0°, 10.4°, 12.8°, 16.1°, 16.8° and 18.4°. In another embodiment, crystalline Form L is characterized by PXRD peaks at 2θ angles selected from 7.1°, 7.9°, 9.1°, 10.0°, 10.4°, 12.8°, 16.1°, 16.8° and 18.4°. In yet another embodiment, crystalline Form L is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen or at least nineteen PXRD peaks at 2θ angles selected from 7.1°, 7.9°, 9.1°, 10.0°, 10.4°, 12.8°, 14.6°, 15.1°, 16.1°, 16.8°, 18.4°, 19.1°, 20.2°, 20.8°, 21.5°, 22.8°, 23.8°, 24.9° and 26.9. In some embodiments, the peaks described in the above embodiments for crystalline Form L have a relative intensity of at least 1%, at least 2%, at least 5%, at least 10%, or at least 15%. In one embodiment, crystalline Form L has a PXRD pattern that is substantially the same as PXRD pattern shown in FIG. 17.

In some embodiments, crystalline Form L is at least 70%, 80%, 85%, 90%, 95%, 97%, 99%, 99.5% or 99.9% pure. The purity of Form L is determined by dividing the weight of crystalline Form L in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form L of the compound.

In an aspect, the present invention provides a method for preparing crystalline Form L of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method comprises heating crystalline Form C to 130° C. under an inert atmosphere (e.g., $N_2$).

In yet another aspect, the present invention provides crystalline Form M of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form M is characterized by at least three, at least four or at least five PXRD peaks at 2θ angles selected from 3.5°, 4.3°, 8.0°, 8.7°, 12.9° and 17.4°. In another embodiment, crystalline Form M is characterized by PXRD peaks at 2θ angles selected from 3.5°, 4.3°, 8.0°, 8.7°, 12.9° and 17.4°. In yet another embodiment, crystalline Form M is characterized by at least three, at least four, at least five, at least six, at least seven, at least eight, at least nine, at least ten, at least eleven, at least twelve, at least thirteen, at least fourteen or at least fifteen PXRD peaks at 2θ angles selected from 3.5°, 4.3°, 6.0°, 7.1°, 8.0°, 8.7°, 10.5°, 11.2°, 12.9°, 14.9°, 16.3°, 17.4°, 20.1°, 20.7° and 25.8°. In some embodiments, the peaks described in the above embodiments for crystalline Form M have a relative intensity of at least 1%, at least 2%, at least 5%, at least 10%, or at least 15%. In one embodiment, crystalline Form M has a PXRD pattern that is substantially the same as PXRD pattern shown in FIG. 18.

In some embodiments, crystalline Form M is at least 70%, 80%, 85%, 90%, 95%, 97%, 99%, 99.5% or 99.9% pure. The purity of Form M is determined by dividing the weight of crystalline Form M in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form M of the compound.

In an aspect, the present invention provides a method for preparing crystalline Form M of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is the slurry conversion crystallization method. In a particular embodiment, crystalline Form M is obtained by stirring the slurry of crystalline Form F or Form H in toluene for a period of time (e.g., 1 day, 2 days, 3 days, 4 days, 5 days, 1 week, 2 weeks, etc.) to yield crystalline Form M.

In one aspect, the present invention provides crystalline Form N of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form N is characterized by at least three, at least four, at least five, at least six or at least seven PXRD peaks at 2θ angles selected from 4.8°, 7.1°, 10.4°, 11.5°, 15.2°, 17.7°, 19.8° and 22.8°. In another embodiment, crystalline Form N is characterized by PXRD peaks at 2θ angles selected from 4.8°, 7.1°, 10.4°, 11.5°, 15.2°, 17.7°, 19.8° and 22.8°. In yet another embodiment, crystalline Form N is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three or at least twenty-four PXRD peaks at 2θ angles selected from 4.8°, 7.1°, 9.5°, 10.4°, 10.9°, 11.5°, 14.2°, 15.2°, 16.3°, 17.7°, 18.3°, 19.0°, 19.8°, 20.3°, 21.2°, 22.2°, 22.8°, 23.8°, 24.5°, 25.1°, 25.8°, 27.3°, 28.5° and 29.8°. In some embodiments, the peaks described in the above embodiments for crystalline Form N have a relative intensity of at least 1%, at least 2%, at least 5%, at least 10%, or at least 15%. In another embodiment, crystalline Form N has a PXRD pattern that is substantially the same as PXRD pattern shown in FIG. 19.

Figure 20:
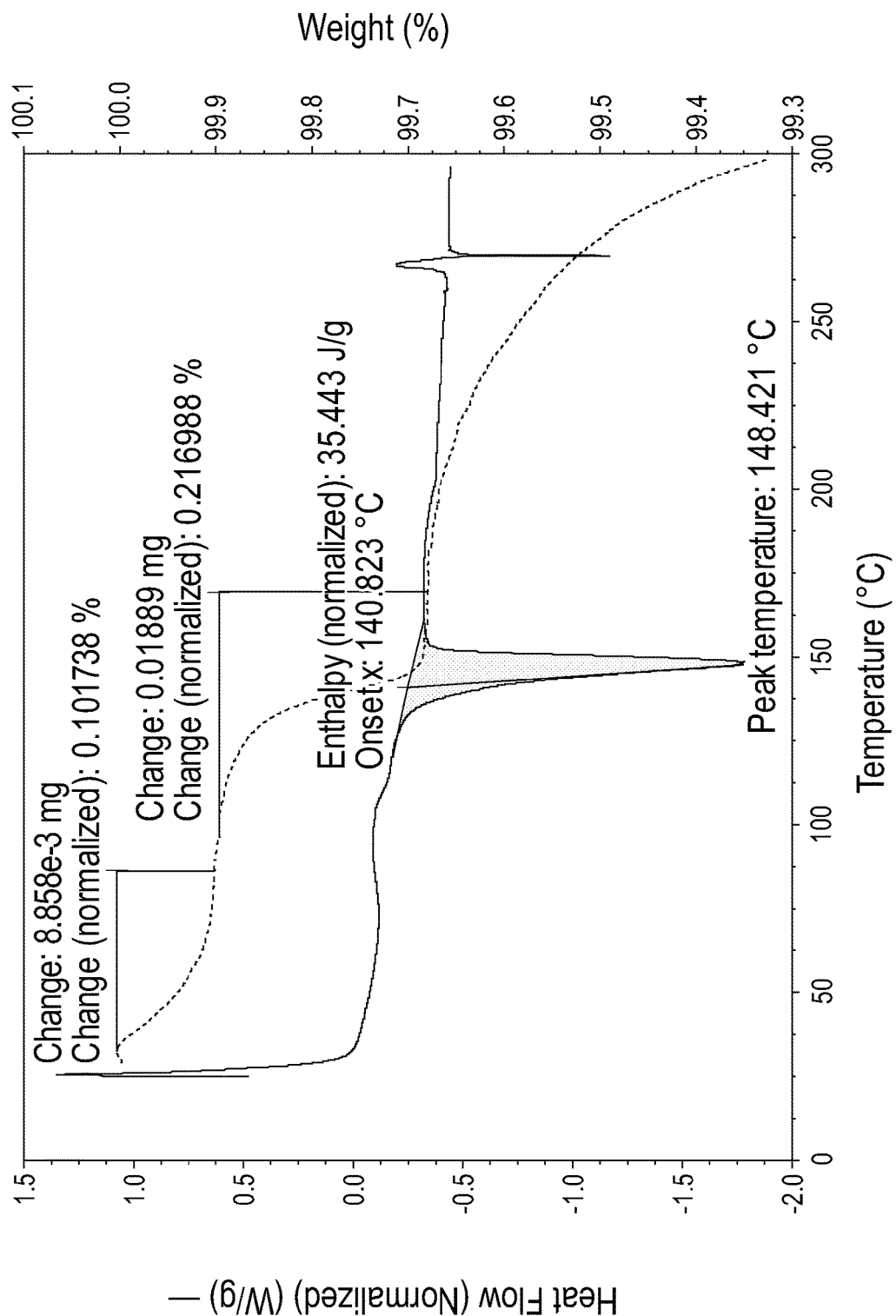
FIG. 20 depicts differential scanning calorimetry (DSC) and thermal gravimetric analysis (TGA) profiles of crystalline Form N of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form N has a DSC profile that is substantially the same as DSC profile shown in FIG. 20. In particular, crystalline Form N is characterized by an onset temperature at 140.8° C.±2° C. in the DSC profile. In another embodiment, crystalline Form N has a melting temperature of 148.4° C.±2° C.

In some embodiments, crystalline Form N is characterized by, for example, DSC and PXRD. In one embodiment, crystalline Form N is characterized by PXRD alone.

In some embodiments, crystalline Form N is at least 70%, 80%, 85%, 90%, 95%, 97%, 99%, 99.5% or 99.9% pure. The purity of Form N is determined by dividing the weight of crystalline Form N in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form N of the compound.

In an aspect, the present invention provides a method for preparing crystalline Form N of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method is anti-solvent crystallization method described herein. In a particular embodiment, the anti-solvent used is isopropyl acetate and the solvent is THF.

In yet another aspect, the present invention provides crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form P is characterized by at least three, at least four, at least five or at least six PXRD peaks at 2θ angles selected from 5.3°, 8.5°, 9.7°, 14.2°, 15.8°, 17.5° and 24.2°. In one embodiment, crystalline Form P is characterized by at least three, at least four or at least five PXRD peaks at 2θ angles selected from 5.3°, 9.7°, 14.2°, 15.8°, 17.5° and 24.2°. In another embodiment, crystalline Form P is characterized by at least three or at least four PXRD peaks at 2θ angles selected from 9.7°, 14.2°, 15.8°, 17.5° and 24.2°. In another embodiment, crystalline Form P is characterized by PXRD peaks at 2θ angles selected from 5.3°, 9.7°, 14.2°, 15.8°, 17.5° and 24.2°. In yet another embodiment, crystalline Form P is characterized by PXRD peaks at 2θ angles selected from 9.7°, 14.2°, 15.8°, 17.5° and 24.2°. In yet another embodiment, crystalline Form P is characterized by PXRD peaks at 2θ angles selected from 5.3°, 8.5°, 9.7°, 14.2°, 15.8°, 17.5° and 24.2°. In yet another embodiment, crystalline Form P is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, or at least twenty-three PXRD peaks at 2θ angles selected from 5.3°, 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5. In a specific embodiment, crystalline Form P is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, or at least twenty-two PXRD peaks at 2θ angles selected from 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5. In yet another specific embodiment, crystalline Form P is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, twenty-three or at least twenty-four PXRD peaks at 2θ angles selected from 5.3°, 8.5°, 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5. In some embodiments, the peaks described in the above embodiments for crystalline Form P have a relative intensity of at least 1%, at least 2%, at least 5%, at least 10%, or at least 15%. The relative intensity of the peaks listed above can vary based on the amount of water present in crystalline Form P. In a specific embodiment, the PXRD peaks at 2θ angles of 5.3° and/or 8.5° have higher relative intensity for Form P with less water content (e.g., anhydrate) than those with higher water content. In one embodiment, the peaks are specific for crystalline Form P anhydrate (e.g., at 8.5°). In yet another embodiment, the peaks are specific for crystalline Form P hydrate. In one embodiment, crystalline Form P has a PXRD pattern that is substantially the same as PXRD pattern shown in FIG. 21. In another embodiment, crystalline Form P has a PXRD pattern that is substantially the same as PXRD pattern shown in FIG. 23. In another embodiment, crystalline Form P has a PXRD pattern that is substantially the same as PXRD pattern shown in FIG. 24. In yet another embodiment, crystalline Form P has a PXRD pattern that is substantially the same as PXRD pattern shown in FIG. 26 or FIG. 27.

Figure 22:
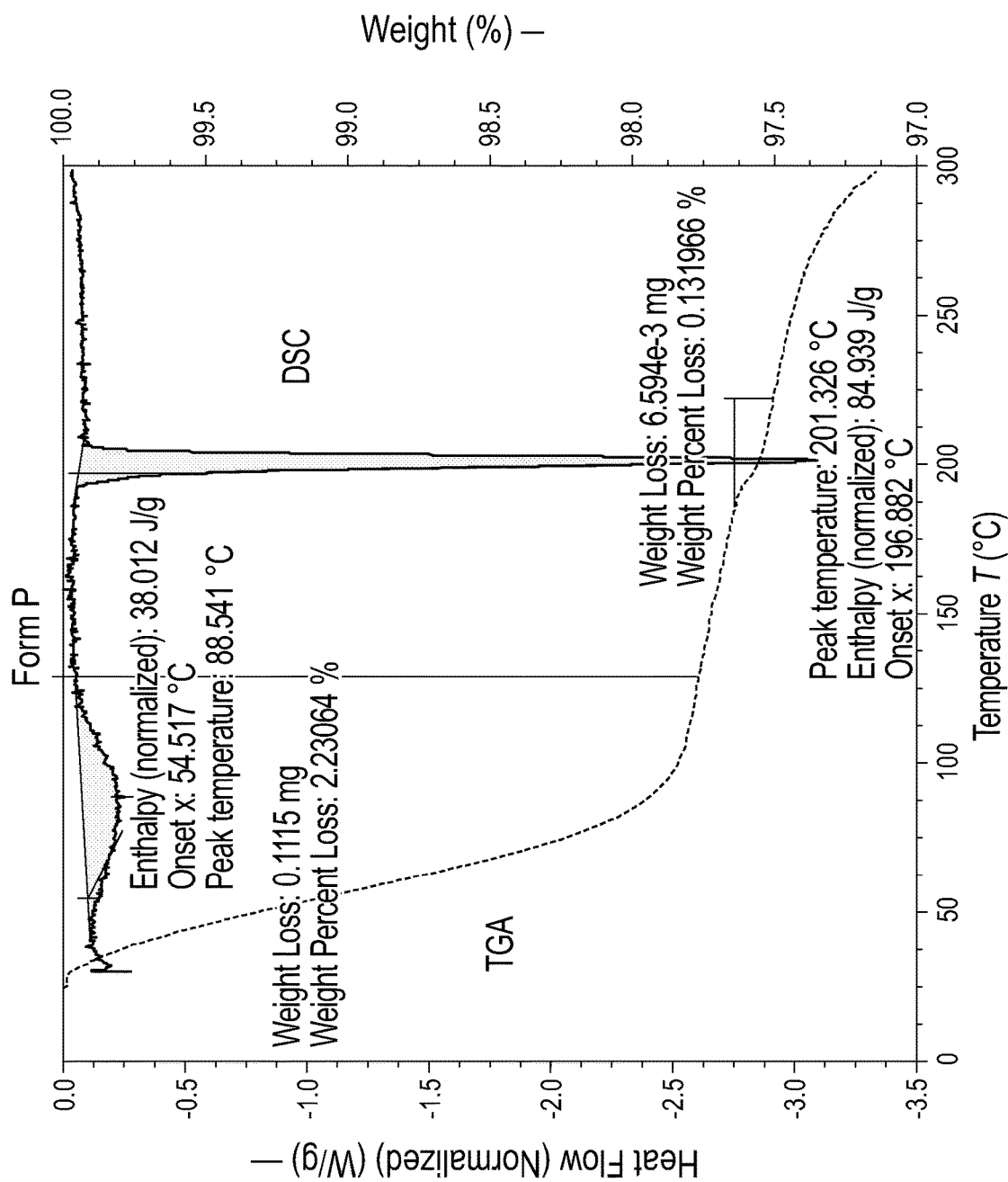
FIG. 22 depicts differential scanning calorimetry (DSC) and thermal gravimetric analysis (TGA) profiles of crystalline Form P of (R)-1-(tert-butyl)-N-(8-(24(1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.
Figure 25:
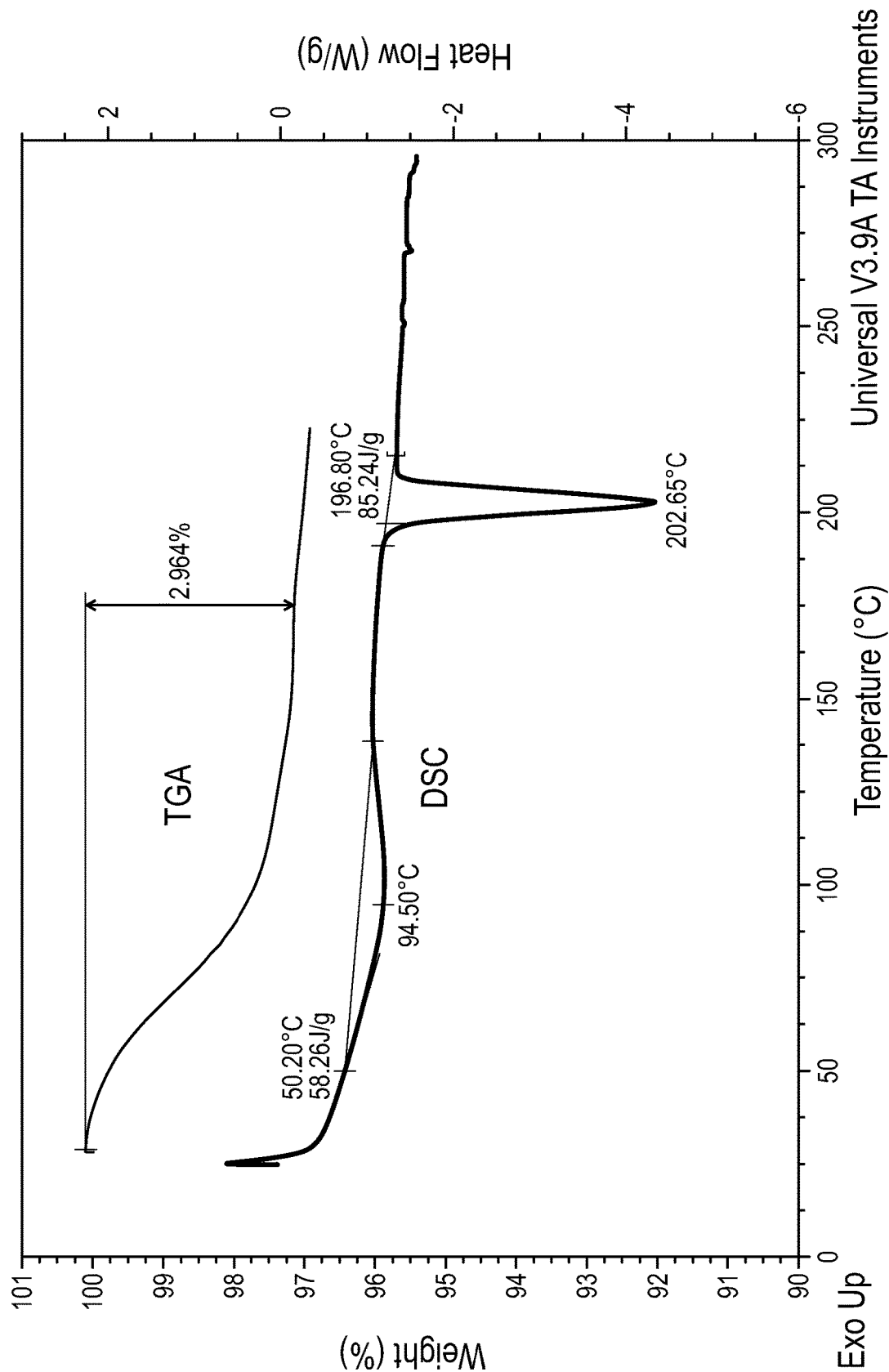
FIG. 25 depicts differential scanning calorimetry (DSC) and thermal gravimetric analysis (TGA) profiles of crystalline Form P of (R)-1-(tert-butyl)-N-(8-(24(1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide with 2.9 wt % water.

In one embodiment, crystalline Form P has a DSC profile that is substantially the same as DSC profile shown in FIG. 22 or FIG. 25. In particular, crystalline Form P is characterized by an onset temperature at 196.9° C.±2° C. in the DSC profile. In another embodiment, crystalline Form P has a melting temperature of 201.3° C.±2° C. In one embodiment, crystalline Form P has an additional broad peak at a temperature between 50° C. and 100° C., between 80° C. and 95° C. or between 85° C. and 95° C. The presence of the additional broad peak in the DSC profile indicates the presence of small amount of water in crystalline Form P.

In one embodiment, crystalline Form P can be an anhydrate, a hemihydrate or a monohydrate. In a specific embodiment, crystalline Form P is an anhydrate. In another specific embodiment, crystalline Form P is hemihydrate. In yet another specific embodiment, crystalline Form P is monohydrate.

In another embodiment, crystalline Form P may contain small amount of water. In a specific embodiment, crystalline Form P has between 0.1 wt % and 3.3 wt %, between 0.1 wt % and 1.5 wt %, between 0.1 wt % and 1.0 wt %, between 0.2 wt % and 0.6 wt %, between 1.5 wt % and 3.3 wt %, between 2.0 wt % and 3.3 wt %, between 2.5 wt % and 3.3 wt %, or between 2.5 wt % and 3.0 wt % of water. In another specific embodiment, crystalline Form P has 0.1 wt %, 0.2 wt %, 0.3 wt %, 0.4 wt %, 0.5 wt %, 0.6 wt %, 0.7 wt %, 0.8 wt %, 0.9 wt %, 1.0 wt %, 1.1 wt %, 1.2 wt %, 1.3 wt %, 1.4 wt %, 1.5 wt %, 1.6 wt %, 1.7 wt %, 1.8 wt %, 1.9 wt %, 2.0 wt %, 2.1 wt %, 2.2 wt %, 2.3 wt %, 2.4 wt %, 2.5 wt %, 2.6 wt %, 2.7 wt %, 2.8 wt %, 2.9 wt %, 3.0 wt %, 3.1 wt %, 3.2 wt %, 3.3 wt % of water. In yet another specific embodiment, crystalline Form P has 0.4 wt %, 0.5 wt %, 2.6 wt % or 2.9 wt % of water.

As used herein, "wt %" means percentage by weight.

In another embodiment, crystalline Form P has up to 1 molar equivalent of water. In a specific embodiment, crystalline Form P has 0.1, 0.2, 0.3, 0.4, 0.5, 0.6, 0.7, 0.8, 0.9 or 1 molar equivalent of water relative to the compound (R)-1-(tert-butyl)-N-(8-(24(1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In another embodiment, crystalline Form P has a TGA profile that is substantially same as the TGA profile shown in FIG. 22. In particular, the TGA profile indicates that crystalline Form P is a hydrate.

In yet another embodiment, crystalline Form P has a TGA profile that is substantially same as the TGA profile shown in FIG. 25.

In some embodiments, crystalline Form P is characterized by, for example, DSC, TGA and PXRD. In one embodiment, crystalline Form P is characterized by PXRD alone or PXRD in combination with one or more of DSC and TGA described above.

In some embodiments, crystalline Form P is at least 70%, 80%, 85%, 90%, 95%, 97%, 99%, 99.5% or 99.9% pure. The purity of Form P is determined by dividing the weight of crystalline Form P in a composition comprising compound (R)-1-(tert-butyl)-N-(8-(24(1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(24(1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form P of the compound.

In one aspect, the present invention provides a method for preparing crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method involves heating and stirring crystalline Form A or crystalline Form E in a mixture of DCM and propyl acetate (or a mixture of DCM and isopropyl acetate (IPAc) or a mixture of DCM and ethyl acetate (EtOAc)) at an elevated temperature (e.g., a temperature in the range of 50-95° C., 55-90° C., 60-90° C., 85-90° C. or at 90° C.) to yield crystalline Form P. In another embodiment, the method involves heating and stirring crystalline Form A or crystalline Form E in a mixture of DCM and IPAc in the presence of water (e.g., ≥200 ppm) at an elevated temperature (e.g., in the range of 65-90° C., 80-95° C. or 85-90° C., or 85-88° C.), followed by slow cooling to a temperature in the range of 10-25° C. or 15-20° C. In a specific embodiment, the method further comprises the step of cooling the mixture to a temperature in the range of 60-80° C., 60-75° C. or 65-70° C. and stirring the mixture for a time period (e.g., 5 to 15 hours, 5 to 10 hours, 5 hours, 6 hours, 7 hours, 8 hours, 9 hours, 10 hours, 11 hours, 12 hours, 13 hours, 14 hours or 15 hours) before cooling the mixture to a temperature in the range of 10-25° C. or 15-20° C.

In yet another aspect, the present invention provides crystalline Form Q of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

In one embodiment, crystalline Form Q is characterized by at least three, at least four, at least five, at least six or at least seven PXRD peaks at 2θ angles selected from 5.2°, 8.5°, 9.6°, 10.5°, 14.0°, 15.7° and 17.3°. In another embodiment, crystalline Form Q is characterized by PXRD peaks at 2θ angles selected from 5.2°, 8.5°, 9.6°, 10.5°, 14.0°, 15.7° and 17.3°. In yet another embodiment, crystalline Form Q is characterized by at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one or at least twenty-two PXRD peaks at 2θ angles selected from 5.2°, 8.5°, 9.6°, 10.5°, 11.3°, 12.3°, 14.0°, 15.7°, 17.3°, 17.8°, 17.9°, 19.3°, 19.9°, 20.3°, 21.5°, 22.4°, 23.0°, 23.9°, 24.4°, 25.2°, 26.1° and 27.5°. In some embodiments, the peaks described in the above embodiments for crystalline Form Q have a relative intensity of at least 1%, at least 2%, at least 5%, at least 10%, or at least 15%. In one embodiment, crystalline Form Q has a PXRD pattern that is substantially the same as PXRD pattern shown in FIG. 28.

In some embodiments, crystalline Form Q is at least 70%, 80%, 85%, 90%, 95%, 97%, 99%, 99.5% or 99.9% pure. The purity of Form Q is determined by dividing the weight of crystalline Form Q in a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide over the total weight of the compound in the composition. In one embodiment, the present invention provides a composition comprising compound (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide, wherein at least 70%, 80%, 85%, 90%, 95%, 97%, 99%, 99.5% or 99.9% by weight of the compound in the composition is crystalline Form Q of the compound.

In an aspect, the present invention provides a method for preparing crystalline Form Q of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide. In one embodiment, the method comprises heating crystalline Form P to 150° C. or drying the sample at less than 5% relative humidity for several hours (e.g., 1 hour, 2 hours, 5 hours, 10 hours, 15 hours, etc.).

It will be understood that the 2θ values of the PXRD pattern for crystalline Form B, C, D, E, F, H, J, K, L, M, N, P or Q may vary slightly from one instrument to another and may depend on variations in sample preparation. Therefore, the PXRD peak positions for these crystalline Forms are not to be construed as absolute and can vary±0.2°.

As intended herein, "substantially the same PXRD pattern as shown in FIG. x" mean that for comparison purposes, at least 80%, at least 90%, or at least 95% of the peaks shown in FIG. x are present. FIG. x is FIG. 1, FIG. 3, FIG. 5, FIG. 8, FIG. 10, FIG. 12, FIG. 14, FIG. 16, FIG. 17, FIG. 18, FIG. 19, FIG. 21, FIG. 23, FIG. 24, FIG. 26, FIG. 27 or FIG. 28. It is to be further understood that for comparison purposes some variability in peak position from those shown in FIG. x are allowed, such as ±0.2°. Similarly, for comparison purposes some variability in peak position from those shown in DSC and TGA profiles as well as NMR spectrum described herein are allowed. For example, the peak positions can vary from those shown in FIG. 7, such as ±0.5 ppm. The onset temperature and/or melting temperature can vary from those shown FIG. 2A, FIG. 4A, FIG. 6, FIG. 9, FIG. 11, FIG. 13A, FIG. 15, FIG. 20, FIG. 22, or FIG. 25, such as ±2° C.

In one aspect, the present invention provides a pharmaceutical composition comprising a crystalline Form described herein, e.g., crystalline Form B, C, D, E, F, H, J, K, L, M, N, P or Q, and a pharmaceutically acceptable excipient.

Another aspect of the invention provides a method of treating a disorder responsive to inhibition of Bruton's tyrosine kinase in a subject comprising administering to the subject an effective amount of crystalline Form B, C, D, E, F, H, J, K, L, M, N, P or Q or a composition (e.g., pharmaceutical composition) comprising crystalline Form B, C, D, E, F, H, J, K, L, M, N, P or Q.

In some embodiments of the above disclosed aspect, the disorder is an autoimmune disorder. In some additional embodiments of the above disclosed aspect, the autoimmune disorder is multiple sclerosis.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 µg-500 mg.

Administering a compound described herein to a mammal comprises any suitable delivery method. Administering a compound described herein to a mammal includes administering a compound described herein topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein.

Thus, a compound described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds described herein can be dissolved or dispersed at effective levels, optionally with the aid of non-toxic surfactants.

Useful dosages of a compound described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound described herein and instructional material which can describe administering a compound described herein or a composition comprising a compound described herein to a cell or a subject. This should be construed to include other embodiments of kits that are known to those skilled in the art, such as a kit comprising a (such as sterile) solvent for dissolving or suspending a compound described herein or composition prior to administering a compound described herein or composition to a cell or a subject. In some embodiments, the subject can be a human.

EXEMPLIFICATIONS

Powder X-Ray Diffraction

Crystallinity of the compound was studied using a XRD-D8 X-ray powder diffractometer using Cu Kα radiation (Bruker, Madison, Wis.). The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a Lynxeye detector. A θ-2θ continuous scan at 1.6°/min from 3 to 42° 2θ was used. The sample was prepared for analysis by placing it on a zero background plate.

Differential Scanning Calorimetry (DSC) and Thermogravimetric Analysis (TGA)

Thermal properties of the compound were examined using a Discovery Differential Scanning calorimeter (DSC) (TA Instruments) and a Discovery Thermogravimetric Analyzer (TGA) (TA Instruments). Sample was enclosed in a closed aluminum DSC pan for DSC analysis and in an open aluminum pan for TGA analysis. The thermal analysis was performed with a linear gradient from 25° C. to 300° C. at 10° C. per minute for both DSC and TGA studies.

Example 1

Preparation of Crystalline Form A

1. Preparation of 3-(3-Bromo-benzylamino)-propionic acid ethyl ester

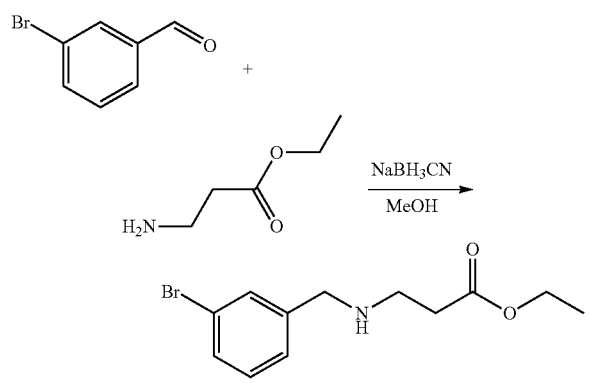

To a solution of ethyl 3-aminopropanoate (46.0 g, 0.3 mol) and 3-bromobenzaldehyde (55.5 g, 0.3 mol) in MeOH (1.2 L) were added triethylamine (60.7 g, 0.6 mol) and NaCNBH$_3$ (56.5 g, 0.9 mol) portion-wise. The resulting mixture was stirred at rt for 4 h. The reaction mixture was concentrated in vacuo and the residue was diluted with water (600 mL). The mixture was extracted with EtOAc (3×500 mL). The combined organic layer was washed with brine (100 mL), dried over anhydrous Na$_2$SO$_4$, filtered and concentrated in vacuo to give 3-(3-bromo-benzylamino)-propionic acid ethyl ester (46.5 g, yield: 54%) as a light yellow oil. $^1$H NMR (DMSO-d$_6$, 300 MHz): δ 7.52 (s, 1H), 7.40 (d, J=7.5 Hz, 1H), 7.31-7.25 (m, 2H), 4.04 (q, J=7.2 Hz, 2H), 3.67 (s, 2H), 2.69 (t, J=7.2 Hz, 2H), 2.42 (t, J=6.9 Hz, 2H), 1.17 (t, J=6.9 Hz, 3H).

2. Preparation of 3-[(3-Bromo-benzyl)-(toluene-4-sulfonyl)-amino]-propionic acid ethyl ester

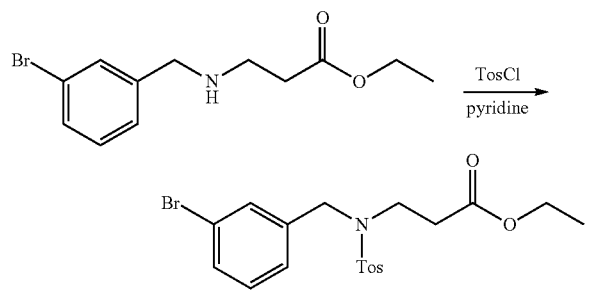

To a solution of 3-(3-bromo-benzylamino)-propionic acid ethyl ester (45.6 g, 0.16 mol) in pyridine (500 mL) was added TosCl (61.0 g, 0.32 mol) at rt. The reaction mixture was stirred at 120° C. for 16 h. The solvent was removed in vacuo to give the crude product. The crude product was purified by column chromatography on silica gel (petroleum ether:EtOAc=10:1 to 5:1) to afford 3-[(3-Bromo-benzyl)-(toluene-4-sulfonyl)-amino]-propionic acid ethyl ester (61 g, yield: 88%) as a light yellow oil. $^1$H NMR (DMSO-d$_6$, 300 MHz): δ 7.74 (d, J=8.4 Hz, 2H), 7.49-7.41 (m, 4H), 7.31 (d, J=5.1 Hz, 2H), 4.33 (s, 2H), 3.93 (q, J=7.2 Hz, 2H), 3.32 (t, J=7.2 Hz, 2H), 2.41 (s, 3H), 2.36 (t, J=6.9 Hz, 2H), 1.10 (t, J=6.9 Hz, 3H).

3. Preparation of 3-[(3-Bromo-benzyl)-(toluene-4-sulfonyl)-amino]-propionic acid

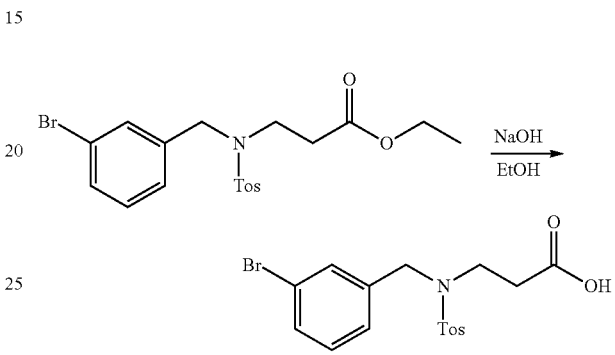

To a solution of 3-[(3-Bromo-benzyl)-(toluene-4-sulfonyl)-amino]-propionic acid ethyl ester (60.0 g, 0.14 mol) in a mixed solvent of EtOH (600 mL) and H$_2$O (60 mL) was added NaOH (11.2 g, 0.28 mol) portion-wise, the reaction solution was stirred at 60° C. for 4 h. The reaction solution was cooled to 0° C. and acidified to pH=5 with concentrated HCl. The solvent was concentrated in vacuo to give a residue which was extracted with EtOAc (3×150 mL). The organic layer was dried with Na$_2$SO$_4$, filtered, and concentrated in vacuo to give 3-[(3-Bromo-benzyl)-(toluene-4-sulfonyl)-amino]-propionic acid (45.2 g, yield: 78.6%) as a white solid. $^1$H NMR (DMSO-d$_6$, 300 MHz): δ 12.28 (br, 1H), 7.74 (d, J=8.1 Hz, 2H), 7.49-7.41 (m, 4H), 7.32 (d, J=5.1 Hz, 2H), 4.33 (s, 2H), 3.29 (t, J=6.9 Hz, 2H), 2.41 (s, 3H), 2.27 (t, J=7.5 Hz, 2H).

4. Preparation of 3-[(3-Bromo-benzyl)-(toluene-4-sulfonyl)-amino]-propionyl chloride

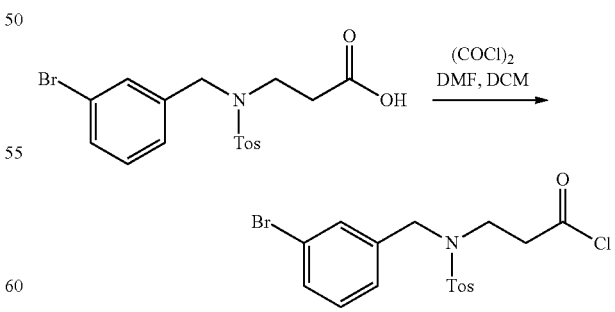

To a solution of 3-[(3-Bromo-benzyl)-(toluene-4-sulfonyl)-amino]-propionic acid (45.2 g, 0.11 mol) in CH$_2$Cl$_2$ (1000 mL) were added dropwise DMF (1 mL) and oxalyl chloride (27.9 g, 0.22 mol) portion-wise. The reaction solution was stirred at 55° C. for 2 h. The mixture was concentrated in vacuo to give the crude 3-[(3-Bromo-benzyl)-(toluene-4-sulfonyl)-amino]-propionyl chloride (47.2 g, yield: 99%) as a black oil which was used in the next step without further purification.

5. Preparation of 8-Bromo-2-(toluene-4-sulfonyl)-1,2,3,4-tetrahydro-benzo[c]azepin-5-one

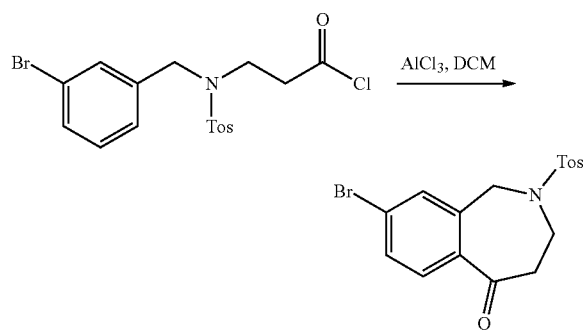

To a solution of 3-[(3-Bromo-benzyl)-(toluene-4-sulfonyl)-amino]-propionyl chloride (47.0 g, 0.11 mol) in anhydrous $CH_2Cl_2$ (1200 mL) was added $AlCl_3$ (29.3 g, 0.22 mol) portion-wise at rt. The reaction mixture was stirred at 55° C. for 2 h. The reaction mixture was poured into ice water (1.2 L) and extracted with (500 mL). The organic layer was concentrated in vacuo to give the crude product. The crude product was purified by column chromatography on silica gel (petroleum ether:EtOAc=5:1 to 2:1) to afford 8-bromo-2-(toluene-4-sulfonyl)-1,2,3,4-tetrahydro-benzo[c]azepin-5-one (35 g, yield: 81%) as a white solid. $^1$H NMR (DMSO-$d_6$, 300 MHz): δ 7.65 (d, J=8.4 Hz, 3H), 7.60-7.51 (m, 2H), 7.36 (d, J=8.1 Hz, 2H), 4.68 (s, 2H), 3.42 (t, J=9.2 Hz, 2H), 2.96 (t, J=6.3 Hz, 2H), 2.37 (s, 3H).

6. Preparation of [8-Bromo-2-(toluene-4-sulfonyl)-2,3,4,5-tetrahydro-1H-benzo[c]azepin-5-yl]-carbamic acid tert-butyl ester

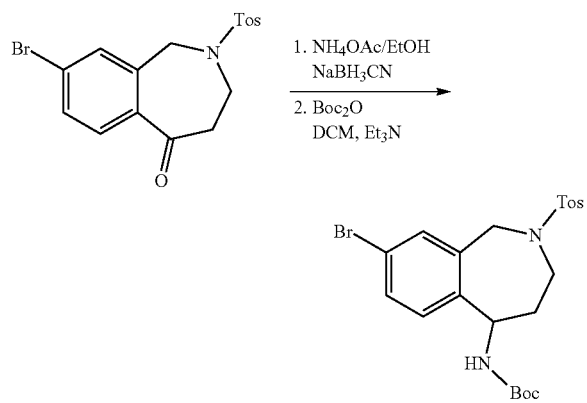

To a solution of 8-bromo-2-(toluene-4-sulfonyl)-1,2,3,4-tetrahydro-benzo[c]azepin-5-one (32.0 g, 0.08 mol) in EtOH (600 mL) were added $NH_4OAc$ (18.5 g, 0.24 mol) and $NaCNBH_3$ (14.9 g, 0.24 mol) portion-wise at rt. Then the reaction mixture was stirred at 95° C. for 16 h. The mixture was poured into ice water (500 mL) and then EtOH was removed in vacuo. The residue was extracted with $CH_2Cl_2$ (3×500 mL). The combined solvent was concentrated. The residue was redissolved in $CH_2Cl_2$ (300 mL) and were added triethylamine (12.2 g, 0.12 mol) and $(Boc)_2O$ (34.6 g, 0.12 mol) at rt. The mixture was stirred at rt for 4 h and then concentrated in vacuo to give the crude product. The crude product was purified by column chromatography on silica gel (peteroleum ether:EtOAc=8:1 to 2:1) to afford [8-bromo-2-(toluene-4-sulfonyl)-2,3,4,5-tetrahydro-1H-benzo[c]azepin-5-yl]-carbamic acid tert-butyl ester (16.7 g, yield: 42%) as a white solid. $^1$H NMR (DMSO $d_6$, 300 MHz): δ 7.62-7.51 (m, 2H), 7.47 (d, J=9.9 Hz, 1H), 7.41-7.34 (m, 3H), 7.10 (d, J=8.4 Hz, 1H), 4.81-4.74 (m, 1H), 4.53 (d, J=15.0 Hz, 1H), 4.28 (d, J=15.3 Hz, 1H), 3.64-3.57 (m, 1H), 3.41-3.30 (m, 1H), 2.35 (s, 3H), 1.85-1.77 (m, 1H), 1.69-1.63 (m, 1H), 1.36 (s, 9H).

7. Preparation of 8-Bromo-2-(toluene-4-sulfonyl)-2,3,4,5-tetrahydro-1H-benzo[c]azepin-5-ylamine

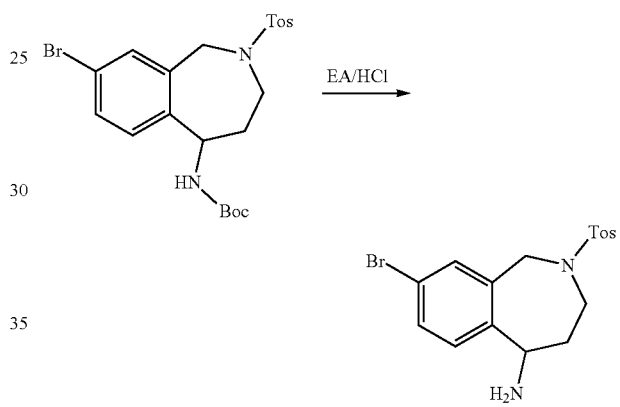

A solution of [8-bromo-2-(toluene-4-sulfonyl)-2,3,4,5-tetrahydro-1H-benzo[c]azepin-5-yl]-carbamic acid tert-butyl ester (14.8 g, 0.03 mol) in HCl/EtOAc (150 mL) was stirred at 25° C. for 4 h. The resulting solid was filtered and washed with MeOH and $Et_2O$ to give the product 8-bromo-2-(toluene-4-sulfonyl)-2,3,4,5-tetrahydro-1H-benzo[c]azepin-5-ylamine (10.5 g, yield: 89%) as a white solid. $^1$H NMR (DMSO-$d_6$, 300 MHz): δ 8.79 (br, 3H), 7.64-7.58 (m, 3H), 7.53 (s, 1H), 7.36 (d, J=8.4 Hz, 2H), 7.15 (d, J=8.4 Hz, 1H), 4.71-4.61 (m, 2H), 4.31 (d, J=15.3 Hz, 1H), 3.82 (d, J=18.3 Hz, 1H), 2.38 (s, 3H), 2.14-2.07 (m, 1H), 1.77-1.71 (m, 1H). LC-MS: m/z 395.0/397.0 [M+H]$^+$.

8. Synthesis of 8-bromo-2,3,4,5-tetrahydro-1H-benzo[c]azepin-5-amine

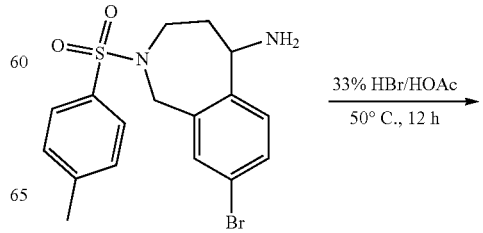

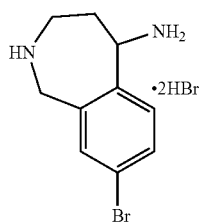

A solution of 8-bromo-2-(toluene-4-sulfonyl)-2,3,4,5-tetrahydro-1H-benzo[c]azepin-5-ylamine (2.00 g, 5.06 mmol) in HBr (33% solution in acetic acid, 20 mL) was heated at 50° C. for 12 h. After cooling to rt, the mixture was diluted EtOAc (50 mL). The white solid was collected by filtration and dried in vacuo to afford crude product 8-bromo-2,3,4,5-tetrahydro-1H-benzo[c]azepin-5-amine (1.66 g, yield: 82%), which was used directly in the next step. ESI-MS $(M+H)^+$ 241.1. $^1$H NMR (400 MHz, $CD_3OD$) δ: 7.72-7.55 (m, 2H), 7.18 (d, J=8.4 Hz, 1H), 4.99-4.98 (m, 1H), 4.51 (d, J=14.4 Hz, 1H), 4.39 (d, J=14.4 Hz, 1H), 3.62-3.49 (m, 2H), 2.38-2.24 (m, 1H), 2.16-2.00 (m, 1H).

9. Synthesis of tert-butyl 5-amino-8-bromo-4,5-dihydro-1H-benzo[c]azepine-2(3H)-carboxylate

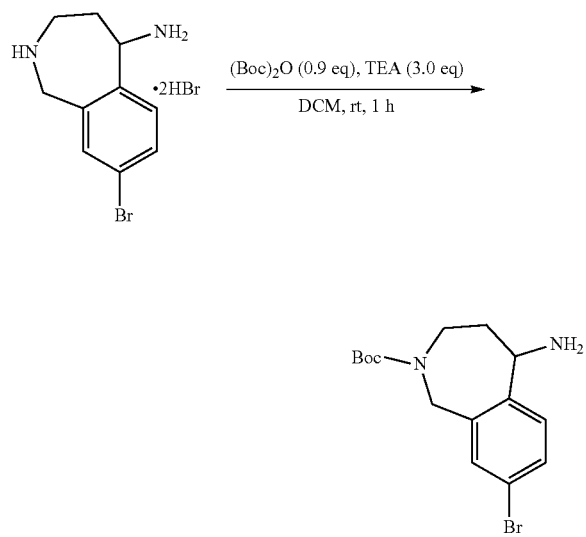

To a solution of 8-bromo-2,3,4,5-tetrahydro-1H-benzo[c]azepin-5-amine (640 mg, 1.60 mmol) and triethylamine (490 mg, 4.8 mmol) in $CH_2Cl_2$ (20 mL) was added $(Boc)_2O$ (314 mg, 1.44 mmol). The mixture was stirred at rt for 1 h. After diluting with $CH_2Cl_2$ (100 mL), the mixture was washed with brine (20 mL×2). The organic phase was concentrated in vacuo and the residue was purified by prep-HPLC ($CH_3CN/H_2O$ with 0.05% $NH_3 \cdot H_2O$ as mobile phase) to give tert-butyl 5-amino-8-bromo-4,5-dihydro-1H-benzo[c]azepine-2(3H)-carboxylate as a colorless oil (364 mg, yield: 67%). ESI-MS $(M+H)^+$: 341.1.

10. Chiral resolution of tert-butyl 5-amino-8-bromo-4,5-dihydro-1H-benzo[c]azepine-2(3H)-carboxylate to give tert-butyl (R)-5-amino-8-bromo-1,3,4,5-tetrahydro-2H-benzo[c]azepine-2-carboxylate compound with (11bS)-4-hydroxydinaphtho[2,1-d:1',2'-f][1,3,2]dioxaphosphepine 4-oxide (1:1)

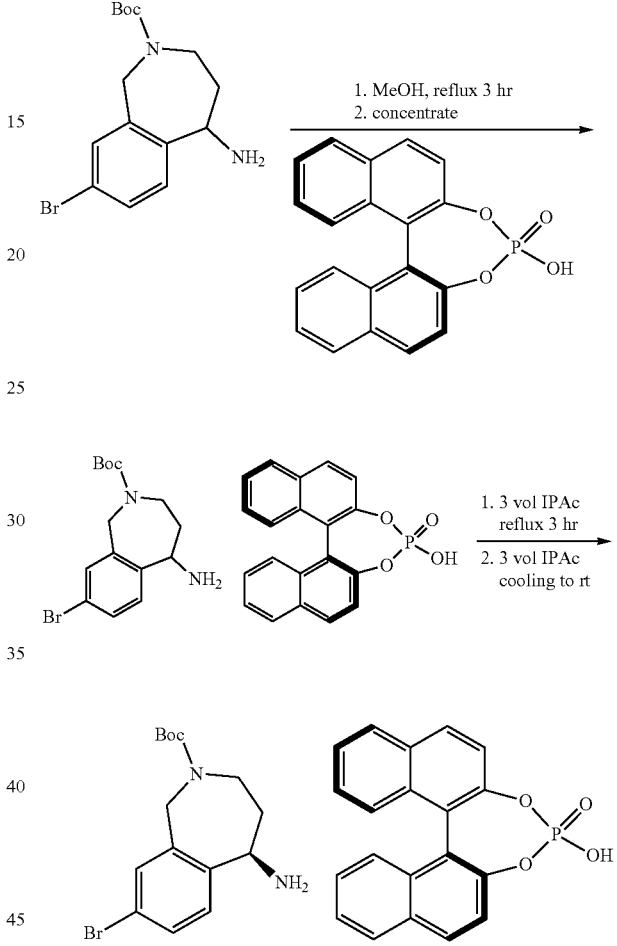

To tert-butyl 5-amino-8-bromo-4,5-dihydro-1H-benzo[c]azepine-2(3H)-carboxylate (800 g, 2.34 mol) was added MeOH (4.8 L) and (S)-(−)-1,1'-binaphthyl-2,2'-diylhydrogenphosphate (816.6 g, 2.34 mol). The mixture was stirred at 25° C. for 30 min and formed a yellow slurry. The slurry was stirred at reflux (70° C.) to give a yellow solution. The mixture was concentrated to dryness and IPAc (3.44 L) was added. The mixture was heated to 70° C. and was stirred at that temperature for 3 h. The reaction mixture was cooled to room temperature and an additional portion of IPAc (3.44 L) was added. The reaction mixture continued to stir at room temperature for 16 h. The slurry was filtered on centrifuge and the cake was washed three times, each with 7 vol IPAc. The wet cake was briefly dried to give tert-butyl (R)-5-amino-8-bromo-1,3,4,5-tetrahydro-2H-benzo[c]azepine-2-carboxylate compound with (11bS)-4-hydroxydinaphtho[2,1-d:1',2'-f][1,3,2]dioxaphosphepine 4-oxide (1:1) (515 g. yield: 64% [assuming maximum recovery of 50%], 91.3% ee) as a white solid. The recrystallization process can be repeated to increase the ee to 97.2%.

11. Synthesis of tert-butyl (R)-8-bromo-5-(1-(tert-butyl)-1H-1,2,3-triazole-4-carboxamido)-1,3,4,5-tetrahydro-2H-benzo[c]azepine-2-carboxylate

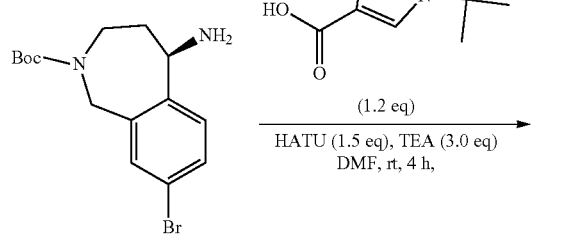

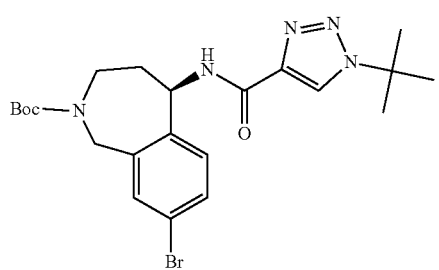

To solution of 5-(tert-butyl)-1,3,4-oxadiazole-2-carboxylate (1.2 eq) and HATU (1.5 eq) in DMF (20 mL) were added triethylamine (3.0 eq) and tert-butyl 5-amino-8-bromo-4,5-dihydro-1H-benzo[c]azepine-2(3H)-carboxylate (1 eq). The mixture was stirred at rt for 4 h. The crude product was purified by silica gel column chromatography (EtOAc/petroleum ether=1:2) to give tert-butyl (R)-8-bromo-5-(1-(tert-butyl)-1H-1,2,3-triazole-4-carboxamido)-1,3,4,5-tetrahydro-2H-benzo[c]azepine-2-carboxylate as yellow solid (2.3 g, yield: 95%). ESI-MS (M+H)+: 492.2.

12. Synthesis of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate

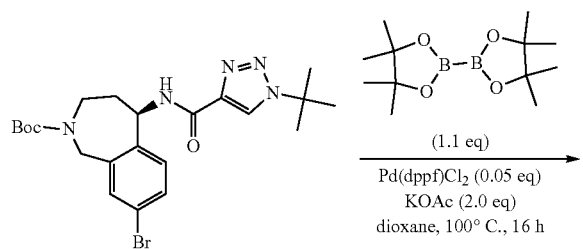

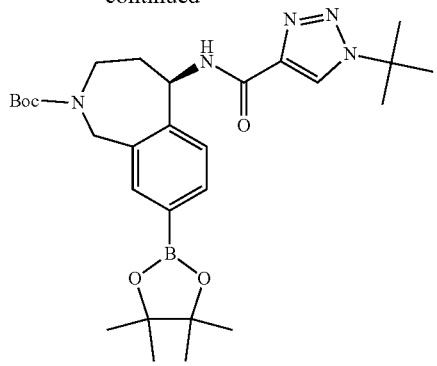

A mixture of tert-butyl (R)-8-bromo-5-(1-(tert-butyl)-1H-1,2,3-triazole-4-carboxamido)-1,3,4,5-tetrahydro-2H-benzo[c]azepine-2-carboxylate (1 eq), 4,4,4',4',5,5,5',5'-octamethyl-2,2'-bi(1,3,2-dioxaborolane) (1.1 eq), KOAc (2.0 eq) and Pd(dppf)Cl$_2$·DCM (0.05 eq) in 1,4-dioxane was stirred at 100° C. for 16 h under nitrogen. After cooling to room temperature, the mixture was diluted with EtOAc, washed with water, dried with Na$_2$SO$_4$ and concentrated to give tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate. The crude product was used for next step without purification. ESI-MS (M+H)+: 540.3.

13. Synthesis of tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate

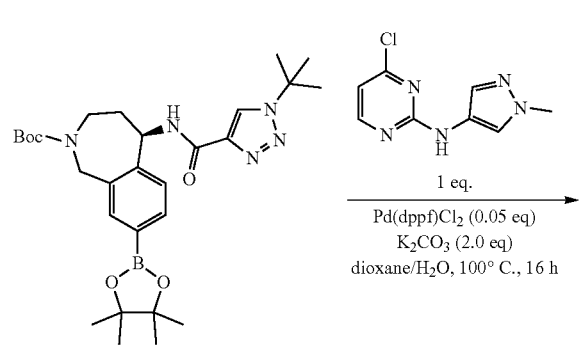

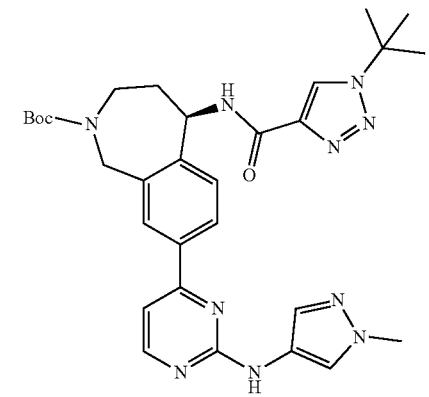

To a solution of tert-butyl (R)-5-(1-(tert-butyl)-1H-1,2,3-triazole-4-carboxamido)-8-(4,4,5,5-tetramethyl-1,3,2-dioxaborolan-2-yl)-1,3,4,5-tetrahydro-2H-benzo[c]azepine-2-carboxylate (5.4 g, 10.0 mmol) in dioxane/H₂O (100 mL) was added 4-chloro-N-(1-methyl-1H-pyrazol-4-yl)pyrimidin-2-amine (2.1 g, 10.0 mmol), K₂CO₃ (2.8 g, 20.0 mmol) and Pd(dppf)Cl₂ (0.4 g, 0.5 mmol) were added. The mixture was stirred at 100° C. for 16 h under nitrogen. After cooling to rt, the mixture was concentrated and purified by silica gel column chromatography (petroleum ether/EtOAc=1:3) to give tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate as a yellow solid (3.2 g, yield: 55%). ESI-MS (M+H)⁺: 586.7. ¹H NMR (400 MHz, CDCl₃) δ: 8.42 (s, 1H), 8.19 (s, 1H), 8.02-7.87 (m, 3H), 7.68 (s, 1H), 7.54-7.49 (m, 2H), 7.06 (d, J=5.2 Hz, 1H), 5.63-5.58 (m, 1H), 4.83-4.67 (m, 1H), 4.51-4.47 (m, 1H), 4.02-4.00 (m, 1H), 3.93 (s, 3H), 3.65-3.62 (m, 1H), 2.14-2.12 (m, 2H), 1.72 (s, 9H), 1.41-1.38 (m, 9H).

14. Synthesis of (R)-1-(tert-butyl)-N-(8-(24(1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide

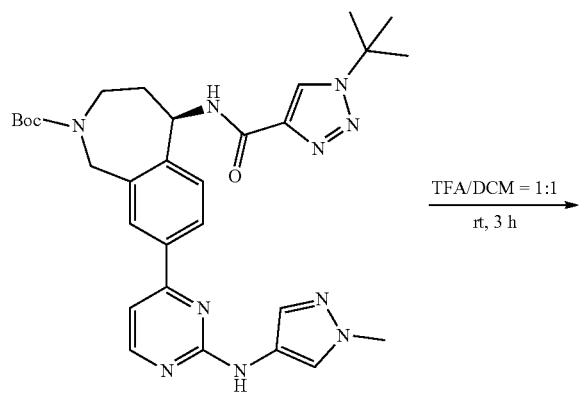

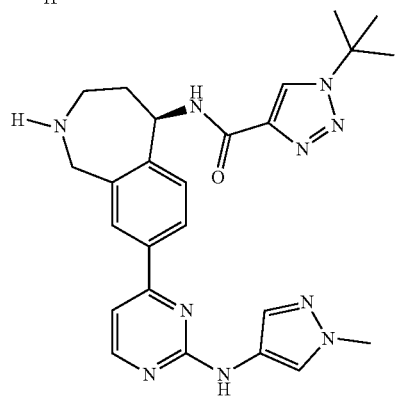

To a solution of tert-butyl (R)-5-(1-(tert-butyl)-1H-1,2,3-triazole-4-carboxamido)-8-(2-((1-methyl-1H-pyrazol-4-yl)amino)pyrimidin-4-yl)-1,3,4,5-tetrahydro-2H-benzo[c]azepine-2-carboxylate (3.2 g, 5.5 mmol) in DCM (30 mL) was added TFA (30 mL). The mixture was stirred at rt for 3 h. The solvent was removed. The crude was dissolved in MeOH (30 mL)/water (20 mL). The mixture was basified with NH₄OH to pH=8-9 and extracted with DCM (3×50 mL). The combined organic layers were washed with brine, dried over Na₂SO₄, filtered and concentrated to give (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide as a gray solid (2.6 g, yield: 98%). ESI-MS (M+H)⁺: 486.7.

15. Synthesis of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide

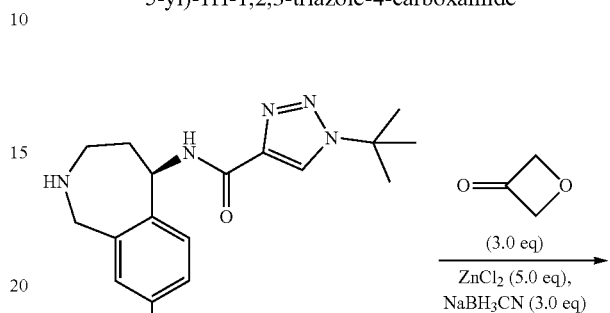

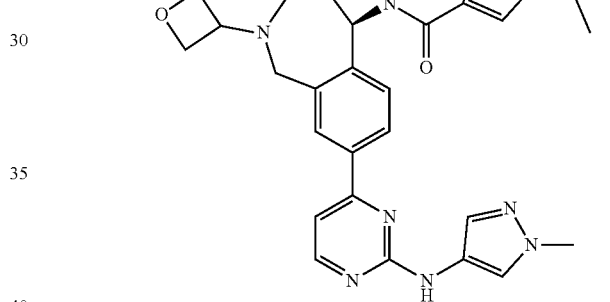

To a solution of (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (500 mg, 1.0 mmol) in MeOH (30 mL) were added oxetan-3-one (216 mg, 3.0 mmol), ZnCl₂ (682 mg, 5.0 mmol) and NaBH₃CN (189 mg, 3.0 mmol). The mixture was stirred at 50° C. for 3 h. The mixture was concentrated and the crude material was purified by silica gel chromatography (CH₂Cl₂:MeOH grading from 20:1 to 15:1) to give (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide as a yellow solid (307 mg, yield: 55%). ESI-MS (M+H)⁺: 542.7. ¹H NMR (400 MHz, CD₃OD) δ: 8.54 (s, 1H), 8.42 (d, J=5.6 Hz, 1H), 8.04-7.98 (m, 3H), 7.71 (s, 1H), 7.49 (d, J=8.0 Hz, 1H), 7.24 (d, J=5.2 Hz, 1H), 5.59 (d, J=9.2 Hz, 1H), 4.79-4.75 (m, 1H), 4.71-4.69 (m, 3H), 4.00-3.83 (m, 6H), 3.09-3.05 (m, 1H), 3.94-2.88 (m, 1H), 2.29-2.21 (m, 1H), 2.07-2.04 (m, 1H), 1.75 (s, 9H).

16. Preparation of Crystalline Form A

Compound (R)-1-(tert-butyl)-N-(8-(2-((1-methyl-1H-pyrazol-4-yl)amino)pyrimidin-4-yl)-2,3,4,5-tetrahydro-1H-benzo[c]azepin-5-yl)-1H-1,2,3-triazole-4-carboxamide (1200 g, 2.47 mol) was added to a 20 L reactor at room temperature (25° C.), followed by addition of 24 L of 1,2-dichloroethane at 25° C. To the solution was added oxetan-3-one (534 g, 24.7 mol), NaBH(OAc)₃ (523 g, 2.47 mol), and AcOH (24 mL, 0.17 eq). An additional amount of NaBH(OAc)₃ (1046 g, 4.94 mol) was added in portion to the reactor at room temperature. The mixture was stirred at 25° C. for 16 h. Ice water (12 kg) was added slowly to reactor at room temperature. The organic layer was separated and the aqueous layer was extracted with dichloromethane three time (3×12 L). The combined organic layer was washed with brine (20 L), dried over Na₂SO₄, filtered and concentrated. The crude material was purified by silica gel chromatography (CH₂Cl₂:MeOH=20:1) to afford (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide (compound 27).

The purified compound 27 (950 g) and EtOH (5 L) were vigorously stirred for 4 h and the slurry was filtered and washed with 1 L EtOH. The resulting wet cake was dried under vacuum at 45° C. for ~24 h until reaching a constant weight to afford crystalline Form A (960 g, yield 85.7%, purity 99%).

Example 2

Preparation of Crystalline Form B

About 15 mg of Form A was dissolved in 0.2-1.2 mL dichloromethane (DCM) solvent to obtain a clear solution, and the solution was magnetically stirred (~800 rpm) followed by addition of 0.1 mL anti-solvent toluene per step till the precipitate appeared or the total amount of anti-solvent reached 10.0 mL and then the mixture was stirred at −20° C. for six days. Crystalline form B was analyzed using PXRD, TGA and DSC. The PXRD pattern of crystalline Form B is shown in FIG. 1 and the main peaks are listed in Table 1. A weight loss of 6.6% up to 140° C. was observed on TGA curve as shown in FIG. 2A. DSC profile exhibiting two endotherms at 87.1° C. (peak temp) and 151.0° C. (onset temp) is shown in FIG. 2A, with peak at 87.1° C. being associated with the presence of residual solvent. ¹H NMR showed no DCM or toluene.

TABLE 1

| PXRD peak list for crystalline Form B | | |
|---|---|---|
| 2θ angle | Net Intensity | Relative Intensity |
| 4.10 | 630.76 | 65.58 |
| 6.95 | 961.85 | 100.00 |
| 8.07 | 134.44 | 13.98 |
| 12.12 | 88.58 | 9.21 |
| 13.02 | 55.18 | 5.74 |
| 14.68 | 94.13 | 9.79 |
| 17.56 | 94.11 | 9.78 |
| 18.26 | 158.18 | 16.44 |
| 20.68 | 47.58 | 4.95 |

Variable temperature powder X-ray diffraction (VT-PXRD) of Form B was performed by hearing a sample of Form B to 130° C. under N₂, following by cooling back down to 30° C. FIG. 2B shows an overlay of PXRD patterns for sample at 30° C. with and without N₂, sample at 130° C. as well as sample after cooling down to 30° C. No form conversion was observed after Form B was heated to 130° C. (losing all water at this temperature) under N₂, indicating Form B is a hygroscopic anhydrate.

Example 3

Preparation of Crystalline Form C

Figure 3:
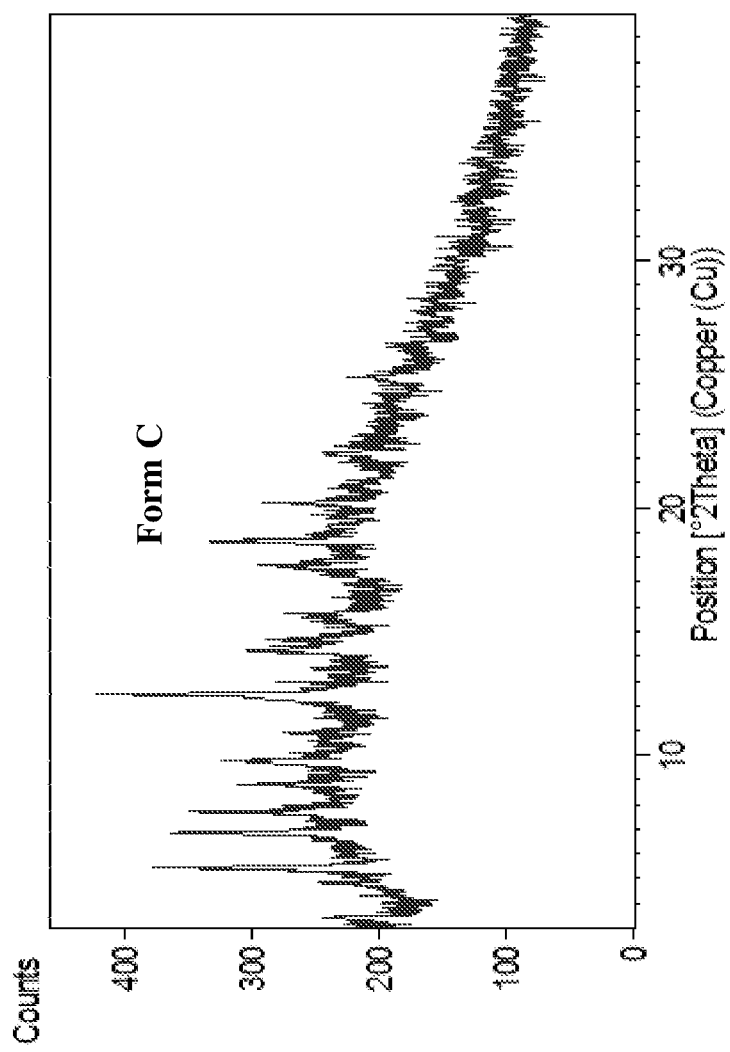
FIG. 3 depicts a powder X-ray diffraction (PXRD) pattern of crystalline Form C of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

About 15 mg of Form A was dissolved in 0.2-1.2 mL dimethylformamide (DMF) solvent to obtain a clear solution, and the solution was magnetically stirred (~800 rpm) followed by addition of 0.1 mL anti-solvent toluene per step till the precipitate appeared or the total amount of anti-solvent reached 10.0 mL and then the mixture was stirred at −20° C. for two days. The PXRD pattern of crystalline Form C is shown in FIG. 3 and the main peaks are listed in Table 2. A weight loss of 5.9% up to 100° C. was observed on TGA curve as shown in FIG. 4A. DSC profile exhibiting an endotherms at 102.5° C. (peak temp) before the sharp melting (153.3° C., onset temp) is shown in FIG. 4A.

TABLE 2

| PXRD peak list for crystalline Form C | | |
|---|---|---|
| 2θ angle | Net Intensity | Relative Intensity |
| 3.37 | 43.97 | 16.25 |
| 5.46 | 195.23 | 72.15 |
| 6.91 | 174.62 | 64.53 |
| 7.69 | 142.38 | 52.62 |
| 8.82 | 114.96 | 42.48 |
| 9.76 | 103.27 | 38.16 |
| 12.45 | 270.61 | 100.00 |
| 14.21 | 100.98 | 37.31 |
| 15.55 | 47.57 | 17.58 |
| 17.61 | 63.58 | 23.49 |
| 18.64 | 128.95 | 47.65 |
| 20.17 | 64.72 | 23.92 |
| 25.27 | 24.31 | 8.98 |

Variable temperature powder X-ray diffraction (VT-PXRD) of Form C was performed. A sample of Form C was dehydrated by purging the sample under N₂ at 30° C. for 20 minutes and then heated to 100° C. under N₂ followed by cooling back down to 30° C. and exposed to air for 20 minutes. FIG. 4B shows an overlay of PXRD patterns for reference sample of Form C, initial sample at 30° C. without N₂, sample purged with N₂ at 30° C., sample heated to 100° C., sample cooled down to 30° C. and sample exposed to air after cooling from 100° C. As shown in FIG. 4B, Form C is converted to Form L after dehydration by purging with N₂ for 20 minutes at 30° C. Form L converts back to Form C after exposure to air for about 2.5 hours and re-absorbs water. This suggests that Form C is a hydrate.

Example 4

Preparation of Crystalline Form D

Figure 5:
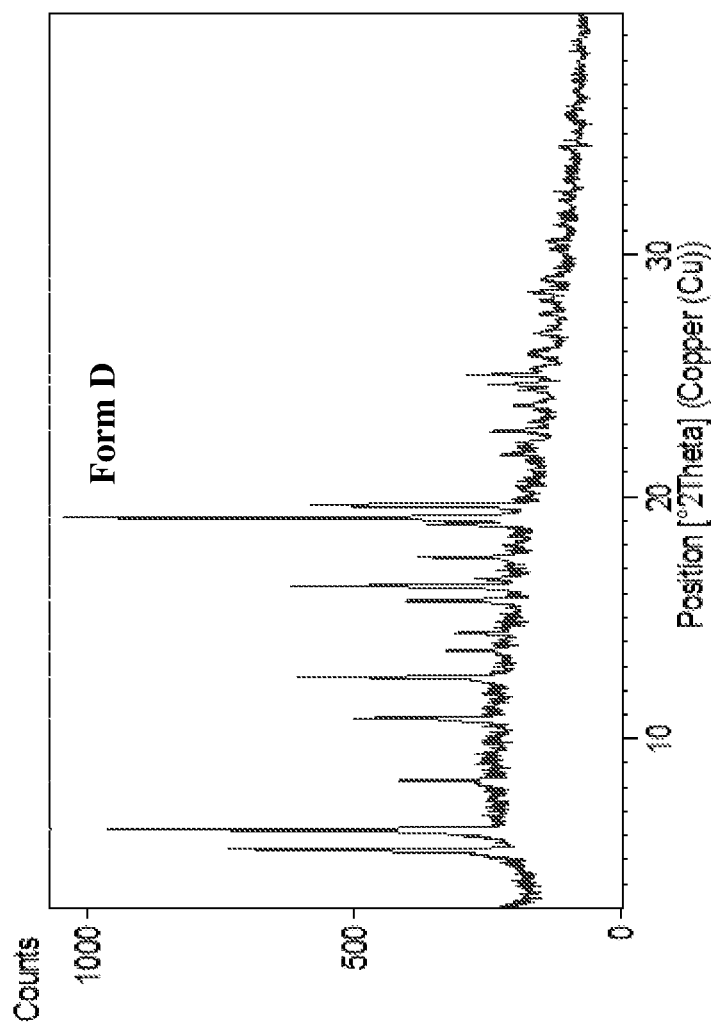
FIG. 5 depicts an powder X-ray diffraction (PXRD) pattern of crystalline Form D of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

About 15 mg of Form A was dissolved in 0.6-4.0 mL of methyl ethyl ketone (MEK) solvent in a ⅗-mL glass vial. The solution was filtered using a PTFE membrane (pore size of 0.45 μm). The resulting visually clear solution was subjected to evaporation at room temperature with vials uncapped. The solids were isolated and analyzed by PXRD (FIG. 5 and Table 3). Form D is postulated to be an acetic acid solvate, based on in ¹H NMR shown in FIG. 7. The DSC analysis shows that Form D has an onset temperature at 153.7° C. and a melting temperature at 173.2° C. (FIG. 6). The TGA analysis of Form D shows a weight loss of 10.1%, indicating that Form D is an acetic acid solvate (FIG. 6).

TABLE 3

PXRD peak list for crystalline Form D

| 2θ angle | Net Intensity | Relative Intensity |
|---|---|---|
| 5.42 | 571.15 | 63.47 |
| 6.26 | 887.80 | 98.65 |
| 8.28 | 245.94 | 27.33 |
| 10.85 | 334.73 | 37.20 |
| 12.54 | 426.30 | 47.37 |
| 13.66 | 156.20 | 17.36 |
| 14.35 | 136.78 | 15.20 |
| 15.70 | 238.40 | 26.49 |
| 16.31 | 461.03 | 51.23 |
| 17.48 | 210.01 | 23.34 |
| 18.85 | 162.61 | 18.07 |
| 19.12 | 899.92 | 100.00 |
| 19.63 | 426.75 | 47.42 |
| 22.72 | 67.33 | 7.48 |
| 23.77 | 51.79 | 5.76 |
| 24.64 | 107.16 | 11.91 |
| 25.02 | 157.45 | 17.50 |
| 25.93 | 39.13 | 4.35 |
| 28.41 | 42.66 | 4.74 |
| 28.99 | 39.13 | 4.35 |
| 30.39 | 16.67 | 1.85 |

Example 5

Preparation of Crystalline Form E

About 15 mg of Form A was suspended in 0.3 mL of acetone/IPAc (1:9) in a 1.5-mL glass vial. The suspension was then heated to 50° C., equilibrated for 30 min and then slowly cooled down to 5° C. at a rate of 0.1° C./min. The obtained solids were kept isothermal at 5° C. after cycled for 3 times.

Alternatively, about 15 mg of Form A was suspended in 0.3 mL of MEK solvent in a 1.5-mL glass vial. After the suspension was stirred magnetically for five days at room temperature, the remaining solids were isolated.

In another experiment, about 15 mg of form A was dissolved in 0.5 mL of CHCl$_3$ solvent, and filtered if needed, to obtain a clear solution in a 3 mL vial. This solution was then placed into a 20 mL vial with 4 mL of n-heptane. The 20 mL vial was sealed with a cap and kept at room temperature allowing sufficient time for anti-solvent vapor to interact with the solution to precipitate out Form E.

In another experiment, about 15 mg of Form A and 2 mg of ionic liquid [bmim]PF$_6$ or [emim]SbF$_6$ were weighted in a 5-mL vial and solids were dissolved in 0.6-4.0 mL MeOAc or THF. The vial was sealed using parafilm with several small holes for slow evaporation to yield Form E.

Figure 8:
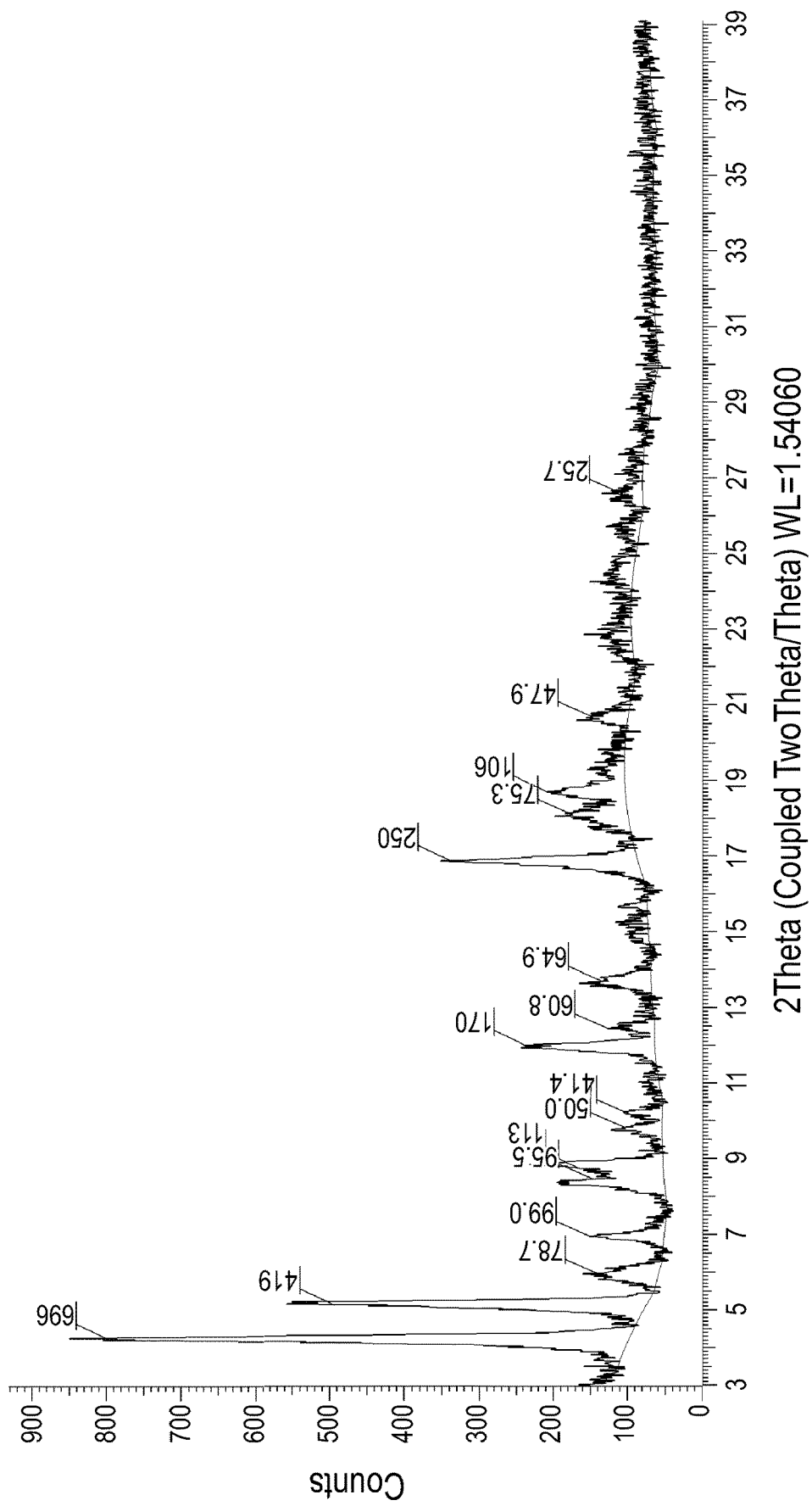
FIG. 8 depicts a powder X-ray diffraction (PXRD) pattern of crystalline Form E of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The PXRD pattern of crystalline Form E is shown in FIG. 8 and the main peaks are listed in Table 4. The DSC analysis shows that Form E has an onset temperature at 161.5° C. and a melting temperature at 167.8° C. (FIG. 9). The TGA analysis of Form E shows 1.6% weight loss, indicating that Form E is anhydrous (FIG. 9).

TABLE 4

PXRD peak list for crystalline Form E

| 2θ angle | Net Intensity | Relative Intensity |
|---|---|---|
| 4.20 | 696.30 | 1.00 |
| 5.13 | 418.91 | 0.60 |
| 5.93 | 78.72 | 0.11 |
| 6.95 | 99.02 | 0.14 |
| 8.45 | 95.54 | 0.14 |
| 8.74 | 112.66 | 0.16 |
| 9.82 | 49.98 | 0.07 |
| 10.16 | 41.42 | 0.06 |
| 11.96 | 170.10 | 0.24 |
| 12.43 | 60.75 | 0.09 |
| 13.68 | 64.94 | 0.09 |
| 16.85 | 250.43 | 0.36 |
| 18.10 | 75.34 | 0.11 |
| 18.71 | 106.12 | 0.15 |
| 20.67 | 47.95 | 0.07 |
| 26.56 | 25.71 | 0.04 |

Example 6

Preparation of Crystalline Form F

About 15 mg of Form A was suspended in 0.3 mL of MIBK in a 1.5 mL glass vial. The suspension was then heated to 50° C., equilibrated for 30 min and then slowly cooled down to 5° C. at a rate of 0.1° C./min. The obtained solids were kept isothermal at 5° C. after cycled for 3 times.

Alternatively, about 15 mg of Form A was suspended in 0.3 mL of MIBK in a 1.5 mL glass vial. After the suspension was stirred magnetically for five days at room temperature, the remaining solids were isolated.

In another experiment, about 15 mg of Form A was suspended in 0.6-1.4 mL of methanol in a 1.5 mL vial and then filtered to a new 3 mL vial containing about 2 mg of polymer mixture A (a mixture of polyvinyl pyrrolidone (PVP), polyvinyl alcohol (PVA), polyvinylchloride (PVC), polyvinyl acetate (PVAC), hypromellose (HPMC), methyl cellulose (MC) with mass ratio of 1:1:1:1:1:1). The solution was stirred magnetically (1000 rpm) at room temperature for about three days to obtain form F.

Figure 10:
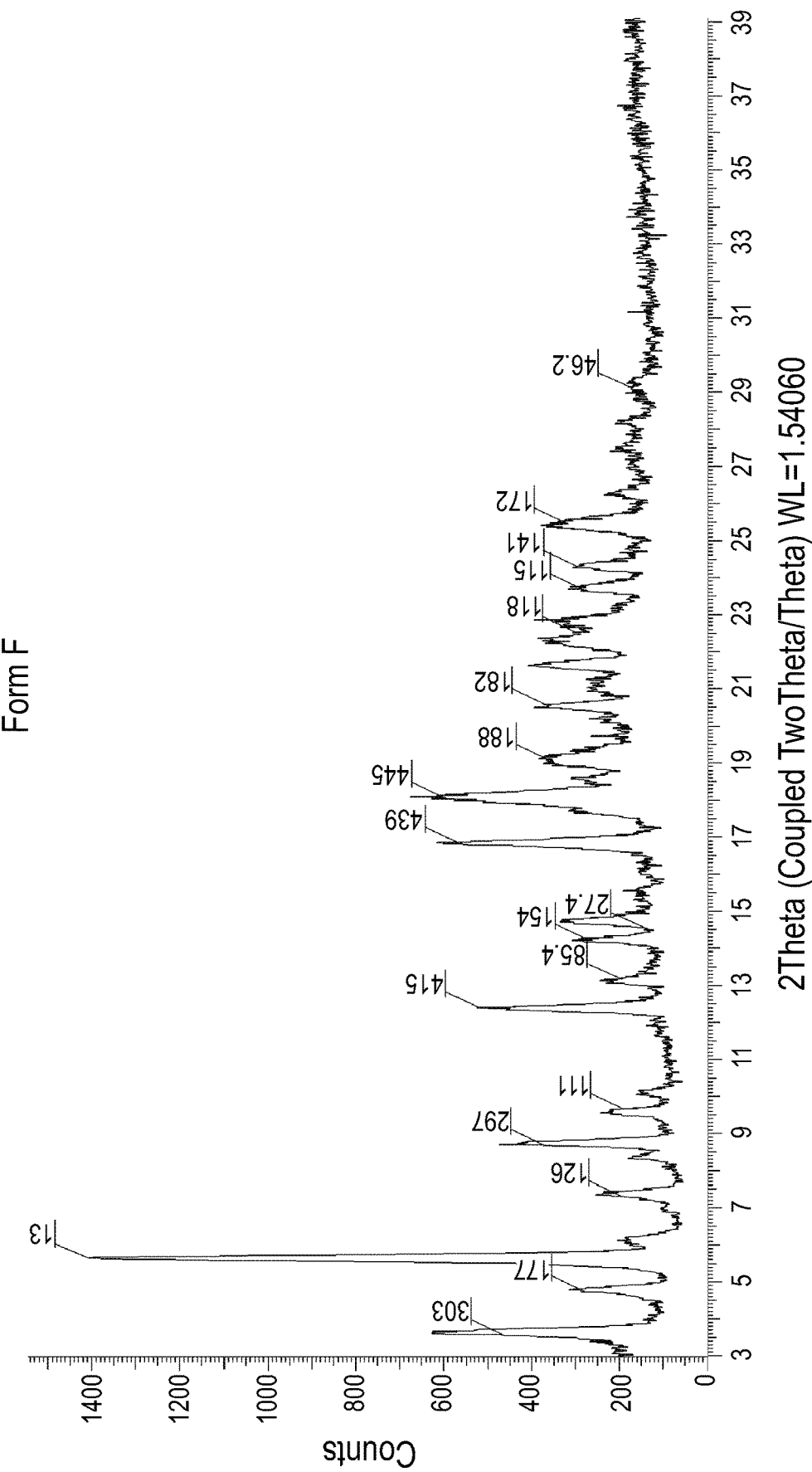
FIG. 10 depicts a powder X-ray diffraction (PXRD) pattern of crystalline Form F of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The PXRD pattern of crystalline Form F is shown in FIG. 10 and the main peaks are listed in Table 5. The DSC analysis shows that Form F has an onset temperature at 169.4° C. and a melting temperature at 174.7° C. (FIG. 11). The TGA analysis of Form F shows 1.9% weight loss, indicating that Form F is anhydrous (FIG. 11).

TABLE 5

PXRD peak list for crystalline Form F

| 2θ angle | Net Intensity | Relative Intensity |
|---|---|---|
| 3.56 | 302.69 | 0.23 |
| 4.74 | 176.79 | 0.13 |
| 5.65 | 1317.97 | 1.00 |
| 7.31 | 126.45 | 0.10 |
| 8.68 | 297.14 | 0.23 |
| 9.66 | 111.24 | 0.08 |
| 12.40 | 415.05 | 0.31 |
| 13.21 | 85.40 | 0.06 |
| 14.22 | 154.48 | 0.12 |
| 14.55 | 27.43 | 0.02 |
| 16.83 | 438.71 | 0.33 |
| 18.05 | 445.21 | 0.34 |
| 19.07 | 188.23 | 0.14 |
| 20.57 | 182.35 | 0.14 |
| 22.51 | 117.82 | 0.09 |
| 23.67 | 115.20 | 0.09 |

TABLE 5-continued

PXRD peak list for crystalline Form F

| 2θ angle | Net Intensity | Relative Intensity |
| --- | --- | --- |
| 24.31 | 140.57 | 0.11 |
| 25.46 | 171.53 | 0.13 |
| 29.13 | 46.16 | 0.04 |

Example 7

Preparation of Crystalline Form H

About 15 mg of Form A was suspended in 0.3 mL of 2-methyl tetrahydrofuran (2-MeTHF) in a 1.5 mL glass vial. The suspension was then heated to 50° C., equilibrated for 30 min and then slowly cooled down to 5° C. at a rate of 0.1° C./min. The obtained solids were kept isothermal at 5° C. after cycled for 3 times.

Figure 12:
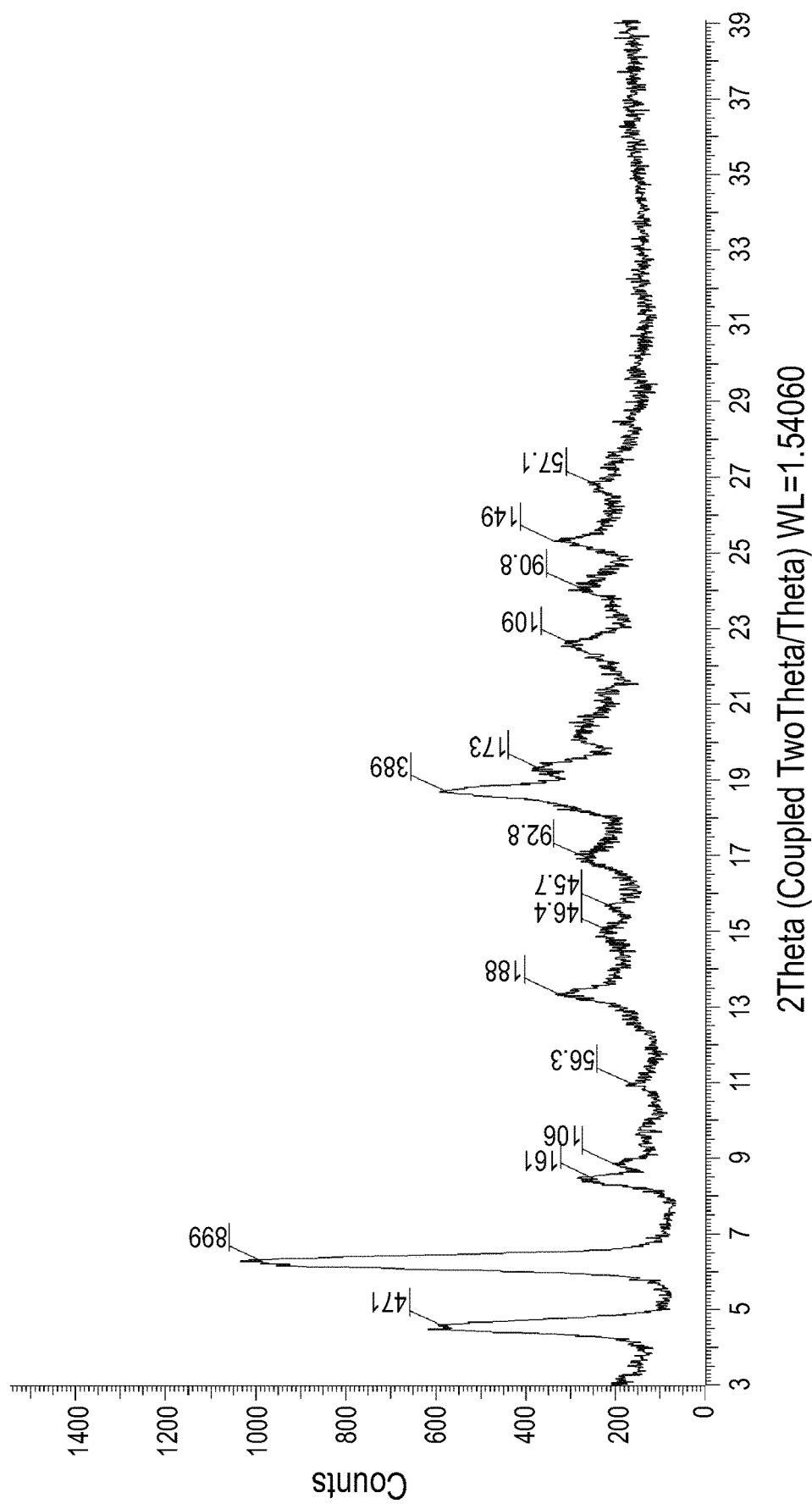
FIG. 12 depicts a powder X-ray diffraction (PXRD) pattern of crystalline Form H of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The PXRD pattern of crystalline Form H is shown in FIG. 12 and the main peaks are listed in Table 6. The DSC analysis for crystalline Form H shows that Form H has an onset temperature at 153.1° C. and a melting temperature at 161.1° C. (FIG. 13A). The TGA analysis of Form H shows 8.9% weight loss, indicating that Form H is anhydrous (FIG. 13A).

TABLE 6

PXRD peak list for crystalline Form H

| 2θ angle | Net Intensity | Relative Intensity |
| --- | --- | --- |
| 4.55 | 470.97 | 0.52 |
| 6.26 | 898.72 | 1.00 |
| 8.44 | 160.77 | 0.18 |
| 8.82 | 106.33 | 0.12 |
| 10.97 | 56.27 | 0.06 |
| 13.35 | 187.67 | 0.21 |
| 14.94 | 46.41 | 0.05 |
| 15.60 | 45.73 | 0.05 |
| 16.94 | 92.84 | 0.10 |
| 18.71 | 389.33 | 0.43 |
| 19.27 | 172.74 | 0.19 |
| 22.55 | 108.65 | 0.12 |
| 24.08 | 90.78 | 0.10 |
| 25.31 | 148.63 | 0.17 |
| 26.76 | 57.07 | 0.06 |

A sample of Form H was heated to 125° C. and PXRD pattern was compared with PXRD pattern for the sample before heating. FIG. 13B shows that no form conversion was observed when the sample of Form H was heated to 125° C., suggesting that Form H is an anhydrate.

Example 8

Preparation of Crystalline Form J

About 15 mg of Form A was dissolved in 0.6-4.0 mL of anisole in a 3/5 mL glass vial, and filtered using a PTFE membrane (pore size of 0.45 μm) if needed, to obtain a clear solution. The resulting solution was subjected to evaporation at room temperature with vials uncapped to yield Form J.

Figure 14:
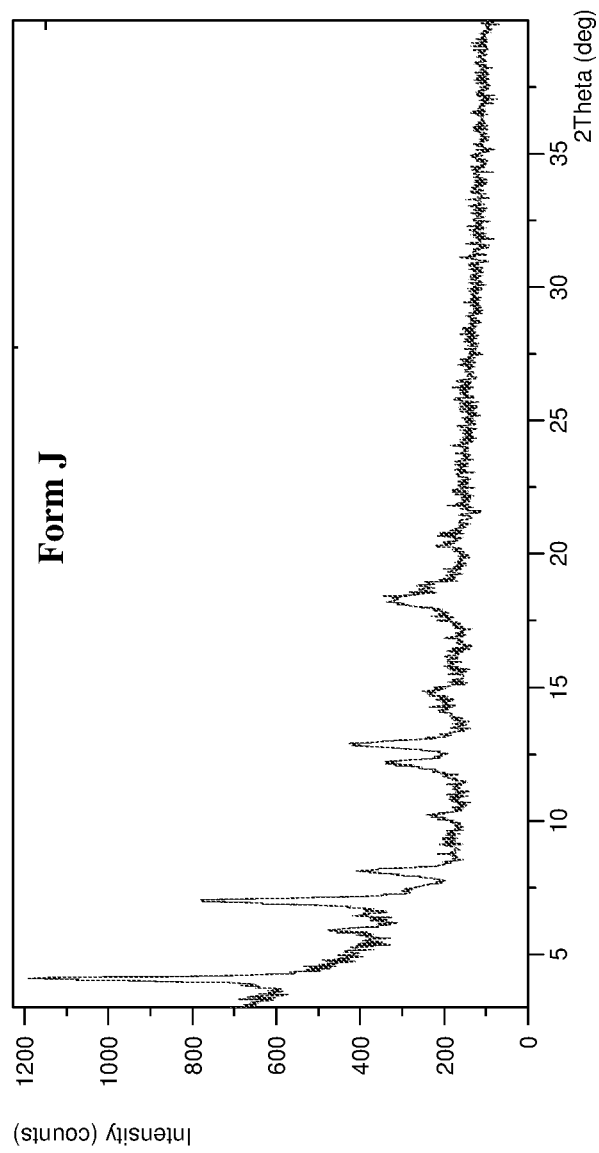
FIG. 14 depicts a powder X-ray diffraction (PXRD) pattern of crystalline Form J of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Form J is postulated to be a hydrate or hygroscopic anhydrate based on $^1$H NMR, DSC, TGA and PXRD. The PXRD pattern of crystalline Form J is shown in FIG. 14 and the main peaks are listed in Table 7.

TABLE 7

PXRD peak list for crystalline Form J

| Angle | Net Intensity | Relative Intensity |
| --- | --- | --- |
| 4.02 | 1100 | 1.00 |
| 5.98 | 380 | 0.35 |
| 7.10 | 670 | 0.61 |
| 7.30 | 300 | 0.27 |
| 10.50 | 140 | 0.13 |
| 12.01 | 220 | 0.20 |
| 12.50 | 320 | 0.29 |
| 15.05 | 130 | 0.12 |
| 18.10 | 230 | 0.21 |

The DSC analysis for crystalline Form J shows that Form J has an onset temperature at 145.2° C. and a melting temperature at 150.2° C. (FIG. 15). The TGA analysis of Form J shows 4.6% weight loss, indicating that Form J is hydrate or hygroscopic anhydrate (FIG. 15).

Example 9

Preparation of Crystalline Form K

Figure 16:
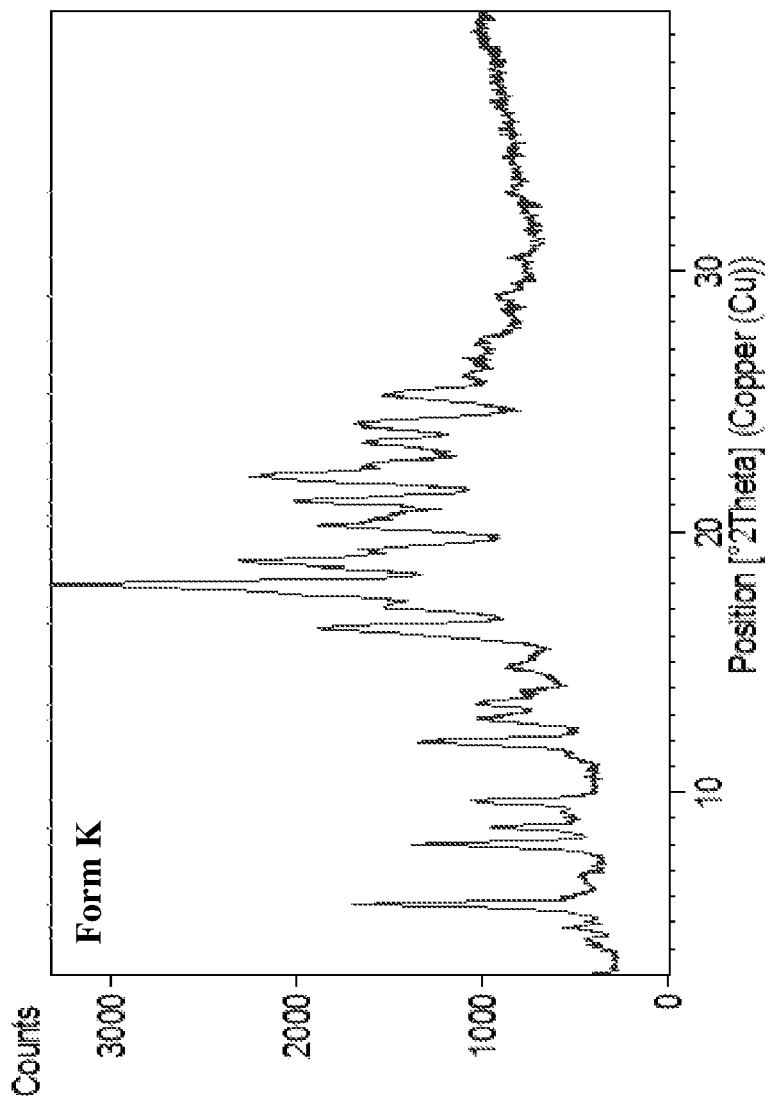
FIG. 16 depicts a powder X-ray diffraction (PXRD) pattern of crystalline Form K of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Crystalline Form K was produced by heating Form A to 130° C. under $N_2$ protection. The PXRD pattern of crystalline Form K is shown in FIG. 16 and the main peaks are listed in Table 8.

TABLE 8

PXRD peak list for crystalline Form K

| 2θ angle | Net Intensity | Relative Intensity |
| --- | --- | --- |
| 5.73 | 1371.48 | 49.25 |
| 8.00 | 1024.52 | 36.79 |
| 8.66 | 582.82 | 20.93 |
| 9.70 | 682.12 | 24.50 |
| 11.98 | 831.92 | 29.88 |
| 12.79 | 554.51 | 19.91 |
| 13.38 | 587.82 | 21.11 |
| 14.80 | 403.62 | 14.50 |
| 16.45 | 980.12 | 35.20 |
| 17.07 | 1017.38 | 36.54 |
| 17.95 | 2784.55 | 100.00 |
| 18.86 | 1774.94 | 63.74 |
| 19.30 | 1138.39 | 40.88 |
| 20.22 | 1283.79 | 46.10 |
| 20.66 | 851.21 | 30.57 |
| 21.13 | 1415.33 | 50.83 |
| 21.98 | 1520.73 | 54.61 |
| 22.66 | 958.20 | 34.41 |
| 23.36 | 1018.23 | 36.57 |

Example 10

Preparation of Crystalline Form L

Figure 17:
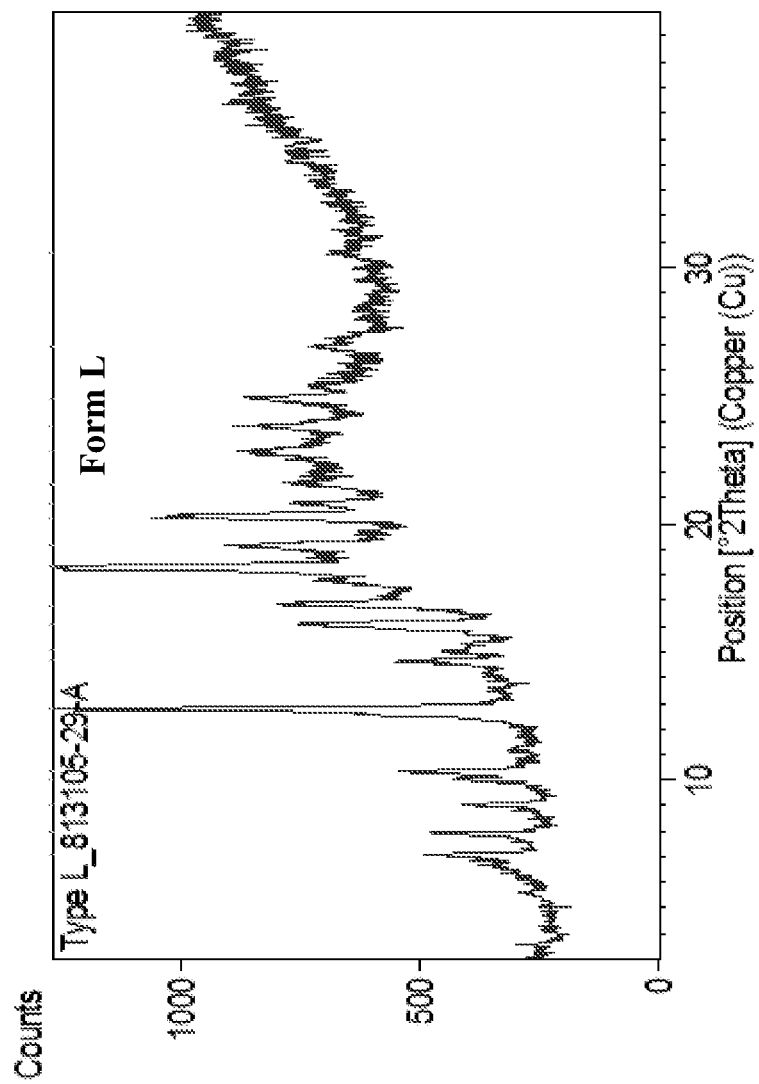
FIG. 17 depicts a powder X-ray diffraction (PXRD) pattern of crystalline Form L of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Crystalline Form L was produced by heating Form C to 130° C. under $N_2$ protection. The PXRD pattern of crystalline Form L is shown in FIG. 17 and the main peaks are listed in Table 9.

TABLE 9

PXRD peak list for crystalline Form L

| 2θ angle | Net Intensity | Relative Intensity |
| --- | --- | --- |
| 7.09 | 243.30 | 25.03 |
| 7.94 | 226.75 | 23.33 |

TABLE 9-continued

PXRD peak list for crystalline Form L

| 2θ angle | Net Intensity | Relative Intensity |
|---|---|---|
| 9.05 | 160.70 | 16.53 |
| 10.01 | 161.40 | 16.60 |
| 10.36 | 262.84 | 27.04 |
| 12.80 | 972.00 | 100.00 |
| 14.64 | 188.55 | 19.40 |
| 15.05 | 97.59 | 10.04 |
| 16.09 | 398.41 | 40.99 |
| 16.80 | 394.77 | 40.61 |
| 18.36 | 794.69 | 81.76 |
| 19.13 | 483.17 | 49.71 |
| 20.22 | 574.93 | 59.15 |
| 20.80 | 303.30 | 31.20 |
| 21.52 | 287.19 | 29.55 |
| 22.80 | 372.96 | 38.37 |
| 23.81 | 350.18 | 36.03 |
| 24.88 | 335.22 | 34.49 |
| 26.91 | 158.92 | 16.35 |

Example 11

Preparation of Crystalline Form M

Figure 18:
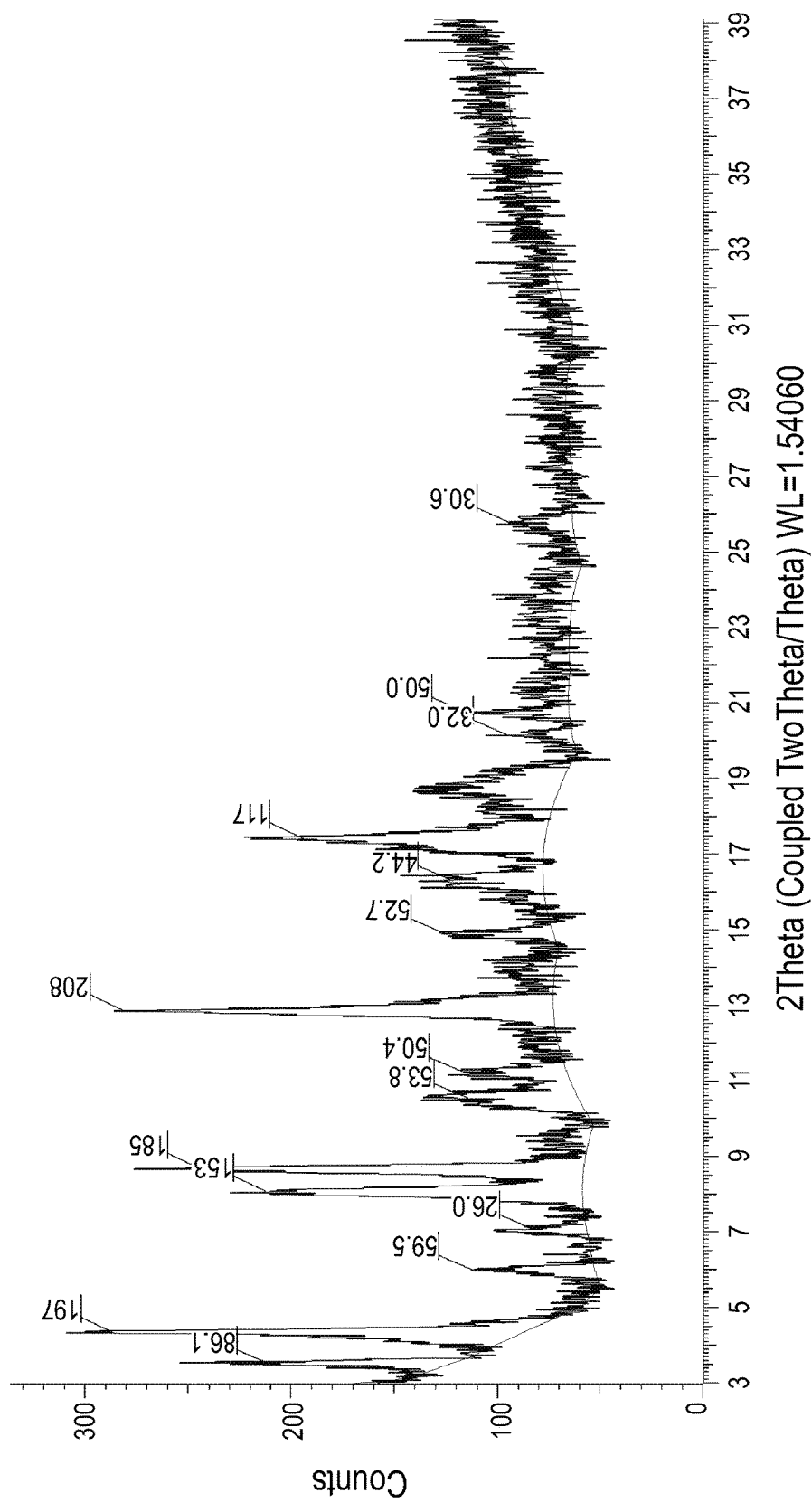
FIG. 18 depicts a powder X-ray diffraction (PXRD) pattern of crystalline Form M of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Crystalline Form M was produced by slurring Form F or Form H in toluene at room temperature for 2 weeks. The PXRD pattern of crystalline Form M is shown in FIG. 18 and the main peaks are listed in Table 10.

TABLE 10

PXRD peak list for crystalline Form M

| 2θ angle | Net Intensity | Relative Intensity |
|---|---|---|
| 3.49 | 86.10 | 0.41 |
| 4.32 | 196.79 | 0.95 |
| 5.98 | 59.52 | 0.29 |
| 7.06 | 26.01 | 0.13 |
| 8.04 | 153.43 | 0.74 |
| 8.65 | 185.45 | 0.89 |
| 10.54 | 53.84 | 0.26 |
| 11.23 | 50.37 | 0.24 |
| 12.85 | 208.03 | 1.00 |
| 14.89 | 52.67 | 0.25 |
| 16.31 | 44.17 | 0.21 |
| 17.40 | 117.05 | 0.56 |
| 20.14 | 31.96 | 0.15 |
| 20.74 | 50.00 | 0.24 |
| 25.76 | 30.61 | 0.15 |

Example 12

Preparation of Crystalline Form N 2.0 g of Form A was stirred in 20 volumes of THF at 45° C. using a 50 mL EasyMAx reactor with overhead and a Dean-Stark distillation trap. The solution was concentrated with Tr–Tj set to −20° C. and $T_{jmax}$ of 110° C. ($T_r$ is reaction temperature and $T_j$ is jacket temperature). After 5 V of distillate was removed, reactor was charged back with 5 V of isopropyl acetate, and a precipitate started forming. Continued distilling with Tr–Tj=−20° C. removed another 10 V of distillate and 10 V of isopropyl acetate was added back. The reactor contents were cooled to 20° C. as quickly as possible. Solids were isolated in Buchner funnel and blown down for 3 h.

Alternatively, a slurry of Form A in 1.0 mL of THF was stirred overnight using a microstir bar at 500 rpm. The slurry was then transferred to a microcentrifuge Eppendorf tube and spun down at 5000 rpm for 1 min. The supernatant was decanted and the wetcake analyzed by PXRD and determined to be Form N.

Figure 19:
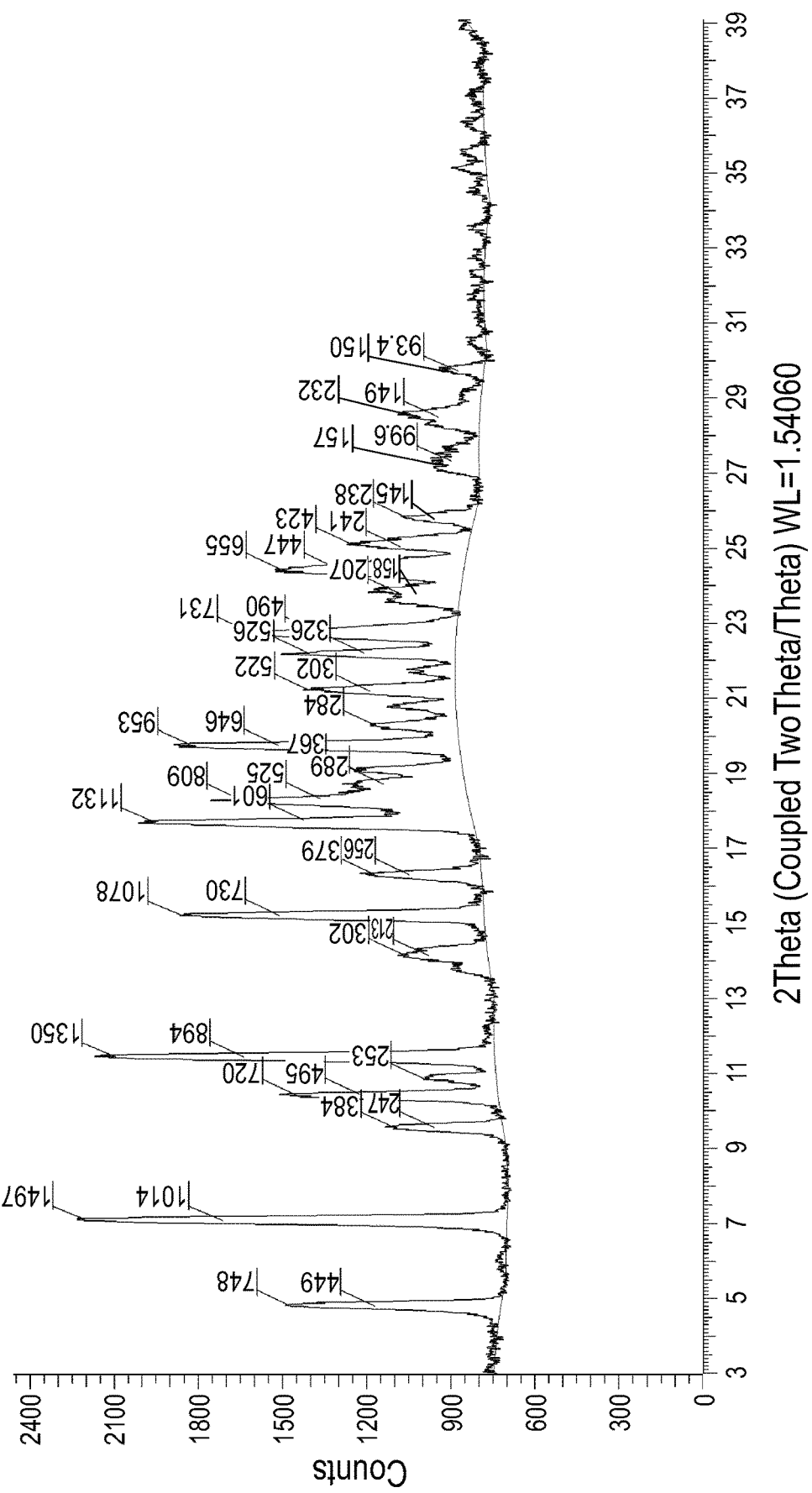
FIG. 19 depicts a powder X-ray diffraction (PXRD) pattern of crystalline Form N of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The PXRD pattern of crystalline Form N is shown in FIG. 19 and the main peaks are listed in Table 11. The DSC analysis for crystalline Form N shows that Form N has an onset temperature at 132.3° C. and a melting temperature at 146.3° C. (FIG. 20).

TABLE 11

PXRD peak list for crystalline Form N

| 2θ angle | Net Intensity | Relative Intensity |
|---|---|---|
| 4.81 | 748.20 | 0.50 |
| 7.09 | 1497.23 | 1.00 |
| 9.54 | 383.64 | 0.26 |
| 10.42 | 720.48 | 0.48 |
| 10.85 | 252.51 | 0.17 |
| 11.45 | 1349.69 | 0.90 |
| 14.18 | 302.43 | 0.20 |
| 15.21 | 1077.82 | 0.72 |
| 16.29 | 378.75 | 0.25 |
| 17.70 | 1132.49 | 0.76 |
| 18.30 | 808.81 | 0.54 |
| 19.04 | 366.83 | 0.25 |
| 19.75 | 952.64 | 0.64 |
| 20.25 | 283.64 | 0.19 |
| 21.23 | 521.76 | 0.35 |
| 22.21 | 525.63 | 0.35 |
| 22.75 | 731.12 | 0.49 |
| 23.78 | 207.00 | 0.14 |
| 24.45 | 654.89 | 0.44 |
| 25.13 | 422.82 | 0.28 |
| 25.82 | 238.43 | 0.16 |
| 27.27 | 157.33 | 0.11 |
| 28.52 | 231.61 | 0.15 |
| 29.75 | 149.78 | 0.10 |

Example 13

Preparation of Crystalline Form P

Method A:

Approximately 2 g of Form A in a flask was added 30 mL of DCM. The resulting mixture was stirred to become solution and filtered. The flask was rinsed with 10 mL of DCM. Upon filtering, the solution became gel in the receiving flask and some clogging with the funnel was observed. To the gel was added 40 mL of propyl acetate and mixed with the help of a spatula to form a gel suspension in propyl acetate. The mixture was put on rotavap (no vacuum) at 1 atmosphere pressure with the heating bath temperature increased from 25 to 90° C. over 30 min with 200 rpm rotating. After 1 h, the gel mixture was stirred with 280 rpm by adding a stirring bar to improve mixing. After 5 h, the whole slurry was transferred into 100 ml bottle and stirred at 90° C. overnight with 250 rpm (minimum $N_2$ flow) for overnight to yield Form P.

Figure 21:
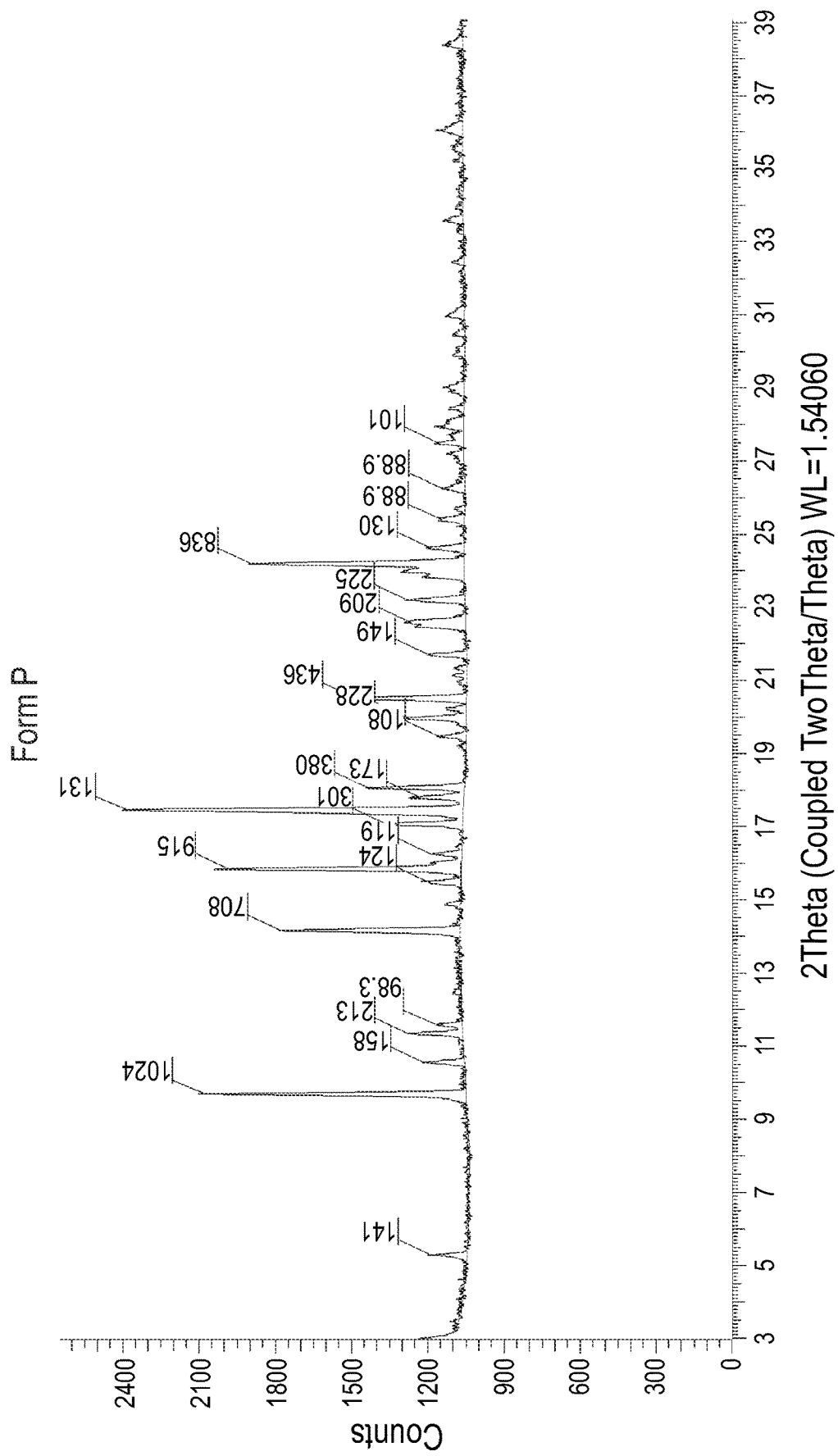
FIG. 21 depicts a powder X-ray diffraction (PXRD) pattern of crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

The PXRD pattern of crystalline Form P is shown in FIG. 21 and the main peaks are listed in Table 12. The DSC analysis for crystalline Form P shows that Form P has an onset temperature at 196.9° C. and a melting temperature at 201.3° C. (FIG. 22). The TGA analysis of Form P indicates that Form P is a hydrate (FIG. 22) having 2.2-2.6 wt % of water.

TABLE 12

PXRD peak list for crystalline Form P

| 2θ angle | Net Intensity | Relative Intensity |
|---|---|---|
| 5.29 | 141.00 | 0.11 |
| 9.69 | 1023.93 | 0.78 |
| 10.56 | 157.60 | 0.12 |
| 11.35 | 213.10 | 0.16 |
| 11.58 | 98.34 | 0.07 |
| 14.16 | 707.86 | 0.54 |
| 15.48 | 123.66 | 0.09 |
| 15.84 | 915.02 | 0.70 |
| 16.25 | 119.32 | 0.09 |
| 17.08 | 300.65 | 0.23 |
| 17.45 | 1315.43 | 1.00 |
| 17.81 | 172.90 | 0.13 |
| 18.07 | 379.76 | 0.29 |
| 19.48 | 107.72 | 0.08 |
| 19.97 | 227.71 | 0.17 |
| 20.50 | 435.72 | 0.33 |
| 21.71 | 149.38 | 0.11 |
| 22.56 | 209.40 | 0.16 |
| 23.20 | 225.25 | 0.17 |
| 24.19 | 835.94 | 0.64 |
| 24.64 | 130.24 | 0.10 |
| 25.42 | 88.90 | 0.07 |
| 26.27 | 88.86 | 0.07 |
| 27.50 | 100.72 | 0.08 |

Figure 26:
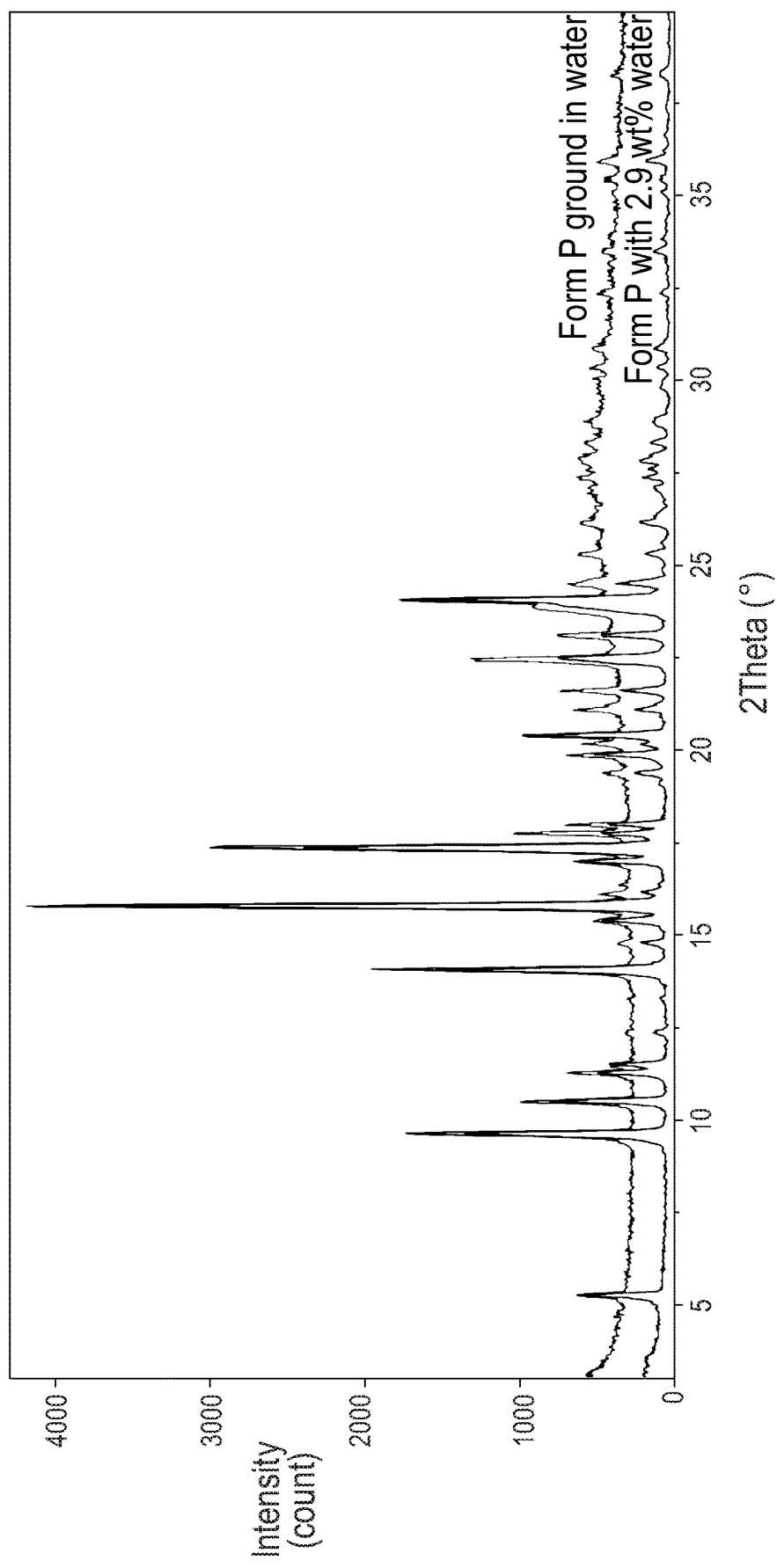
FIG. 26 depicts an overlay of PXRD patterns of crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide with 2.9 wt % water and Form P ground in water.
Figure 27:
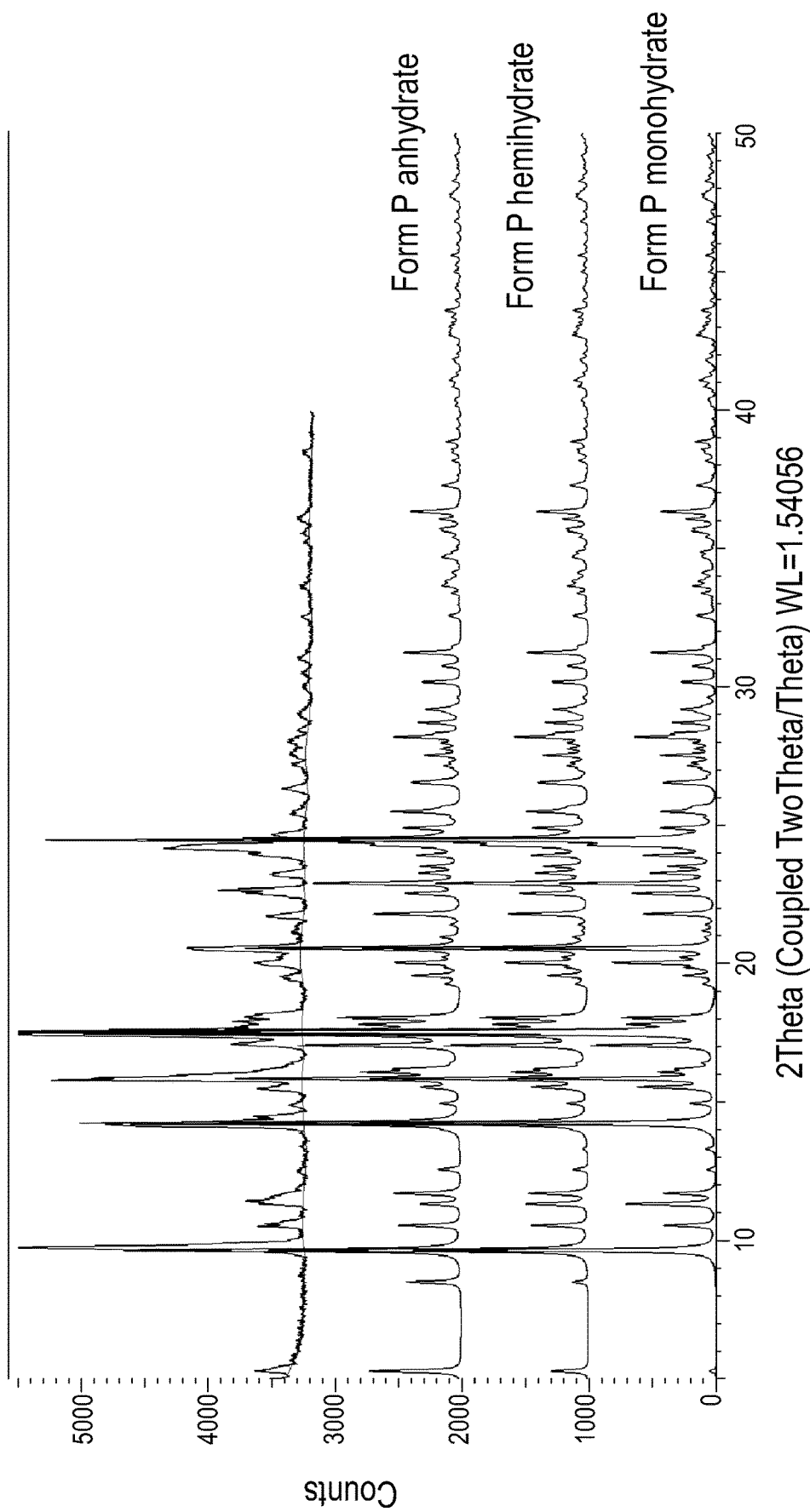
FIG. 27 depicts an overlay of PXRD patterns of crystalline Form P anhydrate, crystalline Form P hemihydrate and crystalline Form P monohydrate of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Crystalline Form P with 2.9 wt % of water were prepared using similar procedures as described in Method A. Dichloromethane (15V) and n-propyl acetate (35 V) were used as solvents and the DSC/TGA graph is shown in FIG. 25. Crystalline Form P with 2.9 wt % of water was ground in water using a mortar and pestle to produce a viscous slurry. The sample was rapidly prepared, covered with Kapton film and analyzed by PXRD. No peak shifts were observed in the PXRD pattern after Form P was ground in water. An overlay of PXRD pattern for Form P and Form P ground in water is shown in FIG. 26.

Figure 23:
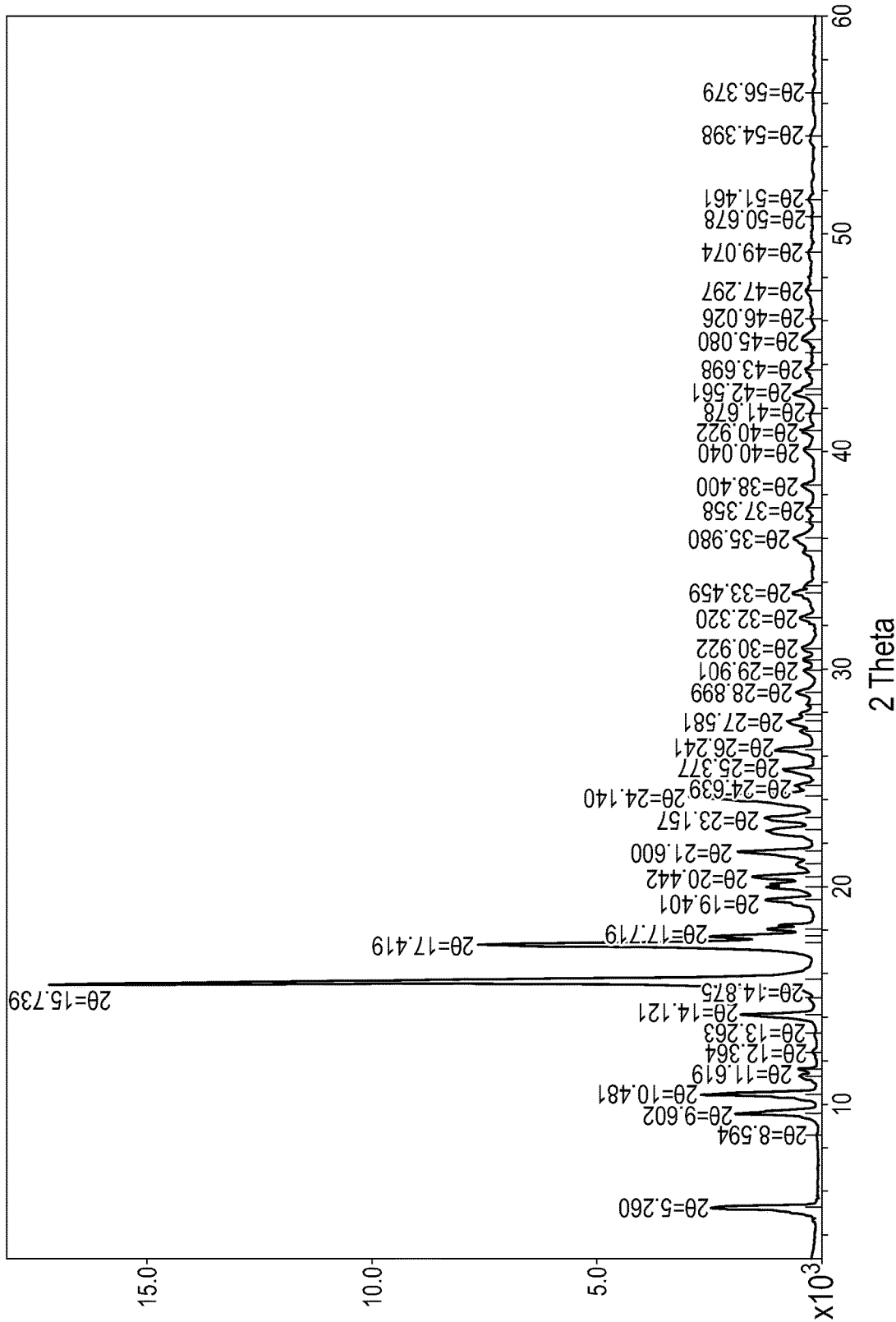
FIG. 23 depicts a powder X-ray diffraction (PXRD) pattern of crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide with 0.4 wt % water.

Method B:

To a clean 500 L glass-lined reactor was added 217 kg dichloromethane and 22.0 kg of Form A of the compound at 25-30° C. Heat the mixture to 30-35° C. until the compound was completely dissolved. Charge 191 kg of isopropyl acetate into the reactor at 45-50° C. Peristaltic pump was used to control the flow rate of 2 L/minute. Distill the mixture at 45-50° C. by atmosphere distillation to about 15.0 V (volume). Charge 191 kg of isopropyl acetate into the reactor at 60-82° C. Peristaltic pump was used to control the flow rate of 2 L/minute. Distill the mixture at 60-82° C. by atmospheric distillation to about 15 V. Charge 191 kg of isopropyl acetate into the reactor at 82-89° C. Peristaltic pump was used to control the flow rate of 2 L/minute. Distill the mixture at 82-89° C. by atmospheric distillation to about 15 V. Charge 191 kg of isopropyl acetate into the reactor at 85-89° C. Peristaltic pump was used to control the flow rate of 2 L/minute. Distill the mixture at 85-89° C. by atmospheric distillation to about 15 V. Charge 150 kg H$_2$O into the reactor at 85-88° C. Peristaltic pump was used to control the flow rate of 0.5 L/minute. Stir the mixture at 85-88° C. for 1 hour. Cool the mixture to 65-70° C. and stir the mixture at 65-70° C. for 8 hours. Then cool the mixture to 15-20° C. for 3.0 hr at a rate of 15° C./hour. Separate the product through centrifuge and dry the solid in the vacuum drying oven at 65° C. for 24 hours to form light yellow solid (21.0 kg). Water content (0.40 wt %) was determined by Karl Fisher (KF) analysis. The PXRD pattern of crystalline Form P is shown in FIG. 23.

Method C

1) To a clean 100 L jacketed reactor was charged 5.30 kg of dichloromethane under inert condition (nitrogen), followed by 2.623 kg of Form A. An additional 42.0 kg of dichloromethane was added to the reactor and the resulting slurry was heated to approximately 30-35° C. and stirred until complete dissolution of the compound. The solution was filtered through a 5 inch Teflon membrane capsule filter (0.22 micron) into a pre-cleaned drum container under an inert atmosphere. The reactor was rinsed with dichloromethane and the rinse solution was transferred to the drum through the Teflon filter. The combined dichloromethane solution from the drum was charged back to the jacketed reactor and heat the solution to 30-35° C.

2) As the solution in the jacketed reactor was opaque, purified water (26 kg) was added to the reactor while maintaining the temperature of 30-35° C. The resulting biphasic mixture was stirred for a minimum of 5 minutes and then the layers was allowed to settle. The bottom product-containing organic layer was drained to a container and the top aqueous layer to a separate container. The jacketed reactor was rinsed with purified water and drained in the container with the aqueous layer. Charge the organic layer back to the jacketed reactor and repeating the steps described in 2).

3) The organic solution in the jacketed reactor was transferred into a pre-cleaned drum container through a 5 inch Teflon membrane capsule filter (0.22 micron) under inert atmosphere. The jacketed was rinsed with 0.2 μm filtered dichloromethane (4.2 kg) and the rinse solution was transferred to the drum through the Teflon filter. The solution in the drum containedr was charged to the jacketed reactor and the drum container was rinsed with 0.2 μm filtered dichloromethane (4.7 kg). The solution in the jacketed reactor was concentrated by distillation while maintaining a ΔT ($T_{jacket}-T_{batch}$) of approximately 20-30° C. until the final volume was approximately 26 L. 17.1 kg of 0.2 μm filtered dichloromethane was added to the reactor and the solution was cooled to approximately 30-35° C. The water content of the solution was determined to be ≤300 pm.

4) 68 kg of 0.2 μm filtered isopropyl acetate was added to a separate container under an inert atmosphere. The solution in the reactor was concentrated by atmospheric distillation while isopropyl acetate was simultaneously charged to the reactor using a Piston Pump. During concentration, a ΔT ($T_{jacket}-T_{batch}$) of approximately 20-40° C. was maintained until the final volume reach about 26 L.

5) 33 kg of 0.2 μm filtered isopropyl acetate was added to the reactor under an inert atmosphere. The resulting solution was concentrated by atmospheric distillation while maintaining a ΔT ($T_{jacket}-T_{batch}$) of approximately 20-30° C. until the final volume reached 40 L.

6) Cool the solution to 65-90° C. and the solution was stirred under an inert atmosphere for a minimum of 12 hours.

Figure 24:
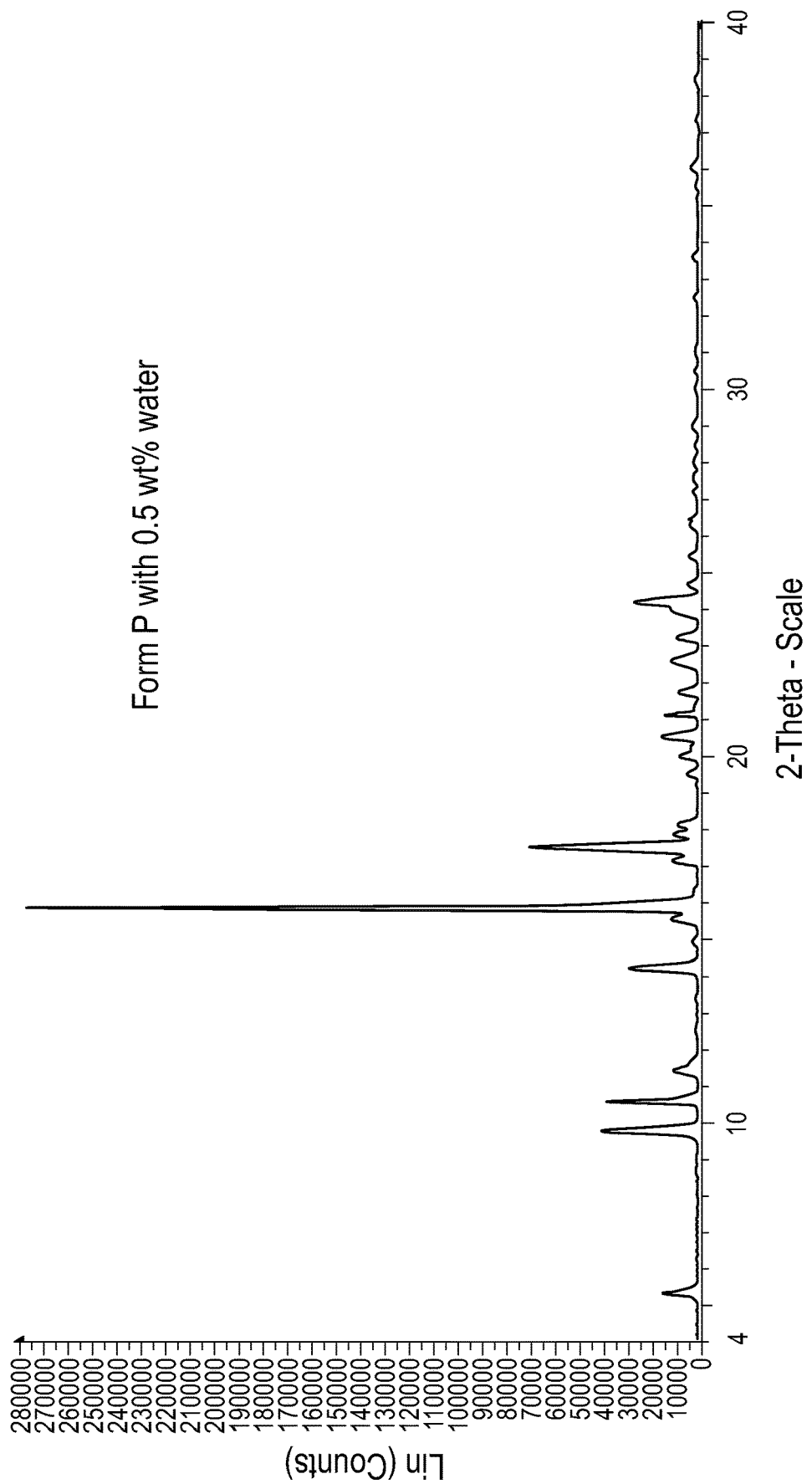
FIG. 24 depicts a powder X-ray diffraction (PXRD) pattern of crystalline Form P of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide with 0.5 wt % water.

7) Cool the solution to approximately 20-25° C. and filter the contents of the reactor onto a filter funnel, pre-cleaned with 0.2 μm filtered isopropyl acetate. The solids on the filter funnel was dried under nitrogen and/or vacuum for a minimum of 6 hours to yield 1960.9 g of crystalline Form P with 0.5 wt % water. The PXRD pattern is shown in FIG. 24.

Example 14

Preparation of Crystalline Form Q

Figure 28:
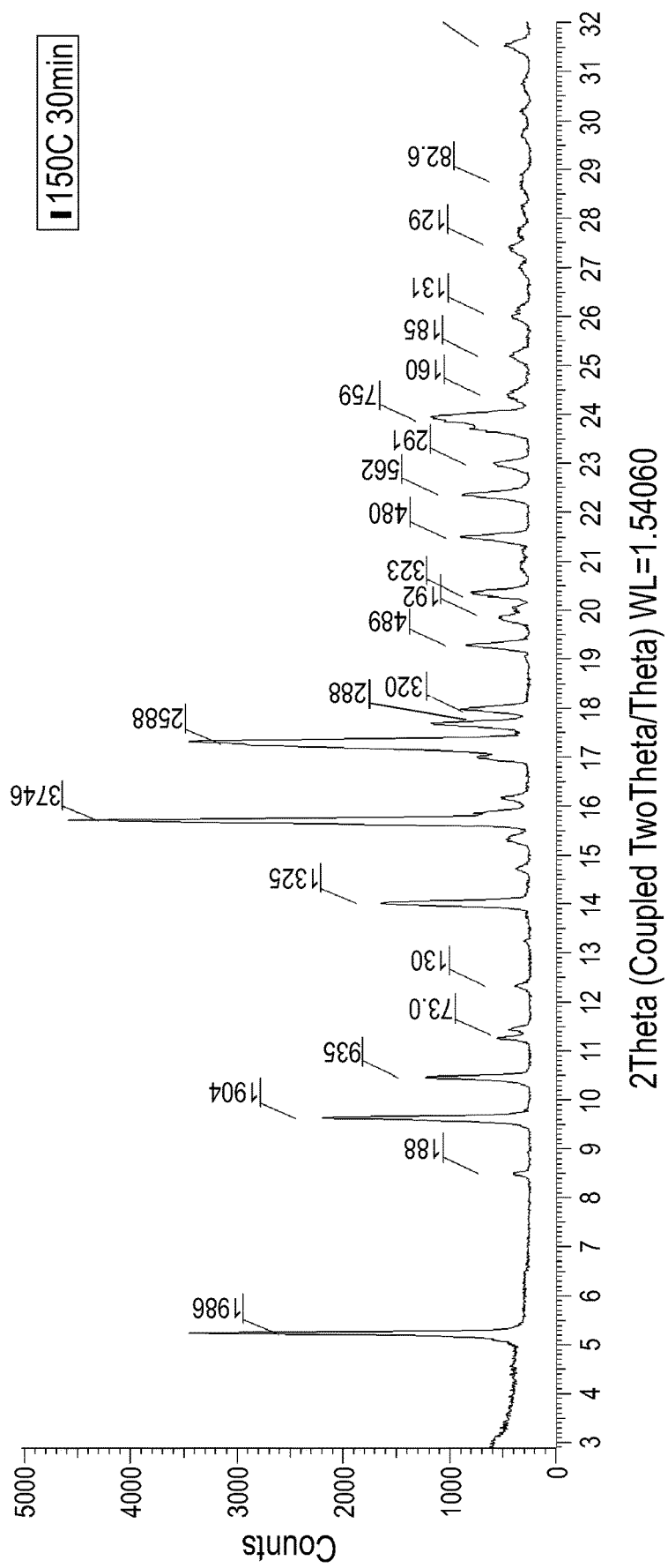
FIG. 28 depicts a powder X-ray diffraction (PXRD) pattern of crystalline Form Q of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

Crystalline Form Q was produced by heating Form P to 150° C. or drying the sample at less than 5% relative humidity for more than 1 hour. The PXRD pattern of crystalline Form Q is shown in FIG. 28 and the main peaks are listed in Table 13.

TABLE 13

PXRD peak list for crystalline Form Q

| 2θ angle | Net Intensity | Relative Intensity |
|---|---|---|
| 5.21 | 1986 | 0.53 |
| 8.49 | 188 | 0.05 |
| 9.63 | 1904 | 0.51 |
| 10.45 | 935 | 0.25 |
| 11.33 | 73 | 0.02 |
| 12.32 | 130 | 0.03 |
| 14.01 | 1325 | 0.35 |
| 15.7 | 3746 | 1.00 |
| 17.25 | 2588 | 0.69 |
| 17.75 | 288 | 0.08 |
| 17.92 | 320 | 0.09 |
| 19.27 | 489 | 0.13 |
| 19.9 | 192 | 0.05 |
| 20.28 | 323 | 0.09 |
| 21.47 | 480 | 0.13 |
| 22.35 | 562 | 0.15 |
| 22.96 | 291 | 0.08 |
| 23.89 | 759 | 0.20 |
| 24.4 | 160 | 0.04 |
| 25.2 | 185 | 0.05 |
| 26.05 | 131 | 0.03 |
| 27.46 | 129 | 0.03 |

The invention claimed is:

1. Crystalline Form B, crystalline Form C, crystalline Form D, crystalline Form E, crystalline Form F, crystalline Form H, crystalline Form J, crystalline Form K, crystalline Form L, crystalline Form M, crystalline Form N, crystalline Form P, or crystalline Form Q of (R)-1-(tert-butyl)-N-(8-(2-((1-methyl-1H-pyrazol-4-yl)amino)pyrimidin-4-yl)-2-(oxetan-3-yl)-2,3,4,5-tetrahydro-1H-benzo[c]azepin-5-yl)-1H-1,2,3-triazole-4-carboxamide.

2. The crystalline Form B of claim 1, wherein the crystalline form is
characterized by at least three or at least four powder X-ray diffraction (PXRD) peaks at 2θ angles selected from 4.1°, 7.0°, 8.1°, 12.1° and 18.3°.

3. The crystalline Form C of claim 1, wherein the crystalline form is
characterized by at least three, at least four or at least five PXRD peaks at 2θ angles selected from 3.4°, 5.5°, 6.9°, 7.7°, 8.8° and 12.5°.

4. The crystalline Form D of claim 1, wherein the crystalline form:
is characterized by at least three, at least four or at least five PXRD peaks at 2θ angles selected from 5.4°, 6.3°, 8.3°, 10.9°, 12.5° and 19.1°.

5. The crystalline Form E of claim 1, wherein the crystalline form
is characterized by at least three, at least four or at least five PXRD peaks at 2θ angles selected from 4.2°, 5.1°, 5.9°, 7.0°, 12.0° and 16.9°.

6. The crystalline Form F of claim 1, wherein the crystalline form
is characterized by at least three, four or five PXRD peaks at 2θ angles selected from 3.6°, 4.7°, 5.7°, 7.3°, 8.9°, 12.4° and 16.8°.

7. The crystalline Form H of claim 1, wherein the crystalline form
is characterized by at least three or four PXRD peaks at 2θ angles selected from 4.6°, 6.3°, 8.4°, 13.4° and 18.7°.

8. The crystalline Form J of claim 1, wherein the crystalline form
is characterized by at least three or at least four PXRD peaks at 2θ angles selected from 4.0°, 7.1°, 7.3°, 12.0°, 12.5°.

9. The crystalline Form K of claim 1, wherein the crystalline form
is characterized by at least three, at least four or at least five PXRD peaks at 2θ angles selected from 5.7°, 8.0°, 8.7°, 9.7°, 12.0° and 18.0°.

10. The crystalline Form L of claim 1, wherein the crystalline form
is characterized by at least three, at least four, at least five, at least six, at least seven or at least eight PXRD peaks at 2θ angles selected from 7.1°, 7.9°, 9.1°, 10.0°, 10.4°, 12.8°, 16.1°, 16.8° and 18.4°.

11. The crystalline Form M of claim 1, wherein the crystalline form
is characterized by at least three, at least four or at least five PXRD peaks at 2θ angles selected from 3.5°, 4.3°, 8.0°, 8.7°, 12.9° and 17.4°.

12. The crystalline Form N of claim 1, wherein the crystalline form
is characterized by at least three, four, five, six or seven PXRD peaks at 2θ angles selected from 4.8°, 7.1°, 10.4°, 11.5°, 15.2°, 17.7°, 19.8° and 22.8°.

13. The crystalline Form P of claim 1, wherein the crystalline form
is characterized by at least three, at least four or at least five PXRD peaks at 2θ angles selected from 5.3°, 9.7°, 14.2°, 15.8°, 17.5° and 24.2°.

14. The crystalline Form Q of claim 1, wherein the crystalline form
is characterized by at least three, at least four, at least five, at least six or at least seven PXRD peaks at 2θ angles selected from 5.2°, 8.5°, 9.6°, 10.5°, 14.0°, 15.7° and 17.3°.

15. A pharmaceutical composition comprising a pharmaceutically acceptable excipient and (i) the crystalline Form B, or (ii) the crystalline Form C, or (iii) the crystalline Form D, or (iv) the crystalline Form E, or (v) the crystalline Form F, or (vi) the crystalline Form H, or (vii) the crystalline Form J, or (viii) the crystalline Form K, or (ix) the crystalline Form L, or (x) the crystalline Form M, or (xi) the crystalline Form N, (xii) the crystalline Form P, or (xiii) a crystalline Form Q of claim 1.

16. A method of treating a disorder responsive to inhibition of Bruton's tyrosine kinase in a subject comprising administering to the subject an effective amount of (i) the crystalline Form B, or (ii) the crystalline Form C, or (iii) the crystalline Form D, or (iv) the crystalline Form E, or (v) the crystalline Form F, or (vi) the crystalline Form H, or (vii) the crystalline Form J, or (viii) the crystalline Form K, or (ix) the crystalline Form L, or (x) the crystalline Form M, or (xi) the crystalline Form N, (xii) the crystalline Form P, or (xiii) a crystalline Form Q of claim 1.

17. The method of claim 16, wherein the disorder is an autoimmune disorder.

18. The method of claim 17, wherein the autoimmune disorder is multiple sclerosis.

19. The crystalline Form B of claim 2, wherein the crystalline form is:
(i) characterized by PXRD peaks at 2θ angles selected from 4.1°, 7.0°, 8.1°, 12.1° and 18.3°;
(ii) characterized by PXRD peaks at 2θ angles selected from 4.1°, 7.0°, 8.1°, 12.1°, 13.0°, 14.7°, 17.6°, 18.3° and 20.7°;

(iii) characterized by a melting temperature of 158.5° C.±2° C. determined by differential scanning calorimetry (DSC) analysis;
(iv) a hygroscopic anhydrate; or
(v) is at least 70%, 80%, 85%, 90%, 95%, 97%, 99%, 99.5% or 99.9% pure.

20. The crystalline Form C of claim 3, wherein the crystalline form is:
(i) characterized by PXRD peaks at 2θ angles selected from 3.4°, 5.5°, 6.9°, 7.7°, 8.8° and 12. 5° ;
(ii) characterized by PXRD peaks at 2θ angles selected from 3.4°, 5.5°, 6.9°, 7.7°, 8.8°, 9.8°, 12.5°, 14.2°, 15.6°, 17.6°, 18.6°, 20.2° and 25.3°;
(iii) characterized by a melting temperature of 164.3° C.±2° C. determined by differential scanning calorimetry (DSC) analysis;
(iv) a hydrate; or
(v) is at least 70%, 80%, 85%, 90%, 95%, 97%, 99%, 99.5% or 99.9% pure.

21. The crystalline Form D of claim 4, wherein the crystalline form:
(i) is characterized by PXRD peaks at 2θ angles selected from 5.4°, 6.3°, 8.3°, 10.9°, 12.5°and 19.1;
(ii) is characterized by PXRD peaks at 2θ angles selected from 5.4°, 6.3°, 8.3°, 10.9°, 12.5°, 13.7°, 14.4°, 15.7°, 16.3°, 17.5°, 18.9°, 19.1°, 19.6°, 22.7°, 23.8°, 24.6°, 25.0°, 25.9°, 28.4°, 29.0°and 30.4°;
(iii) has a melting temperature of 173.2° C.±2° C. determined by differential scanning calorimetry (DSC) analysis;
(iv) is an acetic acid solvate; or
(v) is at least 70%, 80%, 85%, 90%, 95%, 97%, 99%, 99.5% or 99.9% pure.

22. The crystalline Form E of claim 5, wherein the crystalline form:
(i) is characterized by PXRD peaks at 2θ angles selected from 4.2°, 5.1°, 5.9°, 7.0°, 12.0°and 16.9°;
(ii) is characterized by PXRD peaks at 2θ angles selected from 4.2°, 5.1°, 5.9°, 7.0°, 8.5°, 8.7°, 9.8°, 10.2°, 12.0°, 12.4°, 13.7°, 16.9°, 18.1°, 18.7°, 20.7° and 26.6°; o
(iii) has a melting temperature of 167.8° C.±2° C. determined by differential scanning calorimetry (DSC) analysis;
(iv) is an anhydrate; or
(v) is at least 70%, 80%, 85%, 90%, 95%, 97%, 99%, 99.5% or 99.9% pure.

23. The crystalline Form F of claim 6, wherein the crystalline form:
(i) is characterized by PXRD peaks at 2θ angles selected from 3.6°, 4.7°, 5.7°, 7.3°, 8.9°, 12.4° and 16.8°;
(ii) is characterized by PXRD peaks at 2θ angles selected from 3.6°, 4.7°, 5.7°, 7.3°, 8.9°, 9.7°, 12.4°, 13.2°, 14.2°, 14.6°, 16.8°, 18.1°, 19.1°, 20.6°, 22.5°, 23.7°, 24.3°, 25.5° and 29.1°;
(iii) has a melting temperature of 174.7° C.±2° C. determined by differential scanning calorimetry (DSC) analysis;
(iv) is an anhydrate; or
(v) is at least 70%, 80%, 85%, 90%, 95%, 97%, 99%, 99.5% or 99.9% pure.

24. The crystalline Form H of claim 7, wherein the crystalline form:
(i) is characterized by PXRD peaks at 2θ angles selected from 4.6°, 6.3°, 8.4°, 13.4° and 18.7;
(ii) is characterized by PXRD peaks at 2θ angles selected from 4.6°, 6.3°, 8.4°, 8.8°, 11.0°, 13.4°, 14.9°, 15.6°, 16.9°, 18.7°, 19.3°, 22.6°, 24.1°, 25.3° and 26.8°;

(iii) has a melting temperature of 161.1° C.±2° C. determined by differential scanning calorimetry (DSC) analysis;
(iv) is an anhydrate; or
(v) is at least 70%, 80%, 85%, 90%, 95%, 97%, 99%, 99.5% or 99.9% pure.

25. The crystalline Form J of claim 8, wherein the crystalline form:
(i) is characterized by PXRD peaks at 2θ angles selected from 4.0°, 7.1°, 7.3°, 12.0°, 12.5°;
(ii) is characterized by PXRD peaks at 2θ angles selected from 4.0°, 6.0°, 7.1°, 7.3°, 10.5°, 12.0°, 12.5°, 15.1° and 18.1°; or
(iii) has a melting temperature of 150.2° C.±2° C. determined by differential scanning calorimetry (DSC) analysis; or
(iv) is a hydrate or hygroscopic anhydrate; or
(v) is at least 70%, 80%, 85%, 90%, 95%, 97%, 99%, 99.5% or 99.9% pure.

26. The crystalline Form K of claim 9, wherein the crystalline form:
(i) is characterized by PXRD peaks at 2θ angles selected from 5.7°, 8.0°, 8.7°, 9.7°, 12.0° and 18.0°;
(ii) is characterized by PXRD peaks at 2θ angles selected from 5.7°, 8.0°, 8.7°, 9.7°, 12.0°, 12.8°, 13.4°, 14.8°, 16.5°, 17.1°, 18.0°, 18.9°, 19.3°, 20.2°, 20.7°, 21.1°, 22.0°, 22.7° and 23.4; or
(iii) is at least 70%, 80%, 85%, 90%, 95%, 97%, 99%, 99.5% or 99.9% pure.

27. The crystalline Form L of claim 10, wherein the crystalline form:
(i) is characterized by PXRD peaks at 2θ angles selected from 7.1°, 7.9°, 9.1°, 10.0°, 10.4°, 12.8°, 16.1°, 16.8° and 18.4°;
(ii) is characterized by PXRD peaks at 2θ angles selected from 7.1°, 7.9°, 9.1°, 10.0°, 10.4°, 12.8°, 14.6°, 15.1°, 16.1°, 16.8°, 18.4°, 19.1°, 20.2°, 20.8°, 21.5°, 22.8°, 23.8°, 24.9° and 26.9; or
(iii) is at least 70%, 80%, 85%, 90%, 95%, 97%, 99%, 99.5% or 99.9% pure.

28. The crystalline Form M of claim 11, wherein the crystalline form:
(i) is characterized by PXRD peaks at 2θ angles selected from 3.5°, 4.3°, 8.0°, 8.7°, 12.9°and 17.4°;
(ii) is characterized by PXRD peaks at 2θ angles selected from 3.5°, 4.3°, 6.0°, 7.1°, 8.0°, 8.7°, 10.5°, 11.2°, 12.9° , 14.9°, 16.3°, 17.4°, 20.1°, 20.7° and 25.8°; or
(iii) is at least 70%, 80%, 85%, 90%, 95%, 97%, 99%, 99.5% or 99.9% pure.

29. The crystalline Form N of claim 12, wherein the crystalline form:
(i) is characterized by PXRD peaks at 2θ angles selected from 4.8°, 7.1°, 10.4°, 11.5°, 15.2°, 17.7°, 19.8° and 22.8°;
(ii) is characterized by PXRD peaks at 2θ angles selected from 4.8°, 7.1°, 9.5°, 10.4°, 10.9°, 11.5°, 14.2°, 15.2°, 16.3°, 17.7°, 18.3°, 19.0°, 19.8°, 20.3°, 21.2°, 22.2°, 22.8°, 23.8°, 24.5°, 25.1°, 25.8°, 27.3°, 28.5° and 29.8°;
(iii) has a melting temperature of 146.3 ° C.±2° C. determined by differential scanning calorimetry (DSC) analysis;
(iv) is a hydrate; or
(v) is at least 70%, 80%, 85%, 90%, 95%, 97%, 99%, 99.5% or 99.9% pure.

30. The crystalline Form P of claim 13, wherein the crystalline form:

(i) is characterized by PXRD peaks at 2θ angles selected from 5.3°, 9.7°, 14.2°, 15.8°, 17.5° and 24.2°;
(ii) is characterized by at least three, at least four, at least five, or at least six PXRD peaks at 2θ angles selected from 5.3°, 8.5°, 9.7°, 14.2°, 15.8°, 17.5° and 24.2°;
(iii) is characterized by PXRD peaks at 2θ angles selected from 5.3°, 8.5°, 9.7°, 14.2°, 15.8°, 17.5° and 24.2°;
(iv) is characterized by at least three or at least four PXRD peaks at 2θ angles selected from 9.7°, 14.2°, 15.8°, 17.5° and 24.2°;
(v) is characterized by PXRD peaks at 2θ angles selected from 9.7°, 14.2°, 15.8°, 17.5° and 24.2°;
(vi) is characterized by PXRD peaks at 2θ angles selected from 5.3°, 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5°;
(vii) is characterized by PXRD peaks at 2θ angles selected from 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5°;
(viii) is characterized by PXRD peaks at 2θ angles selected from 5.3°, 8.5°, 9.7°, 10.6°, 11.4°, 14.2°, 15.5°, 15.8°, 16.3°, 17.1°, 17.5°, 17.8°, 18.1°, 19.5°, 20.0°, 20.5°, 21.7°, 22.6°, 23.2°, 24.2°, 24.6°, 25.4°, 26.3° and 27.5°;
(ix) has a melting temperature of 201.3° C.±2° C. determined by differential scanning calorimetry (DSC) analysis;
(x) is a hydrate;
(xii is an anhydrate; or
(xii) is at least 70%, 80%, 85%, 90%, 95%, 97%, 99%, 99.5% or 99.9% pure.

31. The crystalline Form Q of claim 14, wherein the crystalline form:
(i) is characterized by PXRD peaks at 2θ angles selected from 5.2°, 8.5°, 9.6°, 10.5°, 14.0°, 15.7° and 17.3°;
(ii) is characterized by PXRD peaks at 2θ angles selected from 5.2°, 8.5°, 9.6°, 10.5°, 11.3°, 12.3°, 14.0°, 15.7°, 17.3°, 17.8°, 17.9°, 19.3°, 19.9°, 20.3°, 21.5°, 22.4°, 23.0°, 23.9°, 24.4°, 25.2°, 26.1° and 27.5°; or
(iii) is at least 70%, 80%, 85%, 90%, 95%, 97%, 99%, 99.5% or 99.9% pure.

* * * * *